United States Patent
Mansour et al.

(10) Patent No.: US 10,844,038 B2
(45) Date of Patent: Nov. 24, 2020

(54) 1,2-DITHIOLANE COMPOUNDS USEFUL IN NEUROPROTECTION, AUTOIMMUNE AND CANCER DISEASES AND CONDITIONS

(71) Applicant: SABILA BIOSCIENCES LLC, New City, NY (US)

(72) Inventors: Tarek S. Mansour, New City, NY (US); Colleen E. Evans, New City, NY (US)

(73) Assignee: SABILA BIOSCIENCES LLC, New City, NY (US)

( * ) Notice: Subject to any disclaimer, the term of this patent is extended or adjusted under 35 U.S.C. 154(b) by 0 days.

(21) Appl. No.: 16/331,321

(22) PCT Filed: Sep. 8, 2017

(86) PCT No.: PCT/US2017/050634
§ 371 (c)(1),
(2) Date: Mar. 7, 2019

(87) PCT Pub. No.: WO2018/049127
PCT Pub. Date: Mar. 15, 2018

(65) Prior Publication Data
US 2020/0010442 A1  Jan. 9, 2020

Related U.S. Application Data

(60) Provisional application No. 62/384,813, filed on Sep. 8, 2016.

(51) Int. Cl.
| C07D 487/04 | (2006.01) |
| C07D 339/04 | (2006.01) |
| C07C 43/29 | (2006.01) |
| C07F 5/02 | (2006.01) |
| C07F 7/18 | (2006.01) |

(52) U.S. Cl.
CPC ............ *C07D 339/04* (2013.01); *C07C 43/29* (2013.01); *C07D 487/04* (2013.01); *C07F 5/025* (2013.01); *C07F 7/1804* (2013.01)

(58) Field of Classification Search
CPC .................................................. C07D 487/04
See application file for complete search history.

(56) References Cited

U.S. PATENT DOCUMENTS

| 8,795,706 B2 | 8/2014 | Garner et al. |
| 2010/0184760 A1 | 7/2010 | Ren et al. |
| 2015/0018336 A1 | 1/2015 | Chen et al. |
| 2015/0284478 A1 | 10/2015 | Agar et al. |

FOREIGN PATENT DOCUMENTS

| WO | WO2008121742 A2 | 10/2008 |
| WO | WO 2011/141909 A2 | 11/2011 |

OTHER PUBLICATIONS

Burger's Medicinal Chemistry.edited by Manfred E. Wolff, 5th Ed. Part 1, pp. 975-977 (1995). (Year: 1995) (Year: 1995).*
Banker et al. "Modern Pharmaceutics", 3rd Ed. p. 596 (1996). (Year: 1996).*
Lind et al. PLOS ONE p. 1-20 downloaded at https://doi.org/10.1371/journal.pone.0219774 (Year: 2019) (Year: 2019).*
International Search Report and Written Opinion in corresponding PCT Application No. PCT/US2017/050634, dated Dec. 20, 2017.
Homhual et al "Bruguiesulfurol, A new Sulfur Compound from Bruguiera gymnorrhiza", Planta Med., 2006, vol. 72, pp. 255-260, abstract; p. 256, col. 1, para 1; p. 259, col. 1, para 2-3; Table 2.
International Preliminary Report on Patentability in corresponding PCT Application No. PCT/US2017/050634, dated Mar. 12, 2019.
Supplementary European Search Report dated Jan. 17, 2020 in corresponding European Application No. 17 849 588.3.

* cited by examiner

*Primary Examiner* — Emily A Bernhardt
(74) *Attorney, Agent, or Firm* — Leason Ellis LLP

(57) ABSTRACT

This invention provides compounds of the formula (I):

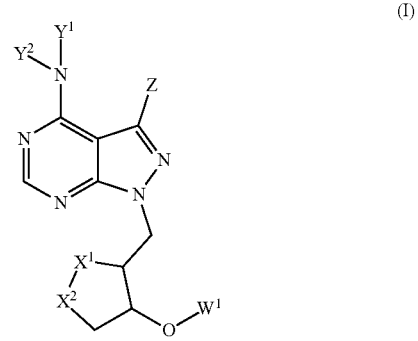

wherein $Y^1$, $Y^2$, Z, $X^1$, $X^2$, and W' are defined in the specification. These compounds are useful in the treatment of tyrosine kinases, MAPK signaling pathway kinases and PI3K/AKT/mTor signaling pathway kinases-mediated diseases or conditions, such as neurodegeneration, neuroprotection, cancer, autoimmune as well as other diseases and conditions associated with the modulation of tyrosine kinases selected from FYN, FYN Y531F, FLT3, FLT3-ITD, BRK, ITK, FRK, BTK, BMX, SRC, FGR, YES1, LCK, HCK, RET, CSK, LYN, and ROS1; MAPK pathway kinases selected from ARAF, BRAF, CRAF, ERK1/2, MEK1, MEK2, MEK3, MEK4, MEK5, MEK6, and MEK7; and PI3K/AKT/mTor pathway kinases: selected from mTor, PI3K α, PI3K β, PI3K γ, and PI3K δ.

15 Claims, No Drawings

1,2-DITHIOLANE COMPOUNDS USEFUL IN NEUROPROTECTION, AUTOIMMUNE AND CANCER DISEASES AND CONDITIONS

This application is a U.S. National Phase Application under 35 U.S.C. § 371 of International Patent Application No. PCT/US2017/050634, filed Sep. 8, 2017, and claims the benefit of priority under 35 U.S.C. Section 119(e) of U.S. Application No. 62/384,813, filed Sep. 8, 2016, all of which are incorporated by reference in their entireties. The International Application was published on Mar. 15, 2018 as International Publication No. WO 2018/049127 A1.

FIELD OF INVENTION

The present invention is directed towards novel 1,2-dithiolanes and related compounds and pharmaceutical compositions comprising the compounds, which are useful for the treatment of tyrosine kinases-mediated diseases or conditions, such as neurodegeneration, neuroprotection, cancer, autoimmune as well as other diseases and conditions associated with the modulation of tyrosine kinases. The present invention is further useful for the treatment of mitogen-activated protein kinase (MAPK) and PI3K/AKT/mTor signaling pathways mediated diseases and conditions. The present invention is further directed towards methods of treatment of diseases or conditions associated with tyrosine kinases, MAPK and PI3K/AKT/mTor signaling pathways activity and provides processes for the preparation of novel 1,2-dithiolanes.

BACKGROUND OF THE INVENTION

The human genome encodes for 518 protein kinases of which 30 distinct targets have been developed in the clinic primarily for the treatment of cancer. However, deregulation of kinase functions has also been implicated in immunological diseases and disorders, neurological diseases and disorders, metabolic diseases and disorders, and infectious disease. The utility of kinases as drug targets is driven by several factors, which include their involvement in signal transduction pathways that are dependent on a phosphotransfer cascade to elicit a real physiological response (Zhang, J. et al., Nature, 2009, 9, 28-39). Approximately 100 are tyrosine kinases, which are either receptor (RTK) or non-receptor tyrosine (NRTK) kinases. These kinases regulate several physiological mechanisms including, but not limited to, cell proliferation, cell differentiation, cell migration, and cellular metabolism by transferring the ATP terminal phosphate to one or more tyrosine or serine residues of the protein substrates (Carmi, C. et al., Biochem. Pharmcol. 2012, 84, 1388-1399). Inhibition of kinases affect signaling pathways associated with that kinase and therefore can have profound effects on cancer, autoimmune diseases and central nervous system (CNS) diseases. Many kinases are involved in oncogenesis resulting from a point mutation or deletion of an amino acid sequence, chromosome translocation or over-expression. In every case, the outcome is a hyperactive kinase that confers non-regulated growth stimulus in cells. Receptor tyrosine kinases function in transmembrane signaling, whereas non-receptor tyrosine kinases exert their activities within the cell function and nucleus affecting signal transduction, cell cycle and transcription factors.

Cancer is a major global problem. Every year, there are about 1.7 million new cancer cases and about 580,000 deaths from cancer in the United States, amounting to one in 4 deaths is due to cancer. Cancer can impact all organs and systems in the body including, but not limited to, the genital system, which includes the prostate; the digestive system that includes the colon and the pancreas; the respiratory system that includes the lung and bronchus; the breast; the urinary system that includes bladder renal and kidney; the skin; blood such as (lymphoma, leukemia, myeloma); endocrine; oral cavity and pharynx; brain; soft tissue; bones; joints; and eye (Siegel, R. et al., CA Cancer J. Clin. 2013, 63, 11-30).

The mammalian non-receptor tyrosine kinases (NRTKs) are divided into ten families: ABL, ACK, CSK, FAK, FES, FRK, JAK, SRC, SYK and TEC. In addition to their tyrosine kinase catalytic domains, they all contain non-catalytic domains that are important in enzyme regulation and substrate recognition. The SRC family kinases (SFKs) members include SRC, YES, FYN, FGR, BLK, HCK, LCK, and LYN. SFKs play key roles in regulating signal transduction by a diverse set of cell surface receptors. For example, SRC is a major activator of proteins by phosphorylation and is linked to cancer progression. Inhibitors of SRC such as bosutinib and dasatinib have demonstrated anticancer activities in humans, particularly in chronic myelogenous leukemia and acute lymphoblastic leukemia. LYN is considered a key enzyme in cell activation, while FGR is a positive regulator of mast cells which are critical for various allergic disorders (Lee, J. H. et al. J. Immunol. 2011, 187, 1807-1815). LCK is expressed in T-cells and is responsible for signaling through T-cell receptors. BLK plays a key role in B-cell receptor signaling, HCK plays a role in neutrophil migration, and YES is implicated in melanomas, basal-like and ER breast cancers, and rhabdomyosarcomas FYN is a 59 KDa protein which has three isoforms: FynB that is mainly expressed in the brain, FynT expressed in hematopoietic cells (T-cells), and FynDelta7 identified in peripheral blood mononuclear cells (Goldsmith, J. F. et al. Biochem. Biophys. Res. Commun. 2002, 298, 501-504). Through its interactions with almost 300 proteins, FYN plays key roles in physiological and pathological conditions associated with the central nervous system (CNS), cancer, the immune system and T-cell development (Kopec, A. et al. Arch. Immunol. Ther. Exp. 2006, 54, 393-401). In the CNS, FYN is implied in myelination and morphological differentiation associated with neurite formation (Schenone, S. et al. Curr. Med. Chem. 2001, 18, 2921-2942). Alteration of the Tau protein in the CNS is associated with Alzheimer's disease (AD) and in this disease state, the protein Tau is phosphorylated at Tyr18 by FYN. A set of FYN inhibitors in a cellular model of AD inhibited Tyr18-Tau phosphorylation (Tintori, C. et al. J. Med Chem. 2015, 58, 4590-4609). In a transgenic AD mouse FYN overexpression accelerates synapse loss and the onset of cognitive impairment while inhibition of FYN expression rescues synapse loss (Chin, J. et al. J. Neurosci, 2005, 25, 9694-9703). The SRC/FYN dual inhibitor saracatinib rescues memory deficits, restores synapse density and reduces microglial activation and Tau aggregation (Kaufman, A. C. et al. Ann. Neurol, 2015, 77, 953-971) in a transgenic AD mouse model. It is currently undergoing clinical evaluation in AD patients (Nygaard, H. B. et al. Alzheimer's Res. Ther. 2015, 7, 35-46). FYN and SRC knockdown contribute to cell apoptosis resulting from brain ischemia and AB neurotoxicity suggesting FYN as a promising target for neuroprotective therapy in ischemic stroke and AD (Du, C-P. et al. CNS Neuro. Therap. 2012, 18, 754-761). In oncology, overexpression of FYN is found in many cancers including glioblastoma multiformae, squamous cell carcinoma of the head and neck, melanoma, breast, ovarian, prostate and pancreatic cancer (Saito, Y. D.

et al. *Cancer* 2010, 116, 1629-1637). FYN is highly expressed in the testis and appears to have a role in spermatogenesis (Luo, J. et al. *Biol. Reprod.* 2012, 86, 1-8). FYN displays strong association with FLT3 as well as mutant FL3-ITD oncogene and cooperates with the latter by selective activation of the STAT5 pathway suggesting that FYN in combination with FLT3 inhibition will be beneficial in AML patients (Chougule, R. A. et al. *Oncotarget* 2016, 7, 9964-9974).

The oncogene BCR-ABL1 is responsible for the human Philadelphia chromosome positive chronic myeloid leukemia (CML) and B cell acute lymphocytic leukemia (ALL). In vitro and in vivo studies have demonstrated that Bcr-Abl activates FGR, LYN and HCK kinases in lymphoid cells (Hu, Y. et al. *Nature Genetics* 2004, 36, 453-461) and thus, inhibitors of FGR, LYN and HCK have utility in CML and ALL cancers. YES kinase activity has been shown to be upregulated in melanoma, head and neck, renal, lung and stomach cancers (Patel, P. R. et al. *Bioorg. Med. Chem. Lett.* 2013, 23, 4398-4403). YES1 was singled out amongst SFK as functionally involved in malignant brain-metastatic melanoma (Marchetti, D. et al. *Oncogene* 1998, 16, 3253-3260) and was shown to be a central mediator of cell growth in malignant mesothelioma cells (Sato, A. et al. *Oncol. Rep.* 2012, 28, 1889-1893). A loss-of-function screen by knock down of expression in rhabdomyosarcoma cell lines significantly inhibited cell growth in vitro suggesting YES1 as a potential target for this cancer (Yeung, C. L. et al. *Oncogene* 2013, 32, 5429-5438). Similar studies demonstrated significant effects on cell survival and growth for basal-like and HER2-positive breast cancers (Bilal, E. et al. *Genes Cancer* 2011, 1, 1063-1067).

Breast tumor kinase (BRK) is a member of the FRK family of NRTs. It is a soluble tyrosine kinase expressed in the epithelial cells of the skin and gastrointestinal tract and aberrantly expressed in melanoma, lymphoma, ovarian, prostate, colon and up to 86% of breast tumors (Ostrander, J. H. et al. *Curr. Opin. Pharmacol.* 2010, 10, 662-669). BRK was recently shown to be a key regulator of hypoxia-induced breast cancer progression (Regan-Anderson, T. M. et al. *Cancer Res.* 2013, 73, 5810-5820), thus targeting BRK expression activity may provide an effective method to block the progression of aggressive breast cancers.

The TEC family of non-receptor tyrosine kinases constitutes BTK, BMX, ITK, TEC and TXK kinases and is involved in the intracellular signaling mechanisms of cytokine receptors, lymphocyte surface antigens, heterotrimeric G-protein-coupled receptors and integrin molecules. Loss-of-function mutations in the BTK gene were reported as the cause of X-linked agammaglobulinemic. Ibrutinib, an inhibitor of BTK, has utility in patients with chronic lymphocytic leukemia and mantle cell lymphoma. FMS-like tyrosine kinase (FLT3) is a type III receptor tyrosine kinase that plays key roles in differentiation and survival of hematopoietic stem cells in bone marrow and has been observed overexpressed in acute myeloid leukemia (Smith, C. C. et al. *Nature* 2012, 485, 260-263) and acute lymphocytic leukemia (Markovic, A. *Int. J. Biochem. Cell. Biol.* 2005, 37, 1168-1172). Specific gain-of-function mutations such as FLT3-ITD, FLT3-D835Y have been identified in AML patients thus suggesting that FLT3 targeted therapy addresses an unmet medical need for FLT3 mutant positive AML patients (Li, X. et al. *J. Med. Chem.* 2015, 58, 9625-9638).

RET (REarranged during Transfection) is a single-pass transmembrane receptor tyrosine kinase that is mainly expressed in both the peripheral nervous system and the CNS. Deregulation of RET signaling can lead to thyroid cancers including medullary thyroid carcinoma (MTC) and its inherited forms which are characterized by missense mutations in RET involving cysteine (Mulligan, L. M. et al. *Nature* 1993, 363, 458-460) or methionine residues (Mulligan, L. M. et al. *J. Intern. Med.* 1998, 238, 343-346) and papillary thyroid carcinoma (PTC) associated with specific chromosomal rearrangements of RET. Chimeric RET proteins have been identified in lung adenocarcinoma of NSCLC (Song, M. *J. Med. Chem.* 2015, 58, 3672-3681). and are being investigated in the clinic with cabozantinib and vandetanib which are approved for treatment of MTC patients. Inhibitors of RET gatekeeper mutants V804L and V804M have been reported recently (Li, X. et al. *J. Med. Chem.* 2015, 58, 9625-9638) potentially for MTC therapeutics.

The ROS1 kinase is a receptor tyrosine kinase first discovered in lung adenocarcinoma and has been shown to have a role in glioblastoma (Birchmeter, C. et al. *Proc. Natl. Acad. Sci. USA* 1987, 84, 9270-9274). Like RET, ROS1 is involved in rearrangements resulting in fusion of its kinase domain to different partners (Bos, M. et al. *Transl. Lung Cancer Res.* 2013, 2, 112-121), which play a role in NSCLC. Activation of ROS1 causes downstream signaling pathways activation including STAT3, PI3K/AKT, RAS/MAPK/MEK pathways. There are no selective inhibitors of ROS1 described to date. The ErbB family of receptor tyrosine kinases and their ligands are important regulators of tumor cell proliferation, tumor angiogenesis and metastasis. (Gschwind, A. et. al., *Nat. Rev. Cancer,* 2004, 4, 361). There are four receptors in the ErbB family, EGFR (endothelial growth factor receptor), HER2, HER3 and HER4. EGFR plays a key role in signal transduction pathways controlling proliferation and apoptosis (Zhou, B-B S. et. al. *Cancer Cell,* 2006, 10, 39-50). Activation of the EGFR pathway results in downstream events stimulating five of the six hallmarks of cancer: 1) independence of growth signals 2) insensitivity to growth-inhibitory signals 3) resistance to apoptosis, 4) angiogenesis, and 5) metastasis. Thus, inhibition of EGFR signaling presents multiple opportunities for identifying novel therapeutic agents.

A number of non-tyrosine kinases are also important in cancer therapy. Mitogen-activated protein kinase (MAPK) pathways link extracellular signals to the cellular machinery that controls fundamental processes such as growth, proliferation, differentiation, migration and apoptosis. Abnormalities in MAPK signaling play a critical role in the development and progression of cancer. To date six distinct groups of MAPKs have been characterized in mammals; extracellular signal-regulated kinase (ERK)1/2, ERK3/4, ERK5, ERK7/8, Jun N-terminal kinase (JNK)1/2/3 and the p38 isoforms $\alpha/\beta/\gamma$ (ERK6) and in the ERK/MAPK module. ERK (ERK1 and ERK2) is activated upon phosphorylation by MEK (MEK1 and MEK2), which is itself activated when phosphorylated by RAF (RAF-1, B-RAF and A-RAF). The B-RAF gene is found mutated in 66% of malignant melanomas, and at a lower frequency in many other human malignancies, including colon cancer, papillary thyroid cancer and serious ovarian cancer (Davies, H. et al *Nature* 2002, 417, 949-954). ERK signaling also plays a role in disrupting the anti-proliferative effects of ligands such as transforming growth factor beta (TGFβ) and is deregulated in about one-third of all human cancers (Dhillon, A. S. et al. *Oncogene* 2007, 26, 3279-3290). A number of agents are used to treat melanoma including sorafenib, vemurafenib (B-RAF), trametinib and cobimetinib as two specific and potent MEK1/2 and MEK1 inhibitors, respectively, approved for the treatment of patients with unresectable or umetastatic nmelanoma with BRAF V600E or V600K mutation as detected by an FDA-approved tesE (Yamaguchi T, et al. *Int J Oncol.* 2011, 39, 23-31). BIX02189 is a selective inhibitor of MEK5 and ERK5.

Serine/threonine protein kinases play a central role in regulating cellular metabolism, growth and survival in response to hormones, growth factors, nutrients, energy and stress signals. Mammalian target of rapamycin (mTOR) directly or indirectly regulates the phosphorylation of at least 800 proteins and functions as part of two structurally and functionally distinct signaling complexes mTORC1 and mTORC2 (mTOR complex 1 and 2). Smg1 is another example of a kinase in this pathway. MTOR inhibitors have found utility in treating a variety of cancers such as advanced renal cell-carcinoma (temsirolimus) and everolimus indicated in patients with progressive neuroendocrine tumors pf pancreatic origin. Cyclin dependent kinases (CDKs) are serine/threonine kinases whose activity depends on a regulatory subunit—a cyclin for enzymatic activity. CDKs, proteins belonging to this family have been recently renamed as CDK1 through to CDK20. CD Ks are a major eukaryotic protein kinase family involved in the integration of extracellular and intracellular signals to modulate gene transcription and cell division (Malumbres, M. *Genome Biol.* 2014, 5, 122-132).

SUMMARY OF THE INVENTION

The present invention is directed to novel 1,2-dithiolane compounds and related compounds, pharmaceutical compositions comprising the compounds, processes for making the compounds, and methods of using the compounds and pharmaceutical compositions for the treatment and/or prevention of tyrosine, MAPK and PI3K/AKT/mTor signaling pathways kinases-mediated diseases or conditions such as neurodegeneration, neuroprotection, autoimmune and cancer. Accordingly, one embodiment of the invention is directed to compounds of formula (I):

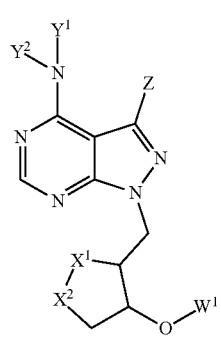

wherein:
$W^1$ is selected from a group consisting of hydrogen, $C_{1-6}$ alkyl, $C_{3-7}$ cycloalkyl, cycloalkylalkyl, aryl, arylalkyl, heterocycl, heterocyclalkyl, heteroaryl, heteroarylalkyl, alkoxyheteroarylalkyl, $C(O)R^1$, $C(O)R^2$, $C(O)OR^1$, $C(O)OR^2$, trialkylsilyl and diarylalkylsilyl;
$X^1$ and $X^2$ are at each independently selected from the group consisting of S, SO and $SO_2$;
$Y^1$ and $Y^2$ are each independently selected from the group consisting of hydrogen, $C_{1-6}$ alkyl, $C(O)R^1$, $C(O)R^2$, $C(O)OR^1$, and $C(O)OR^2$;

Z is selected from the group consisting of hydrogen, $C_{1-6}$ alkyl, $C_{1-6}$ alkenyl, $C_{1-6}$ alkynyl, arylalkynyl, halogen, $C(O)R^1$, $C(O)R^2$, $C(O)OR^1$, $C(O)OR^2$,

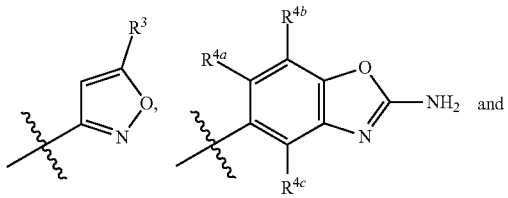

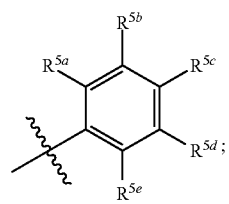

$R^1$ is selected from the group of hydrogen, $C_{1-6}$ alkyl, $C_{3-7}$ cycloalkyl and $C_{1-6}$ alkenyl;

$R^2$ is selected from the group of hydrogen, aryl, heteroaryl, arylalkyl, heteroarylalkyl;

$R^3$ is selected from the group of hydrogen, $C_{1-6}$ alkyl, $C_{3-7}$ cycloalkyl, cycloalkylalkyl and halogen;

$R^{4a}$, $R^{4b}$, and $R^{4c}$ are each independently selected from the group of hydrogen, $C_{1-6}$ alkyl, $C_{1-6}$ haloalkyl, $C_{1-6}$ alkoxy, heterocyclyl, heterocyclylalkyl, aryl, arylalkyl, aryloxy, heteroaryl, heteroarylalkyl and alkoxyheteroarylalkyl;

$R^{5a}$, $R^{5b}$, $R^{5c}$, $R^{5d}$ and $R^{5e}$ are each independently selected from the group of hydrogen, $C_{1-6}$ alkyl, $C_{1-6}$ alkenyl, $C_{1-6}$ alkynyl, $C_{1-6}$ haloalkyl, $C_{1-6}$ alkoxy, $C_{3-7}$ cycloalkyl, cycloalkylalkyl, heterocyclyl, heterocyclylalkyl, aryl, arylalkyl, aryloxy, arylalkynyl, heteroaryl, heteroarylalkyl and alkoxyheteroarylalkyl or enantiomers, diastereomers, hydrates, solvates, pharmaceutically acceptable salts, prodrugs and complexes thereof.

In another embodiment of the invention, preferred groups of compounds of formula (I), which include enantiomers, diastereomers, hydrates, solvates, pharmaceutically acceptable salts, prodrugs and complexes thereof, include those compounds in the subgroups below, wherein the other variables of formula (I) in the subgroups are defined as follows:

a) Z is the moiety

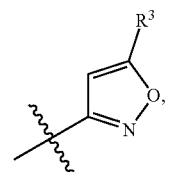

or a enantiomer, diastereomer, hydrate, solvate, a pharmaceutically acceptable salt, prodrug and complexes thereof;

b) Z is the moiety

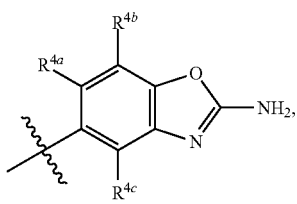

or a enantiomer, diastereomer, hydrate, solvate, a pharmaceutically acceptable salt, prodrug and complexes thereof;
c) Z is the moiety

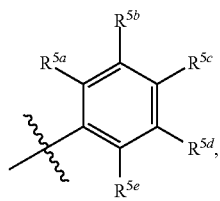

or an enantiomer, diastereomer, hydrate, solvate, a pharmaceutically acceptable salt, prodrug and complexes thereof;
d) $X^1$ and $X^2$ are S, and $Y^1$ and $Y^2$ are H, or a enantiomer, diastereomer, hydrate, solvate, a pharmaceutically acceptable salt, prodrug and complexes thereof;
e) Z is the moiety

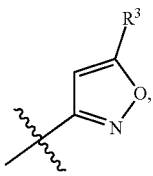

$X^1$ and $X^2$ are S, and $Y^1$ and $Y^2$ are H;
f) Z is the moiety

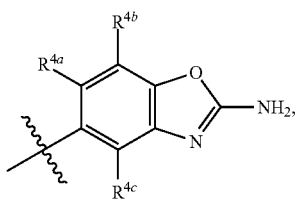

$X^1$ and $X^2$ are S, and $Y^1$ and $Y^2$ are H, or an enantiomer, diastereomer, hydrate, solvate, a pharmaceutically acceptable salt, prodrug and complexes thereof;
g) Z is arylalkynyl, $X^1$ and $X^2$ are S, and $Y^1$ and $Y^2$ are H, or an enantiomer, diastereomer, hydrate, solvate, a pharmaceutically acceptable salt, prodrug and complexes thereof.

Additional preferred compounds of the invention include those selected from the following group:
trans 3-((4-amino-3-phenyl-1H-pyrazolo[3,4-d]pyrimidin-1-yl)methyl)-1,2-dithiolan-4-yl benzoate);
trans 3-((4-amino-3-phenyl-1H-pyrazolo[3,4-d]pyrimidin-1-yl)methyl)-1,2-dithiolan-4-ol;
trans 3-((4-amino-3-(4-chlorophenyl)-1H-pyrazolo[3,4-d]pyrimidin-1-yl)methyl)-1,2-dithiolan-4-yl benzoate;
trans 3-((4-amino-3-(4-chlorophenyl)-1H-pyrazolo[3,4-d]pyrimidin-1-yl)methyl)-1,2-dithiolan-4-ol;
trans 3-((4-amino-3-(4-methoxyphenyl)-1H-pyrazolo[3,4-d]pyrimidin-1-yl)methyl)-1,2-dithiolan-4-yl benzoate;
trans 3-((4-amino-3-(4-methoxyphenyl)-1H-pyrazolo[3,4-d]pyrimidin-1-yl)methyl)-1,2-dithiolan-4-ol;
(3S,4R)-3-((4-amino-3-(4-methoxyphenyl)-1H-pyrazolo[3,4-d]pyrimidin-1-yl)methyl)-1,2-dithiolan-4-ol;
(3R,4S)-3-((4-amino-3-(4-methoxyphenyl)-1H-pyrazolo[3,4-d]pyrimidin-1-yl)methyl)-1,2-dithiolan-4-ol;
cis 3-((4-amino-3-(4-methoxyphenyl)-1H-pyrazolo[3,4-d]pyrimidin-1-yl)methyl)-1,2-dithiolan-4-yl benzoate;
cis 3-((4-amino-3-(4-methoxyphenyl)-1H-pyrazolo[3,4-d]pyrimidin-1-yl)methyl)-1,2-dithiolan-4-ol;
(3S,4S)-3-((4-amino-3-(4-methoxyphenyl)-1H-pyrazolo[3,4-d]pyrimidin-1-yl)methyl)-1,2-dithiolan-4-ol;
(3R,4R)-3-((4-amino-3-(4-methoxyphenyl)-1H-pyrazolo[3,4-d]pyrimidin-1-yl)methyl)-1,2-dithiolan-4-ol;
trans 1-((4-methoxy-1,2-dithiolan-3-yl)methyl)-3-(4-phenoxyphenyl)-1H-pyrazolo[3,4-d]pyrimidin-4-amine;
cis 1-((4-methoxy-1,2-dithiolan-3-yl)methyl)-3-(4-phenoxyphenyl)-1H-pyrazolo[3,4-d]pyrimidin-4-amine;
trans 1-((4-(benzyloxy)-1,2-dithiolan-3-yl)methyl)-3-(4-phenoxyphenyl)-1H-pyrazolo[3,4-d]pyrimidin-4-amine;
cis 1-((4-(benzyloxy)-1,2-dithiolan-3-yl)methyl)-3-(4-phenoxyphenyl)-1H-pyrazolo[3,4-d]pyrimidin-4-amine;
trans 3-((4-amino-3-(4-phenoxyphenyl)-1H-pyrazolo[3,4-d]pyrimidin-1-yl)methyl)-1,2-dithiolan-4-yl benzoate;
trans 3-((4-amino-3-(4-phenoxyphenyl)-1H-pyrazolo[3,4-d]pyrimidin-1-yl)methyl)-1,2-dithiolan-4-ol;
(3S,4R)-3-((4-amino-3-(4-phenoxyphenyl)-1H-pyrazolo[3,4-d]pyrimidin-1-yl)methyl)-1,2-dithiolan-4-ol;
(3R,4S)-3-((4-amino-3-(4-phenoxyphenyl)-1H-pyrazolo[3,4-d]pyrimidin-1-yl)methyl)-1,2-dithiolan-4-ol;
cis 3-((4-amino-3-(4-phenoxyphenyl)-1H-pyrazolo[3,4-d]pyrimidin-1-yl)methyl)-1,2-dithiolan-4-yl benzoate;
cis 3-((4-amino-3-(4-phenoxyphenyl)-1H-pyrazolo[3,4-d]pyrimidin-1-yl)methyl)-1,2-dithiolan-4-ol;
(3S,4S)-3-((4-amino-3-(4-phenoxyphenyl)-1H-pyrazolo[3,4-d]pyrimidin-1-yl)methyl)-1,2-dithiolan-4-ol;
(3R,4R)-3-((4-amino-3-(4-phenoxyphenyl)-1H-pyrazolo[3,4-d]pyrimidin-1-yl)methyl)-1,2-dithiolan-4-ol;
trans-1-((4-((tert-butyldimethylsilyl)oxy)-1,2-dithiolan-3-yl)methyl)-3-(4-phenoxyphenyl)-1-1H-pyrazolo[3,4-d]pyrimidin-4-amine;
trans-1-((4-((tert-butyldimethylsilyl)oxy)-1,2-dithiolan-3-yl)methyl)-3-(4-phenoxyphenyl)-1-1H-pyrazolo[3,4-d]pyrimidin-4-amine; and
trans 3-((4-amino-3-(4-phenoxyphenyl)-1H-pyrazolo[3,4-d]pyrimidin-1-yl)methyl)-1,2-dithiolan-4-ol;
trans 3-((4-amino-3-(phenylethynyl)-1H-pyrazolo[3,4-d]pyrimidin-1-yl)methyl-1,2-dithiolan-4-yl benzoate,
trans 3-(4-amino-3-(phenylethynyl)-1H-pyrazolo[3,4-d]pyrimidin-1-yl)methyl-1,2-dithiolan-4-ol,
trans 3-((4-amino-3-(phenylethynyl)-1H-pyrazolo[3,4-d]pyrimidin-1-yl)methyl-1-oxido-1,2-dithiolan-4-yl benzoate,
trans 3-((4-amino-3-(2-aminobenzo[d]oxazol-5-yl)-1H-pyrazolo[3,4-d]pyrimidin-1-yl)methyl)-1,2-dithiolan-4-yl benzoate,
trans 3-((4-amino-3-(2-aminobenzo[d]oxazol-5-yl)-1H-pyrazolo[3,4-d]pyrimidin-1-yl)methyl)-1,2-dithiolan-4-ol,
trans 3-((4-amino-3-(2-aminobenzo[d]oxazol-5-yl)-1H-pyrazolo[3,4-d]pyrimidin-1-yl)methyl)-1-oxido-1,2-dithiolan-4-yl benzoate, trans 3-((4-amino-3-(2-aminobenzo[d]oxazol-5-yl)-1H-pyrazolo[3,4-d]pyrimidin-1-yl)methyl)-4-hydroxy-1,2-dithiolane 1-oxide, trans 3-((4-amino-3-(4-(2-fluorophenoxyphenyl)-1H-pyrazolo[3,4-d]pyrimidin-1-yl)methyl)-1,2-dithiolan-4-yl benzoate, trans 3-((4-amino-3-(4-(2-fluorophenoxyphenyl)-1H-pyrazolo[3,4-d]pyrimidin-1-yl)methyl)-1,2-dithiolan-4-ol, trans 3-((4-amino-3-(3-(3-fluoro-4-phenoxyphenyl)-1H-pyrazolo[3,4-d]pyrimidin-1-yl)methyl)-1,2-dithiolan-4-yl benzoate and, trans 3-((4-amino-3-(3-(3-fluoro-4-phenoxyphenyl)-1H-pyrazolo[3,4-d]pyrimidin-1-yl)methyl)-1,2-dithiolan-4-ol; or an enantiomer, diastereomer, hydrate, solvate, a pharmaceutically acceptable salt, prodrug and complexes thereof.

In another embodiment of the invention, additional preferred groups of compounds of Formula (I), which include enantiomers, diastereomers, hydrates, solvates, pharmaceutically acceptable salts, prodrugs and complexes thereof, include those compounds in the subgroups below, wherein the other variables of formula (I) in the subgroups are defined as follows:

a) Z is the moiety

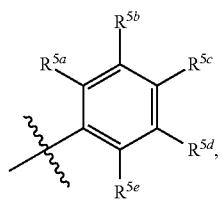

$Y^1$ is H; $R^{5a}$, $R^{5b}$, $R^{5c}$, $R^{5d}$, and $R^{5e}$ are H, and $X^1$, $X^2$, $Y^2$, $R^{5c}$ and $W^1$ are selected as a single group from one of the following groups:

| Group Number | $X^1$ | $X^2$ | $Y^2$ | $R^{5c}$ | $W^1$ |
|---|---|---|---|---|---|
| 1 | S | SO | H | OPhenyl | H, |
| 2 | SO | S | H | OPhenyl | H, |
| 3 | S | SO | H | OPhenyl | $CH_3$, |
| 4 | SO | S | H | OPhenyl | $CH_3$, |
| 5 | S | SO | $CO_2$-t-Butyl | OPhenyl | H, |
| 6 | SO | S | $CO_2$-t-Butyl | OPhenyl | H, |
| 7 | S | SO | $CO_2$-t-Butyl | OPhenyl | $CH_3$, |
| 8 | SO | S | $CO_2$-t-Butyl | OPhenyl | $CH_3$, |
| 9 | S | SO | $COCH_3$ | OPhenyl | $CO_2CH_3$, |
| 10 | SO | S | $COCH_3$ | OPhenyl | $CO_2CH_3$, |
| 11 | S | SO | H | $OCH_3$ | H, |
| 12 | SO | S | H | $OCH_3$ | H, |
| 13 | S | SO | H | $OCH_3$ | $CH_3$, |
| 14 | SO | S | H | $OCH_3$ | $CH_3$, |
| 15 | SO | SO | H | OPhenyl | H and |
| 16 | SO | SO | H | $OCH_3$ | H | or an enantiomer, diastereomer, hydrate, solvate, prodrug, complex, or pharmaceutically acceptable salt form thereof;

b) Z is the moiety

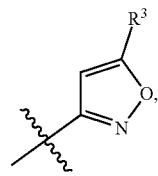

$Y^1$ is H, and $X^1$, $X^2$, $Y^2$, $R^3$ and $W^1$ are selected are selected as a single group from one of the following groups:

| Group Number | $X^1$ | $X^2$ | $Y^2$ | $R^3$ | $W^1$ |
|---|---|---|---|---|---|
| 1 | S | SO | H | Phenyl | H, |
| 2 | SO | S | H | Phenyl | H, |
| 3 | S | SO | H | $CH_2$Phenyl | $CH_3$, |
| 4 | SO | S | H | $CH_2$Phenyl | $CH_3$, |
| 5 | S | SO | $CO_2$-t-Butyl | c-propyl | H, |
| 6 | SO | S | $CO_2$-t-Butyl | c-propyl | H, |
| 7 | S | SO | $CO_2$-t-Butyl | c-propyl | $CH_3$, |
| 8 | SO | S | $CO_2$-t-Butyl | c-propyl | $CH_3$, |
| 9 | S | SO | $COCH_3$ | c-propyl | c-pentyl, |
| 10 | SO | S | $COCH_3$ | c-propyl | c-pentyl, |
| 11 | S | SO | H | c-butyl | $CH_3$, |
| 12 | SO | S | H | c-butyl | $CH_3$, |
| 13 | S | SO | H | Br | $CH_3$, |
| 14 | SO | S | H | Br | $CH_3$, |
| 15 | S | SO | H | i-propyl | H and |
| 16 | SO | S | H | i-propyl | H | or an enantiomer, diastereomer, hydrate, solvate, prodrug, complex, or pharmaceutically acceptable salt form thereof;

c) Z is the moiety

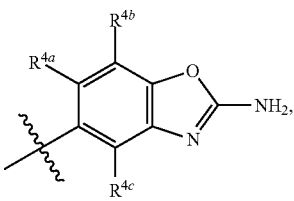

$Y^1$ is H, and $X^1$, $X^2$, $Y^2$, $R^{4b}$ and $W^1$ are selected as a single group from one of the following groups:

| Group Number | $X^1$ | $X^2$ | $Y^2$ | $R^{4b}$ | $W^1$ |
|---|---|---|---|---|---|
| 1 | S | SO | H | Cl | H, |
| 2 | SO | S | H | Cl | H, |
| 3 | S | SO | H | F | $CH_3$, |
| 4 | SO | S | H | F | $CH_3$, |
| 5 | S | SO | $CO_2$-t-Butyl | $OCH_3$ | H, |
| 6 | SO | S | $CO_2$-t-Butyl | $OCH_3$ | H, |
| 7 | S | SO | $CO_2$-t-Butyl | F | $CH_3$, |
| 8 | SO | S | $CO_2$-t-Butyl | F | $CH_3$, |
| 9 | S | SO | $COCH_3$ | c-propyl | c-pentyl, |
| 10 | SO | S | $COCH_3$ | c-propyl | c-pentyl, |
| 11 | S | SO | H | H | $CH_3$, |
| 12 | SO | S | H | H | $CH_3$, |
| 13 | S | SO | H | H | Phenyl, |
| 14 | SO | S | H | H | Phenyl, |
| 15 | S | SO | H | F | H and |
| 16 | SO | S | H | F | H | or an enantiomer, diastereomer, hydrate, solvate, prodrug, complex, or pharmaceutically acceptable salt form thereof; and d) Z is ethynylbenzene, $Y^1$ is H, and $X^1$, $X^2$, $Y^2$ and $W^1$ are selected as a single group from one of the following groups:

| Group Number | $X^1$ | $X^2$ | $Y^2$ | $W^1$ |
|---|---|---|---|---|
| 1 | S | SO | H | H, |
| 2 | SO | S | H | H, |
| 3 | S | SO | H | $CH_3$, |
| 4 | SO | S | H | $CH_3$, |
| 5 | S | SO | $CO_2$-t-Butyl | H, |
| 6 | SO | S | $CO_2$-t-Butyl | H, |
| 7 | S | SO | $CO_2$-t-Butyl | $CH_3$, |
| 8 | SO | S | $CO_2$-t-Butyl | $CH_3$, |
| 9 | S | SO | $COCH_3$ | $CO_2$—$CH_3$, |
| 10 | SO | S | $COCH_3$ | $CO_2$—$CH_3$, |
| 11 | S | SO | H | c-pentyl, |
| 12 | SO | S | H | c-pentyl, |
| 13 | S | SO | H | c-propyl, |
| 14 | SO | S | H | c-propyl, |
| 15 | S | SO | H | $CH_2$Phenyl and |
| 16 | SO | S | H | $CH_2$Phenyl, | or an enantiomer, diastereomer, hydrate, solvate, prodrug, complex, or pharmaceutically acceptable salt form thereof.

The present invention further provides a pharmaceutical composition which comprises an effective amount of one or more compounds according to the present invention or an enantiomer, diastereomer, hydrate, solvate, pharmaceutically acceptable salt, prodrug and complexes thereof, and an excipient or a pharmaceutically acceptable carrier.

The present invention further provides a method of modulating the activity of tyrosine kinases, MAPK pathway kinases, and PI3K/AKT/mTor pathway kinases in a mammal, wherein the tyrosine kinases are selected from FYN, FYN Y531F, FLT3, FLT3-ITD, BRK, ITK, FRK, BTK, BMX, SRC, FGR, YES1, LCK, HCK, RET, CSK, LYN, ROS1; MAPK pathway kinases are selected from ARAF, BRAF, CRAF, ERK1/2, MEK1, MEK2, MEK3, MEK4, MEK5, MEK6, MEK7; and PI3K/AKT/mTor pathway kinases are selected from mTor, PI3K α, PI3K β, PI3K γ, PI3K δ, comprising administering to the mammal a compound of formula (I) or an enantiomer, diastereomer, hydrate, solvate, pharmaceutically acceptable salt, prodrug and complexes thereof.

The present invention further provides methods of ameliorating, treating or preventing diseases that involve modulation of tyrosine, MAPK and PI3K/AKT/mTor pathway kinases including NRTKs such as SRFs and TEC, and RTKs such as FLT3, RET, and FRK families. These diseases include, for example, neurodegeneration, neuroprotection, Alzheimer's disease, ischemic stroke, autoimmune diseases, T-cell disorders, cancer such as, melanoma, adenocarcinoma, carcinoma, leukemia, chronic lymphoblastic leukemia, acute myeloid leukemia, adenocarcinoma, thyroid cancer, papillary thyroid carcinoma, medullary thyroid carcinoma, non-small cell lung cancer, small cell lung cancer, glioblastoma multiforme, colon, breast, prostate, testicular cancer malignant peripheral nerve sheath tumors. The method comprises administering to a subject an effective amount of a compound or a pharmaceutically acceptable salt thereof or composition according to the present invention and an excipient. Particular embodiments of the present invention provide methods for amerliorating, treating or preventing diseases that involve modulation of tyrosine kinases including NRTKs such as SRFs and Tec, RTKs such as FLT3, RET, FRK families, MAPK and PI3K/AKT/mTor pathway kinases. Embodiments of the present invention further relate to a method for treating or preventing diseases that involve modulation of tyrosine kinases including FYN, FYN Y531F, FLT3, FLT3-ITD, BRK, ITK, FRK, BTK, BMX, SRC, FGR, YES1, LCK, HCK, RET, CSK, LYN, ROS1; MAPK pathway kinases ARAF, BRAF, CRAF, ERK1/2, MEK1, MEK2, MEK3, MEK4, MEK5, MEK6, MEK7 and PI3K/AKT/mTor pathway kinases: mTor, PI3K α, PI3K β, PI3K γ, PI3K δ.

The present invention further provides processes for preparing the compounds of the present invention. In one embodiment, a process is provided for the preparation of 1,2-dithiolane compounds of formula (I)

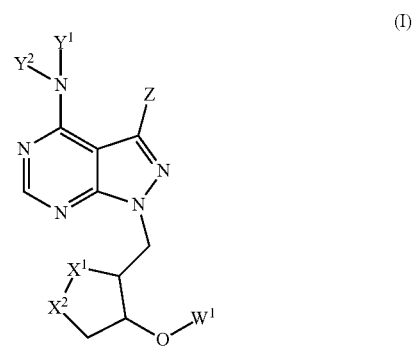

(I)

or enantiomers, diastereomers, hydrates, solvates, pharmaceutically acceptable salts, prodrugs and complexes thereof, wherein:

$W^1$ is hydrogen;

$X^1$ and $X^2$ are each independently selected from the group consisting of S, SO and $SO_2$;

$Y^1$ and $Y^2$ are each independently selected from the group consisting of hydrogen, $C_{1-6}$ alkyl, $C(O)R^1$, $C(O)R^2$, $C(O)OR^1$, and $C(O)OR^2$;

Z is selected from the group consisting of hydrogen, $C_{1-6}$ alkyl, $C_{1-6}$ alkenyl, $C_{1-6}$ alkynyl, arylalkynyl, halogen, $C(O)R^1$, $C(O)R^2$, $C(O)OR^1$, $C(O)OR^2$,

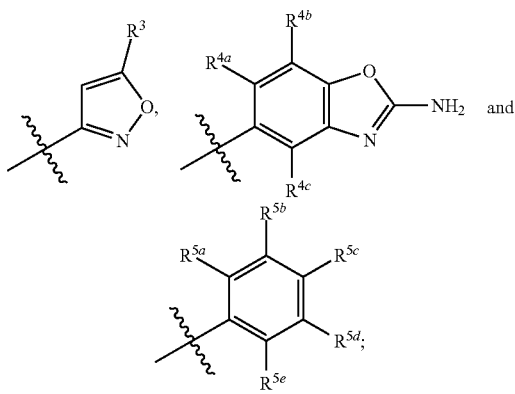

$R^1$ is selected from the group of hydrogen, $C_{1-6}$ alkyl, $C_{3-7}$ cycloalkyl and $C_{1-6}$ alkenyl;

$R^2$ is selected from the group of hydrogen, aryl, heteroaryl, arylalkyl, heteroarylalkyl;

$R^3$ is selected from the group of hydrogen, $C_{1-6}$ alkyl, $C_{3-7}$ cycloalkyl, cycloalkylalkyl and halogen;

$R^{4a}$, $R^{4b}$, and $R^{4c}$ are each independently selected from the group of hydrogen, $C_{1-6}$ alkyl, $C_{1-6}$ haloalkyl, $C_{1-6}$ alkoxy, heterocyclyl, heterocyclylalkyl, aryl, arylalkyl, aryloxy, heteroaryl, heteroarylalkyl and alkoxyheteroarylalkyl;

$R^{5a}$, $R^{5b}$, $R^{5c}$, $R^{5d}$ and $R^{5e}$ are each independently selected from the group of hydrogen, $C_{1-6}$ alkyl, $C_{1-6}$ alkenyl, $C_{1-6}$ alkynyl, $C_{1-6}$ haloalkyl, $C_{1-6}$ alkoxy, $C_{3-7}$ cycloalkyl, cycloalkylalkyl, heterocyclyl, heterocyclylalkyl, aryl, arylalkyl, aryloxy, arylalkynyl, heteroaryl, heteroarylalkyl and alkoxyheteroarylalkyl;

which process comprises the steps of:

a. reacting a 3-substituted-1H-pyrazolo[3,4-d]pyrimidin-4-substituted amine having the formula

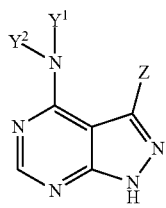

with an inorganic base such as cesium carbonate in a polar aprotic solvent such as N,N dimethyl formamide followed by addition of a substituted 1,2-dithiane compound having the formula

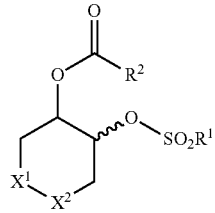

optionally with microwave irradiation to produce a substituted product of the formula

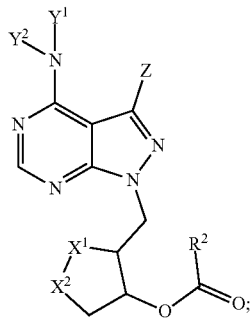

b. further reacting the substituted product with an inorganic base in a polar protic or aprotic solvent, optionally with microwave irradiation to produce a product of the formula

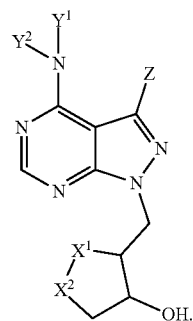

In another embodiment, a process is provided for the preparation of a mixture of sulfoxides of formula A and of sulfoxides of formula B

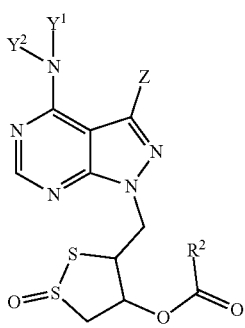
(A)

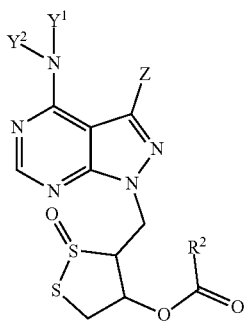
(B)

wherein:

$Y^1$ and $Y^2$ are each independently selected from the group consisting of hydrogen, $C_{1-6}$ alkyl, $C(O)R^1$, $C(O)R^2$, $C(O)OR^1$, and $C(O)OR^2$;

Z is selected from the group consisting of hydrogen, $C_{1-6}$ alkyl, $C_{1-6}$ alkenyl, $C_{1-6}$ alkynyl, arylalkynyl, halogen, $C(O)R^1$, $C(O)R^2$, $C(O)OR^1$, $C(O)OR^2$,

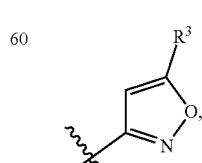 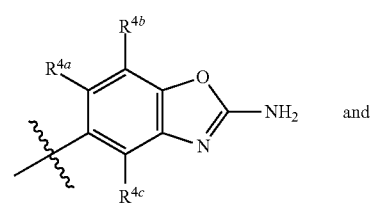 and

-continued

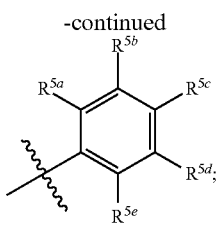

$R^1$ is selected from the group of hydrogen, $C_{1-6}$ alkyl, $C_{3-7}$ cycloalkyl and $C_{1-6}$ alkenyl;
$R^2$ is selected from the group of hydrogen, aryl, heteroaryl, arylalkyl, heteroarylalkyl;
$R^3$ is selected from the group of hydrogen, $C_{1-6}$ alkyl, $C_{3-7}$ cycloalkyl, cycloalkylalkyl and halogen;
$R^{4a}$, $R^{4b}$, and $R^{4c}$ are each independently selected from the group of hydrogen, $C_{1-6}$ alkyl, $C_{1-6}$ haloalkyl, $C_{1-6}$ alkoxy, heterocyclyl, heterocyclylalkyl, aryl, arylalkyl, aryloxy, heteroaryl, heteroarylalkyl and alkoxyheteroarylalkyl;
$R^{5a}$, $R^{5b}$, $R^{5c}$, $R^{5d}$ and $R^{5e}$ are each independently selected from the group of hydrogen, $C_{1-6}$ alkyl, $C_{1-6}$ alkenyl, $C_{1-6}$ alkynyl, $C_{1-6}$ haloalkyl, $C_{1-6}$ alkoxy, $C_{3-7}$ cycloalkyl, cycloalkylalkyl, heterocyclyl, heterocyclylalkyl, aryl, arylalkyl, aryloxy, arylalkynyl, heteroaryl, heteroarylalkyl and alkoxyheteroarylalkyl;
which process comprises the steps of:
a. contacting a compound of the formula

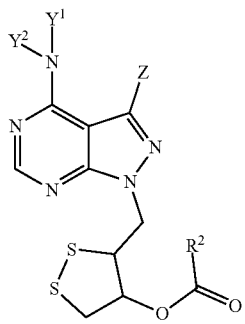

with an oxidizing agent in a polar protic or aprotic solvent with heating and optional microwave irradiation and isolating the mixture of sulfoxides A and sulfoxides B.

In another embodiment, a process is provided for the preparation of 1,2-dithiolane compounds of formula (I):

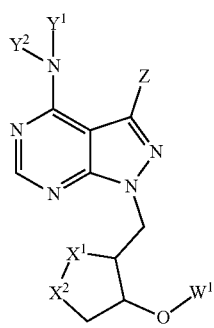

wherein:
$W^1$ is selected from a group consisting of hydrogen, $C_{1-6}$ alkyl, $C_{3-7}$ cycloalkyl, cycloalkylalkyl, aryl, arylalkyl, heterocycl, heterocycyclalkyl, heteroaryl, heteroarylalkyl, alkoxyheteroarylalkyl, $C(O)R^1$, $C(O)R^2$, $C(O)OR^1$, $C(O)OR^2$, trialkylsilyl and diarylalkylsilyl;

$X^1$ and $X^2$ are at each independently selected from the group consisting of S, SO and $SO_2$;

$Y^1$ and $Y^2$ are each independently selected from the group consisting of hydrogen, $C_{1-6}$ alkyl, $C(O)R^1$, $C(O)R^2$, $C(O)OR^1$, and $C(O)OR^2$;

Z is selected from the group consisting of hydrogen, $C_{1-6}$ alkyl, $C_{1-6}$ alkenyl, $C_{1-6}$ alkynyl, arylalkynyl, halogen, $C(O)R$, $C(O)R^2$, $C(O)OR^1$, $C(O)OR^2$,

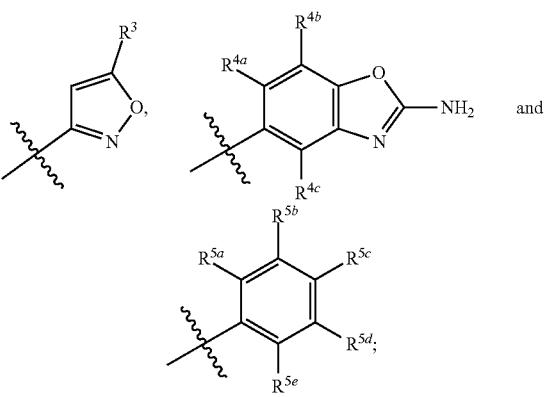

$R^1$ is selected from the group of hydrogen, $C_{1-6}$ alkyl, $C_{3-7}$ cycloalkyl and $C_{1-6}$ alkenyl;

$R^2$ is selected from the group of hydrogen, aryl, heteroaryl, arylalkyl, heteroarylalkyl;

$R^3$ is selected from the group of hydrogen, $C_{1-6}$ alkyl, $C_{3-7}$ cycloalkyl, cycloalkylalkyl and halogen;

$R^{4a}$, $R^{4b}$, and $R^{4c}$ are each independently selected from the group of hydrogen, $C_{1-6}$ alkyl, $C_{1-6}$ haloalkyl, $C_{1-6}$ alkoxy, heterocyclyl, heterocyclylalkyl, aryl, arylalkyl, aryloxy, heteroaryl, heteroarylalkyl and alkoxyheteroarylalkyl;

$R^{5a}$, $R^{5b}$, $R^{5c}$, $R^{5d}$ and $R^{5e}$ are each independently selected from the group of hydrogen, $C_{1-6}$ alkyl, $C_{1-6}$ alkenyl, $C_{1-6}$ alkynyl, $C_{1-6}$ haloalkyl, $C_{1-6}$ alkoxy, $C_{3-7}$ cycloalkyl, cycloalkylalkyl, heterocyclyl, heterocyclylalkyl, aryl, arylalkyl, aryloxy, arylalkynyl, heteroaryl, heteroarylalkyl and alkoxyheteroarylalkyl;

which process comprises the steps of:
a. reacting a 3-substituted-1H-pyrazolo[3,4-d]pyrimidin-4-substituted amine having the formula

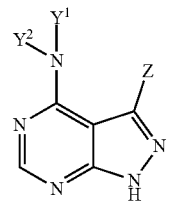

with an inorganic base such as cesium carbonate in a polar aprotic solvent such as N,N dimethyl formamide followed by addition of a substituted 1,2-dithiane compound having the formula

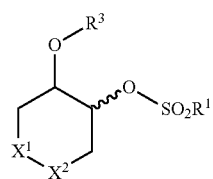

optionally with microwave irradiation to produce a substituted product of the formula

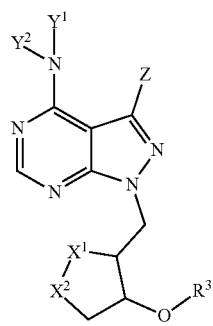

where $W^1$ is $OR^3$, or enantiomers, diastereomers, hydrates, solvates, pharmaceutically acceptable salts, prodrugs and complexes thereof.

In another embodiment, a process is provided for the preparation of 1,2-dithiolane compounds of formula (I):

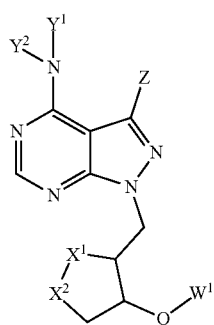

(I)

wherein:

$W^1$ is selected from the group consisting of hydrogen, $C_{1-6}$ alkyl, $C_{3-7}$ cycloalkyl, cycloalkylalkyl, aryl, arylalkyl, heterocycl, heterocycyclalkyl, heteroaryl, heteroarylalkyl, alkoxyheteroarylalkyl, $C(O)R^1$, $C(O)R^2$, $C(O)OR^1$, $C(O)OR^2$, trialkylsilyl and diarylalkylsilyl;

$X^1$ and $X^2$ are each independently selected from the group consisting of S, SO and $SO_2$;

$Y^1$ and $Y^2$ are each independently selected from the group consisting of hydrogen, $C_{1-6}$ alkyl, $C(O)R^1$, $C(O)R^2$, $C(O)OR^1$, and $C(O)OR^2$;

Z is selected from the group consisting of hydrogen, $C_{1-6}$ alkyl, $C_{1-6}$ alkenyl, $C_{1-6}$ alkynyl, arylalkynyl, halogen, $C(O)R^1$, $C(O)R^2$, $C(O)OR^1$, $C(O)OR^2$,

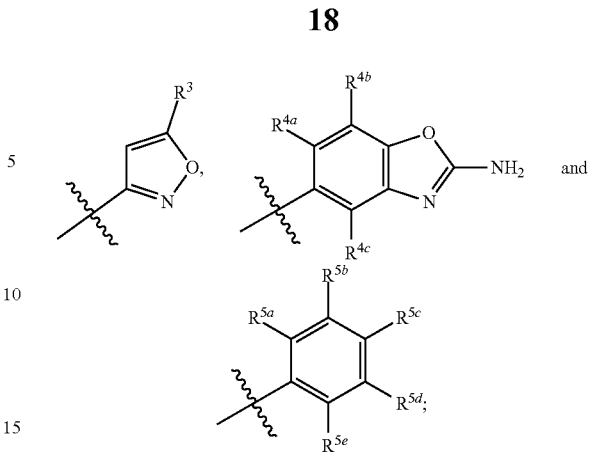

$R^1$ is selected from the group of hydrogen, $C_{1-6}$ alkyl, $C_{3-7}$ cycloalkyl and $C_{1-6}$ alkenyl;

$R^2$ is selected from the group of hydrogen, aryl, heteroaryl, arylalkyl, heteroarylalkyl;

$R^3$ is selected from the group of hydrogen, $C_{1-6}$ alkyl, $C_{3-7}$ cycloalkyl, cycloalkylalkyl and halogen;

$R^{4a}$, $R^{4b}$, and $R^{4c}$ are each independently selected from the group of hydrogen, $C_{1-6}$ alkyl, $C_{1-6}$ haloalkyl, $C_{1-6}$ alkoxy, heterocyclyl, heterocyclylalkyl, aryl, arylalkyl, aryloxy, heteroaryl, heteroarylalkyl and alkoxyheteroarylalkyl;

$R^{5a}$, $R^{5b}$, $R^{5c}$, $R^{5d}$ and $R^{5e}$ are each independently selected from the group of hydrogen, $C_{1-6}$ alkyl, $C_{1-6}$ alkenyl, $C_{1-6}$ alkynyl, $C_{1-6}$ haloalkyl, $C_{1-6}$ alkoxy, $C_{3-7}$ cycloalkyl, cycloalkylalkyl, heterocyclyl, heterocyclylalkyl, aryl, arylalkyl, aryloxy, arylalkynyl, heteroaryl, heteroarylalkyl and alkoxyheteroarylalkyl;

which process comprises the steps of:

a. reacting a 3-substituted 1H-pyrazolo[3,4-d]pyrimidin-4-substituted amine having the formula

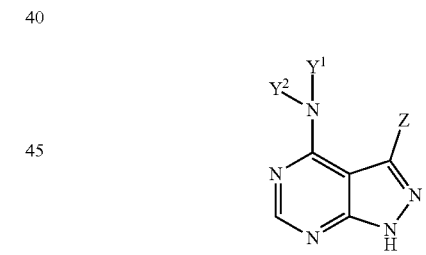

with an inorganic base in a polar aprotic solvent followed by reaction with a substituted 1,2-dithiane compound having the formula

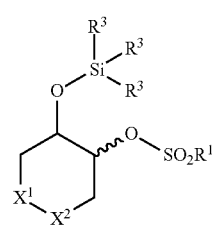

optionally with microwave irradiation to produce a substituted product of the formula

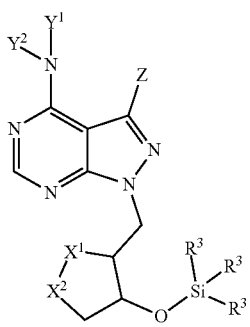

or enantiomers, diastereomers, hydrates, solvates, pharmaceutically acceptable salts, prodrugs and complexes thereof.

The process further comprises reacting the substituted product of the formula

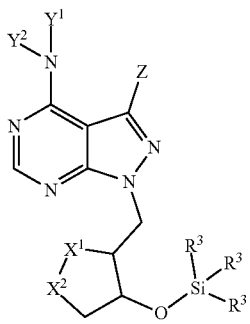

or enantiomers, diastereomers, hydrates, solvates, pharmaceutically acceptable salts, prodrugs and complexes thereof with an acid in a polar protic or aprotic solvent, optionally with microwave irradiation to produce a product of the formula

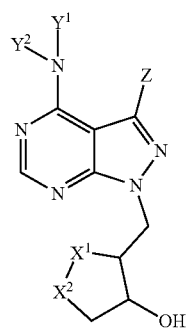

or enantiomers, diastereomers, hydrates, solvates, pharmaceutically acceptable salts, prodrugs and complexes thereof.

In another embodiment, a process is provided for the preparation of 1,2-dithiolane compounds of formula (I):

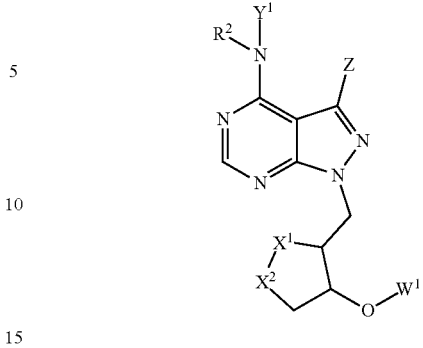

wherein:

$W^1$ is hydrogen;

$X^1$ and $X^2$ are at each independently selected from the group consisting of S, SO and $SO_2$;

$Y^1$ and $Y^2$ are each independently selected from the group consisting of hydrogen, $C_{1-6}$ alkyl, $C(O)R^1$, $C(O)R^2$, $C(O)OR^1$, and $C(O)OR^2$;

Z is selected from the group consisting of hydrogen, $C_{1-6}$ alkyl, $C_{1-6}$ alkenyl, $C_{1-6}$ alkynyl, arylalkynyl, halogen, $C(O)R^1$, $C(O)R^2$, $C(O)OR^1$, $C(O)OR^2$,

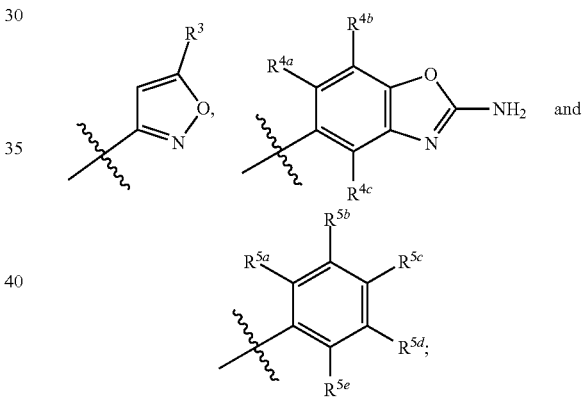

$R^1$ is selected from the group of hydrogen, $C_{1-6}$ alkyl, $C_{3-7}$ cycloalkyl and $C_{1-6}$ alkenyl;

$R^2$ is selected from the group of hydrogen, aryl, heteroaryl, arylalkyl, heteroarylalkyl;

$R^3$ is selected from the group of hydrogen, $C_{1-6}$ alkyl, $C_{3-7}$ cycloalkyl, cycloalkylalkyl and halogen;

$R^{4a}$, $R^{4b}$, and $R^{4c}$ are each independently selected from the group of hydrogen, $C_{1-6}$ alkyl, $C_{1-6}$ haloalkyl, $C_{1-6}$ alkoxy, heterocyclyl, heterocyclylalkyl, aryl, arylalkyl, aryloxy, heteroaryl, heteroarylalkyl and alkoxyheteroarylalkyl;

$R^{5a}$, $R^{5b}$, $R^{5c}$, $R^{5d}$ and $R^{5e}$ are each independently selected from the group of hydrogen, $C_{1-6}$ alkyl, $C_{1-6}$ alkenyl, $C_{1-6}$ alkynyl, $C_{1-6}$ haloalkyl, $C_{1-6}$ alkoxy, $C_{3-7}$ cycloalkyl, cycloalkylalkyl, heterocyclyl, heterocyclylalkyl, aryl, arylalkyl, aryloxy, arylalkynyl, heteroaryl, heteroarylalkyl and alkoxyheteroarylalkyl;

which process comprises the steps of:

a. reacting a 3-substituted 1H-pyrazolo[3,4-d]pyrimidin-4-substituted amine having the formula

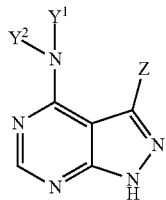

with a silyl compound having the formula

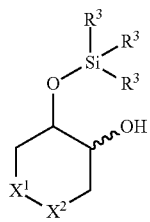

in the presence of an azodicarboxylate and triarylphosphine in a polar aprotic solvent, optionally with microwave irradiation to produce a substituted product of the formula

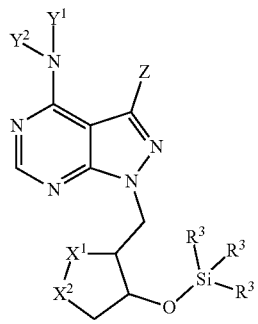

or enantiomers, diastereomers, hydrates, solvates, pharmaceutically acceptable salts, prodrugs and complexes thereof.

The process further comprises reacting the substituted product of the formula

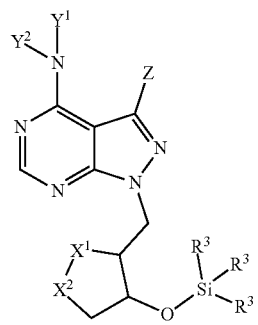

or enantiomers, diastereomers, hydrates, solvates, pharmaceutically acceptable salts, prodrugs and complexes thereof with an acid in a polar protic or aprotic solvent, optionally with microwave irradiation to produce a product of the formula

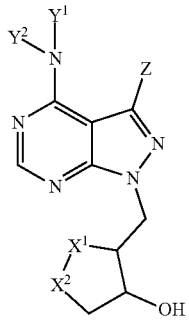

or enantiomers, diastereomers, hydrates, solvates, pharmaceutically acceptable salts, prodrugs and complexes thereof.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The tyrosine kinases, MAPK pathway kinases and the PI3K/AKT/mTor pathway kinases inhibitors of the present invention are capable of treating and preventing diseases associated with modulating tyrosine kinases including NRTKs such as SKFs and TEC family, RTKs such as FLT3, RET, and FRK family, MAPK pathway kinases such as RAF, MEK and ERK kinases, and PI3K/AKT/mTor pathway kinases such as mTor, PI3K α, PI3K β, PI3K γ, PI3K δ. These diseases include, for example, neurodegeneration, neuroprotection, Alzheimer's disease, ischemic stroke, autoimmune diseases, T-cell disorders, cancer such as, melanoma, adenocarcinoma, carcinoma, leukemia, chronic lymphoblastic leukemia, acute myeloid leukemia, adenocarcinoma, thyroid cancer, papillary thyroid carcinoma, medullary thyroid carcinoma, non-small cell lung cancer, small cell lung cancer, glioblastoma multiforme, colon, breast, prostate, testicular cancer malignant peripheral nerve sheath tumors. The tyrosine kinases inhibitors of the present invention are capable of treating and preventing diseases associated with modulating tyrosine kinase activity. It has been discovered that inhibition of tyrosine kinases activity will prevent neurodegeneration, neuroprotection, T-cell disorders, tumor cell proliferation, tumor angiogenesis, and metastasis. Without wishing to be limited by theory, it is believed that tyrosine kinases inhibitors of the present invention can ameliorate, abate, otherwise cause to be controlled, diseases associated with tyrosine kinases.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example, 1 to 6 carbon atoms or 1 to 4 carbon atoms. Designated numbers of carbon atoms (e.g., $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as ($C_{1-6}$ alkyl)$_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-yn-1-yl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. Examples of alkoxy groups include but are not limited to, ethoxy, isopropoxy and trifluoromethoxy groups.

The term "aryl," wherein used alone or as part of another group, is defined herein as an unsaturated, aromatic monocyclic ring of 6 carbon members or an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino)phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "aryloxy" refers to the group —O-aryl, wherein the aryl group is as defined above. Aryloxy groups optionally may be substituted. Examples of aryloxy groups include but are not limited to phenoxy, m-chlorophenoxy and 4-phenylphenoxy.

The term "arylalkyl" or "aralkyl" refers to the group -alkyl-aryl, where the alkyl and aryl groups are as defined herein. Arylalkyl groups of the present invention are optionally substituted. Examples of arylalkyl groups include, for example, benzyl, 1-phenylethyl, 2-phenylethyl, 3-phenylpropyl, 2-phenylpropyl, and fluorenylmethyl.

The term "arylalkynyl" or "aralkynyl" refers to the group -alkynyl-aryl, where the alkynyl and aryl groups are as defined herein. Arylalkynyl groups of the present invention are optionally substituted. Examples of arylalkynyl groups include, for example, ethynylbenzene, 1-methoxy-3-(prop-1-yn-1-yl)benzene, 1-chloro-4-(prop-1-yn-1-yl)benzene, 2-chloro-1-phenoxy-4-(prop-1-yn-1-yl)benzene 1-ethynylnaphthalene, prop-2-yn-1-ylbenzene (also propargylbenzene).

As used herein, trialkylsilyl whether used alone or as part of another group, refers to three alkyl groups attached to a silicon atom. The alkyl groups could be cycloalkyl, substituted or unsubstituted, branched or straight chains each containing 1-lo carbon atoms prederablt 1-6 carbon atoms. Nonlimiting examples of trialkylsilyl include t-butyl-dimethylsilyl, trimethylsilyl, diisopropylmethylsilyl.

As used herein, diarylalkylsilyl whether used alone or as part of another group, refers to two aryl groups and an alkyl group attached to a silicon atom. The aryl groups as defined here refers to unsaturated aromatic rings substituted or unsubstituted. The alkyl groups could be cycloalkyl, substituted or unsubstituted, branched or straight chains each containing 1-10 carbon atoms preferably 1-6 carbon atoms. Nonlimiting examples of diarylalkylsilyl include diphenylmethylsilyl, fluorenylmethyl silyl.

The terms "heterocyclic" and/or "heterocycle" and/or "heterocyclyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Nonlimiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, 2-aminobenzo[d]oxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxyquinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

The term "cycloalkylalkyl" refers to the group -alkyl-cycloalkyl, where the alkyl and cycloalkyl groups are as defined herein. Cycloalkylalkyl groups of the present invention are optionally substituted. Non-limiting examples of cycloalkylalkyl groups include, for example, 1-cylcohexylethyl, 2-cyclohexylethyl, 1-cyclohexylpropyl, cyclopropylmethyl, 2-cyclopentylpropyl, and the like.

The term "heterocyclylalkyl" refers to the group -alkyl-heterocyclyl, where the alkyl and heterocyclyl groups are defined as herein. Heterocyclylalkyl groups of the present invention are optionally substituted. Non-limiting examples of heterocyclylalkyl group include, for example, 3-(4-piperidinyl)-propyl, 2-(4-morpholinyl)ethyl, 3-(1-pyrrolidinyl) propyl, 4-(oxiranyl)butyl, 4-(2-aziridinyl)butyl, and the like.

The term "heteroarylalkyl" refers to the group -alkyl-heteroaryl, where the alkyl and heteroaryl groups are defined as herein. Heteroarylalkyl groups of the present invention are optionally substituted. Non-limiting examples of heteroarylalkyl groups include, for example, 3-(4-pyridyl)propyl, 3-(2-pyridyl)propyl, 2-(2-imidazolyl)ethyl, 4-(1-imidazolyl)butyl, 2-(2-pyrrolyl)ethyl, 5-(2-furanyl)pentyl, and the like. The term "alkoxyheteroarylalkyl" refers to the group -alkyl-heteroaryl-alkoxy, where the alkyl, heteroaryl, and alkoxy groups are defined herein. Alkoxyheteroarylalkyl groups of the present invention are optionally substituted. Non-limiting examples of alkoxyheteroarylalkyl include, for example, 3-(3-methoxy-4-pyridyl)propyl, 4-(2-methoxy-4-pyrimidinyl)butyl, 4-(4-ethoxythiopheneyl)butyl, 3-(6-propoxy-3-pyridinyl)propyl, and the like.

For the purposed of the present invention fused ring units, as well as spirocyclic rings, bicyclic rings and the like, which comprise a single heteroatom will be considered to belong to the cyclic family corresponding to the heteroatom containing ring.

Whenever a term or either of their prefix roots appears in a name of a substituent, the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^6$, —SR$^6$, —N(R$^6$)$_2$, —NR$^6$C(O)R$^6$, —SO$_2$R$^6$, —SO$_2$OR$^6$, —SO$_2$N(R$^6$)$_2$, —C(O)R$^6$, —C(O)OR$^6$, —C(O)N(R$^6$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, OXO, and R$^6$; wherein R$^6$, at each occurrence, independently is hydrogen, —OR$^7$, —SR$^7$, —C(O)R$^7$, —C(O)OR$^7$, —C(O)N(R$^7$)$_2$, —SO$_2$R$^7$, —S(O)$_2$OR$^7$, —N(R$^7$)$_2$, —NR$^7$C(O)R$^7$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^6$ units taken together with the atom(s) to which they are bound form an optionally substituted carbocycle or heterocycle wherein said carbocycle or heterocycle has 3 to 7 ring atoms; wherein R$^7$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^4$ units taken together with the atom(s) to which they are bound form an optionally substituted carbocycle or heterocycle wherein said carbocycle or heterocycle preferably has 3 to 7 ring atoms.

In some embodiments, the substituents are selected from where is R$^8$ i) —OR$^8$; for example, —OH, —OCH$_3$, —OCH$_2$CH$_3$, —OCH$_2$CH$_2$CH$_3$;

ii) —C(O)R$^8$; for example, —COCH$_3$, —COCH$_2$CH$_3$, —COCH$_2$CH$_2$CH$_3$;

iii) —C(O)OR$^8$; for example, —CO$_2$CH$_3$, —CO$_2$CH$_2$CH$_3$, —CO$_2$CH$_2$CH$_2$CH$_3$;

iv) —C(O)N(R$^8$)$_2$; for example, —CONH$_2$, —CONHCH$_3$, —CON(CH$_3$)$_2$;

v) —N(R$^8$)$_2$; for example, —NH$_2$, —NHCH$_3$, —N(CH$_3$)$_2$, —NH(CH$_2$CH$_3$);

vi) halogen: —F, —Cl, —Br, and —I;

vii) —CH$_e$X$_g$; wherein X is halogen; for example, —CH$_2$F, —CHF$_2$, —CF$_3$, —CCl$_3$, or —CBr$_3$;

viii) —SO$_2$R$^8$; for example, —SO$_2$H; —SO$_2$CH$_3$; —SO$_2$C$_6$H$_5$;

ix) $C_1$-$C_6$ linear, branched, or cyclic alkyl;

x) Cyano;

xi) Nitro;

xii) N(R$^8$)C(O)R$^8$;

xiii) Oxo (=O);

xiv) Heterocycle; and xv) Heteroaryl;

wherein each R$^8$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g., optionally substituted $C_3$-$C_4$ cycloalkyl); or two R$^8$ units can be taken together to form a ring comprising 3-7 ring atoms. In certain aspects, each R$^8$ is independently hydrogen, $C_1$-$C_6$ linear or branched alkyl optionally substituted with halogen or $C_3$-$C_6$ cycloalkyl.

At various places in the present specification, substituents of compounds are disclosed in groups or in ranges. It is specifically intended that the description include each and every individual sub-combination of the members of such groups and ranges. For example, the term "$C_{1-6}$ alkyl" is specifically intended to individually disclose $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$, alkyl.

For the purposes of the present invention, the terms "compound," "analog," and "composition of matter" stand equally well for the kinase inhibitors described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, chiral separation by HPLC, simulated moving bed chromatography (SMB), and asymmetric synthesis. The present teachings also encompass cis and trans isomers (Z and E) of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, $LiOH$, $NaOH$, $KOH$, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^4)_2$, each $R^4$ may be the same or different than the other). Combinations of substituents and/or variables are permissible only if such combinations result in stable compounds.

As used herein, the term "polar protic solvent" refers to a solvent which has O—H or N—H bonds that can participate in hydrogen bonding intermolecularly. These solvents can serve as a source of proton and have high dielectric constants and high dipole moments. Examples of polar protic solvents include ammonia, water, methanol, ethanol, n-propanol, t-butanol, and acetic acid.

As used herein, the term "polar aprotic solvent" refers to a solvent which is a polar solvent with high dielectric and dipole moments but it does not participate in hydrogen bonding. Examples of polar aprotic solvents include tetrahydrofuran, ethyl acetate, dichloromethane, acetone, N,N-dimethylformamide, acetonitrile, and dimethyl sulfoxide.

As used herein, the term "oxidizing agent" refers to a substance that oxidizes other substances. An oxidizing agent gives oxygen to another substance. An oxidizing agent takes electrons from other substances and by doing so, it gains electrons. Examples of oxidizing agents include m-chloroperoxybenzoic acid, monoperphthalic acid, peracetic acid, perpropionic acid, pertrifluoroacetic acid, potassium periodate, sodium metaperiodate, sodium perborate, potassium peroxymonosulfate (Oxone®), potassium peroxydisulfate, dimethyldioxirane, diphenyl sulfoxide, dimethyl sulfoxide, urea hydrogen peroxide complex in the presence of a rhenium catalyst such as $ReOCl_3(PPh_3)_2$, an oxidoreductase such as Baeyer-Villiger monooxygenase, cytochrome P450 2C9, cytochrome P450 2C19, and cytochrome P450 3A4 hydrogen peroxide in the presence titanium (IV) isopropoxide-diethyltartarate. An oxidizing agent could also oxidize substances electrochemically or photochemically.

As used herein the term "modulation" refers to modification, alteration, inhibition, regulation, activation or stimulation of the activity of a kinase protein.

As used herein the term "organic bases" refers to an organic compound which acts as a base by accepting a proton. Typically, organic bases contain nitrogen atoms such as alkylamines or aromatic amines that can donate electrons. Examples of organic bases include, ammonia, ammonium hydroxide, methylamine, trimethylamine, diisopropylethylamine, trimethylamine, 2-methylpicoline, 4-dimethylaminopyridine, dimethylaniline.

As used herein, the term "inorganic bases" refers to a compound that contains a metal and can accept a proton or alternatively donate a negative species such as a pair of electrons or oxide ion. Examples of inorganic bases include potassium carbonate, cesium carbonate, lithium carbonate, sodium carbonate, sodium hydroxide, magnesium hydroxide, lithium hydroxide, cesium hydroxide, rubidium hydroxide, sodium amide, lithium amide, potassium amide, magnesium oxide, calcium oxide, stronthium oxide, barium oxide, scandium oxide.

As used herein, the terms "treat" and "treating" and "treatment" refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

EMBODIMENTS OF THE INVENTION

The kinase inhibitors of the present invention include all enantiomeric and diastereomeric forms and pharmaceutically accepted salts thereof having the formula (I):

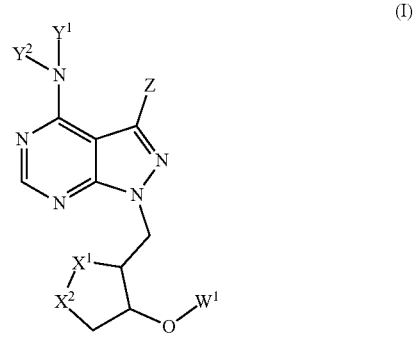

wherein:

$W^1$ is selected from a group consisting of hydrogen, $C_{1-6}$ alkyl, $C_{3-7}$ cycloalkyl, cycloalkylalkyl, aryl, arylalkyl, heterocycl, heterocycyclalkyl, heteroaryl, heteroarylalkyl, alkoxyheteroarylalkyl, $C(O)R^1$, $C(O)R^2$, $C(O)OR^1$, $C(O)OR^2$, trialkylsilyl and diarylalkylsilyl, $X^1$ and $X^2$ are at each occurrence selected from the group consisting of S, SO and $SO_2$, $Y^1$ and $Y^2$ are at each occurrence selected from the group consisting of hydrogen, $C_{1-6}$ alkyl, $C(O)R^1$, $C(O)R^2$, $C(O)OR^1$, and $C(O)OR^2$, Z is selected from the group consisting of hydrogen, $C_{1-6}$ alkyl $C_{1-6}$ alkenyl, $C_{1-6}$ alkynyl, arylalkynyl, halogen, $C(O)R^1$, $C(O)R^2$, $C(O)OR^1$, $C(O)OR^2$,

[Structure: isoxazole with $R^3$ substituent]

, [Structure: benzoxazole-2-amine with $R^{4a}$, $R^{4b}$, $R^{4c}$ substituents] and

[Structure: phenyl with $R^{5a}$, $R^{5b}$, $R^{5c}$, $R^{5d}$, $R^{5e}$ substituents];

$R^1$ is selected from the group of hydrogen, $C_{1-6}$ alkyl and $C_{1-6}$ alkenyl, $R^2$ is selected from the group of hydrogen, aryl, heteroaryl, arylalkyl, heteroarylalkyl, $R^3$ is selected from the group of hydrogen, $C_{1-6}$ alkyl, $C_{3-7}$ cycloalkyl, cycloalkylalkyl, aryl, arylalkyl, heteroaryl and halogen, $R^{4a}$, $R^{4b}$, and $R^{4c}$ are each independently selected from the group of hydrogen, $C_{1-6}$ alkyl, $C_{1-6}$ haloalkyl, $C_{1-6}$ alkoxy, heterocyclyl, heterocyclylalkyl, aryl, arylalkyl, aryloxy, heteroaryl, heteroarylalkyl and alkoxyheteroarylalkyl, $R^{5a}$, $R^{5b}$, $R^{5c}$, $R^{5d}$ and $R^{5e}$ are each independently selected from the group of hydrogen, $C_{1-6}$ alkyl, $C_{1-6}$ alkenyl, $C_{1-6}$ alkynyl, $C_{1-6}$ haloalkyl, $C_{1-6}$ alkoxy, $C_{3-7}$ cycloalkyl, cycloalkylalkyl, heterocyclyl, heterocyclylalkyl, aryl, arylalkyl, aryloxy, arylalkynyl, heteroaryl, heteroarylalkyl and alkoxyheteroarylalkyl, including enantiomers, diastereomers, hydrates, solvates, pharmaceutically acceptable salts, prodrugs and complexes thereof.

The compounds of the present invention include compounds where $X^1$ and $X^2$ are at each occurrence selected to be S, and $Y^1$ and $Y^2$ are H, including enantiomers, diastereomers, hydrates, solvates, pharmaceutically acceptable salts, prodrugs and complexes thereof.

The compounds of the present invention include compounds where $X^1$ and $X^2$ are at each occurrence selected to be S, and $Y^1$ and $Y^2$ are H, and Z is the moiety phenyl with $R^{5a}$, $R^{5b}$, $R^{5c}$, $R^{5d}$, $R^{5e}$, including enantiomers, diastereomers, hydrates, solvates, pharmaceutically acceptable salts, prodrugs and complexes thereof.

In some embodiments $W^1$ is hydrogen.
In some embodiments $W^1$ is optionally substituted $C_{1-6}$ alkyl.
In some embodiments $W^1$ is optionally substituted $C_{3-7}$ cycloalkyl.
In some embodiments $W^1$ is optionally substituted cycloalkylalkyl.
In some embodiments $W^1$ is optionally substituted aryl.
In some embodiments $W^1$ is optionally substituted arylalkyl.
In some embodiments $W^1$ is optionally substituted heterocycl.
In some embodiments $W^1$ is optionally substituted heterocycloalkyl.
In some embodiments $W^1$ is optionally substituted heteroaryl.
In some embodiments $W^1$ is optionally substituted heteroarylalkyl.
In some embodiments $W^1$ is optionally substituted alkoxyheteroarylalkyl.
In some embodiments $W^1$ is $C(O)R^1$.
In some embodiments $W^1$ is $C(O)R^2$.
In some embodiments $W^1$ is $C(O)OR^1$.
In some embodiments $W^1$ is $C(O)OR^2$.
In some embodiments $W^1$ is trialkylsilyl.
In some embodiments $W^1$ is diarylalkylsilyl.
In some embodiments $X^1$ is S.
In some embodiments $X^1$ is SO.
In some embodiments $X^1$ is $SO_2$.
In some embodiments $X^2$ is S.
In some embodiments $X^2$ is SO.
In some embodiments $X^2$ is $SO_2$.
In some embodiments $Y^1$ is hydrogen.
In some embodiments $Y^1$ is optionally substituted $C_{1-6}$ alkyl.
In some embodiments $Y^1$ is $C(O)R^1$.
In some embodiments $Y^1$ is $C(O)R^2$.
In some embodiments $Y^1$ is $C(O)OR^1$.
In some embodiments $Y^1$ is $C(O)OR^2$.
In some embodiments $Y^2$ is hydrogen.
In some embodiments $Y^2$ is optionally substituted $C_{1-6}$ alkyl.
In some embodiments $Y^2$ is $C(O)R^1$.
In some embodiments $Y^2$ is $C(O)R^2$.
In some embodiments $Y^2$ is $C(O)OR^1$.
In some embodiments $Y^2$ is $C(O)OR^2$.
In some embodiments Z is hydrogen.
In some embodiments Z is optionally substituted $C_{1-6}$ alkyl.
In some embodiments Z is optionally substituted $C_{1-6}$ alkenyl.
In some embodiments Z is optionally substituted $C_{1-6}$ alkynyl.
In some embodiments Z is optionally substituted arylalkynyl.
In some embodiments Z is halogen.
In some embodiments Z is $C(O)R^1$.
In some embodiments Z is $C(O)R^2$.
In some embodiments Z is $C(O)OR^1$.
In some embodiments Z is $C(O)OR^2$.

In preferred embodiments Z is

[Structure: isoxazole with $R^3$ substituent]

In preferred embodiments Z is

[Structure: benzoxazole-2-amine with $R^{4a}$, $R^{4b}$, $R^{4c}$ substituents]

In preferred embodiments Z is $$\begin{array}{c} R^{5b} \\ R^{5a} \diagup \diagdown R^{5c} \\ \xi \diagdown \diagup R^{5d} \\ R^{5e} \end{array}$$

In some embodiments $R^1$ is hydrogen.
In some embodiments $R^1$ is optionally substituted $C_{1-6}$ alkyl.
In some embodiments $R^1$ is optionally substituted $C_{1-6}$ alkenyl.
In some embodiments $R^2$ is hydrogen.
In some embodiments $R^2$ is optionally substituted aryl.
In some embodiments $R^2$ is optionally substituted heteroaryl.
In some embodiments $R^2$ is optionally substituted arylalkyl.
In some embodiments $R^2$ is optionally substituted heteroarylalkyl.
In some embodiments $R^3$ is hydrogen.
In some embodiments $R^3$ is optionally substituted $C_{1-6}$ alkyl.
In some embodiments $R^3$ is optionally substituted $C_{3-7}$ cycloalkyl.
In some embodiments $R^3$ is optionally substituted cycloalkylalkyl.
In some embodiments $R^3$ is optionally substituted aryl.
In some embodiments $R^3$ is optionally substituted arylalkyl.
In some embodiments $R^3$ is optionally substituted heteroaryl.
In some embodiments $R^3$ is halogen.
In some embodiments $R^{4a}$ is hydrogen.
In some embodiments $R^{4a}$ is optionally substituted $C_{1-6}$ alkyl.
In some embodiments $R^{4a}$ is optionally substituted $C_{1-6}$ haloalkyl.
In some embodiments $R^{4a}$ is optionally substituted $C_{1-6}$ alkoxy.
In some embodiments $R^{4a}$ is optionally substituted heterocyclyl.
In some embodiments $R^{4a}$ is optionally substituted heterocyclylalkyl.
In some embodiments $R^{4a}$ is optionally substituted aryl.
In some embodiments $R^{4a}$ is optionally substituted arylalkyl.
In some embodiments $R^{4a}$ is optionally substituted aryloxy.
In some embodiments $R^{4a}$ is optionally substituted heteroaryl.
In some embodiments $R^{4a}$ is optionally substituted heteroarylalkyl.
In some embodiments $R^{4a}$ is optionally substituted alkoxyheteroarylalkyl.
In some embodiments $R^{4b}$ is hydrogen.
In some embodiments $R^{4b}$ is optionally substituted $C_{1-6}$ alkyl.
In some embodiments $R^{4b}$ is optionally substituted $C_{1-6}$ haloalkyl.
In some embodiments $R^{4b}$ is optionally substituted $C_{1-6}$ alkoxy.
In some embodiments $R^{4b}$ is optionally substituted heterocyclyl.
In some embodiments $R^{4b}$ is optionally substituted heterocyclylalkyl.
In some embodiments $R^{4b}$ is optionally substituted aryl.
In some embodiments $R^{4b}$ is optionally substituted arylalkyl.
In some embodiments $R^{4b}$ is optionally substituted aryloxy.
In some embodiments $R^{4b}$ is optionally substituted heteroaryl.
In some embodiments $R^{4b}$ is optionally substituted heteroarylalkyl.
In some embodiments $R^{4b}$ is optionally substituted alkoxyheteroarylalkyl.
In some embodiments $R^{4c}$ is hydrogen.
In some embodiments $R^{4c}$ is optionally substituted $C_{1-6}$ alkyl.
In some embodiments $R^{4c}$ is optionally substituted $C_{1-6}$ haloalkyl.
In some embodiments $R^{4c}$ is optionally substituted $C_{1-6}$ alkoxy.
In some embodiments $R^{4c}$ is optionally substituted heterocyclyl.
In some embodiments $R^{4c}$ is optionally substituted heterocyclylalkyl.
In some embodiments $R^{4c}$ is optionally substituted aryl.
In some embodiments $R^{4c}$ is optionally substituted arylalkyl.
In some embodiments $R^{4c}$ is optionally substituted aryloxy.
In some embodiments $R^{4c}$ is optionally substituted heteroaryl.
In some embodiments $R^{4c}$ is optionally substituted heteroarylalkyl.
In some embodiments $R^{4c}$ is optionally substituted alkoxyheteroarylalkyl.
In some embodiments $R^{5a}$ is hydrogen.
In some embodiments $R^{5a}$ is optionally substituted $C_{1-6}$ alkyl.
In some embodiments $R^{5a}$ is optionally substituted $C_{1-6}$ alkenyl.
In some embodiments $R^{5a}$ is optionally substituted $C_{1-6}$ alkynyl.
In some embodiments $R^{5a}$ is optionally substituted $C_{1-6}$ haloalkyl.
In some embodiments $R^{5a}$ is optionally substituted $C_{1-6}$ alkoxy.
In some embodiments $R^{5a}$ is optionally substituted $C_{3-7}$ cycloalkyl.
In some embodiments $R^{5a}$ is optionally substituted cycloalkylalkyl.
In some embodiments $R^{5a}$ is optionally substituted heterocyclyl.
In some embodiments $R^{5a}$ is optionally substituted heterocyclylalkyl.
In some embodiments $R^{5a}$ is optionally substituted aryl.
In some embodiments $R^{5a}$ is optionally substituted arylalkyl.
In some embodiments $R^{5a}$ is optionally substituted aryloxy.
In some embodiments $R^{5a}$ is optionally substituted arylalkynyl.
In some embodiments $R^{5a}$ is optionally substituted heteroaryl.
In some embodiments $R^{5a}$ is optionally substituted heteroarylalkyl.
In some embodiments $R^{5a}$ optionally substituted alkoxyheteroarylalkyl.
In some embodiments $R^{5b}$ is hydrogen.
In some embodiments $R^{5b}$ is optionally substituted $C_{1-6}$ alkyl.
In some embodiments $R^{5b}$ is optionally substituted $C_{1-6}$ alkenyl.
In some embodiments $R^{5b}$ is optionally substituted $C_{1-6}$ alkynyl.
In some embodiments $R^{5b}$ is optionally substituted $C_{1-6}$ haloalkyl.

In some embodiments $R^{5b}$ is optionally substituted $C_{1-6}$ alkoxy.
In some embodiments $R^{5b}$ is optionally substituted $C_{3-7}$ cycloalkyl.
In some embodiments $R^{5b}$ is optionally substituted cycloalkylalkyl.
In some embodiments $R^{5b}$ is optionally substituted heterocyclyl.
In some embodiments $R^{5b}$ is optionally substituted heterocyclylalkyl.
In some embodiments $R^{5b}$ is optionally substituted aryl.
In some embodiments $R^{5b}$ is optionally substituted arylalkyl.
In some embodiments $R^{5b}$ is optionally substituted aryloxy.
In some embodiments $R^{5b}$ is optionally substituted arylalkynyl.
In some embodiments $R^{5b}$ is optionally substituted heteroaryl.
In some embodiments $R^{5b}$ is optionally substituted heteroarylalkyl.
In some embodiments $R^{5b}$ optionally substituted alkoxyheteroarylalkyl.
In some embodiments $R^{5c}$ is hydrogen.
In some embodiments $R^{5c}$ is optionally substituted $C_{1-6}$ alkyl.
In some embodiments $R^{5c}$ is optionally substituted $C_{1-6}$ alkenyl.
In some embodiments $R^{5c}$ is optionally substituted $C_{1-6}$ alkynyl.
In some embodiments $R^{5c}$ is optionally substituted $C_{1-6}$ haloalkyl.
In some embodiments $R^{5c}$ is optionally substituted $C_{1-6}$ alkoxy.
In some embodiments $R^{5c}$ is optionally substituted $C_{3-7}$ cycloalkyl.
In some embodiments $R^{5c}$ is optionally substituted cycloalkylalkyl.
In some embodiments $R^{5c}$ is optionally substituted heterocyclyl.
In some embodiments $R^{5c}$ is optionally substituted heterocyclylalkyl.
In some embodiments $R^{5c}$ is optionally substituted aryl.
In some embodiments $R^{5c}$ is optionally substituted arylalkyl.
In some embodiments $R^{5c}$ is optionally substituted aryloxy.
In some embodiments $R^{5c}$ is optionally substituted arylalkynyl.
In some embodiments $R^{5c}$ is optionally substituted heteroaryl.
In some embodiments $R^{5c}$ is optionally substituted heteroarylalkyl.
In some embodiments $R^{5c}$ optionally substituted alkoxyheteroarylalkyl.
In some embodiments $R^{5d}$ is hydrogen.
In some embodiments $R^{5d}$ is optionally substituted $C_{1-6}$ alkyl.
In some embodiments $R^{5d}$ is optionally substituted $C_{1-6}$ alkenyl.
In some embodiments $R^{5d}$ is optionally substituted $C_{1-6}$ alkynyl.
In some embodiments $R^{5d}$ is optionally substituted $C_{1-6}$ haloalkyl.
In some embodiments $R^{5d}$ is optionally substituted $C_{1-6}$ alkoxy.
In some embodiments $R^{5d}$ is optionally substituted $C_{3-7}$ cycloalkyl.
In some embodiments $R^{5d}$ is optionally substituted cycloalkylalkyl.
In some embodiments $R^{5d}$ is optionally substituted heterocyclyl.
In some embodiments $R^{5d}$ is optionally substituted heterocyclylalkyl.
In some embodiments $R^{5d}$ is optionally substituted aryl.
In some embodiments $R^{5d}$ is optionally substituted arylalkyl.
In some embodiments $R^{5d}$ is optionally substituted aryloxy.
In some embodiments $R^{5d}$ is optionally substituted arylalkynyl.
In some embodiments $R^{5d}$ is optionally substituted heteroaryl.
In some embodiments $R^{5d}$ is optionally substituted heteroarylalkyl.
In some embodiments $R^{5d}$ optionally substituted alkoxyheteroarylalkyl.
In some embodiments $R^{5e}$ is hydrogen.
In some embodiments $R^{5e}$ is optionally substituted $C_{1-6}$ alkyl.
In some embodiments $R^{5e}$ is optionally substituted $C_{1-6}$ alkenyl.
In some embodiments $R^{5e}$ is optionally substituted $C_{1-6}$ alkynyl.
In some embodiments $R^{5e}$ is optionally substituted $C_{1-6}$ haloalkyl.
In some embodiments $R^{5e}$ is optionally substituted $C_{1-6}$ alkoxy.
In some embodiments $R^{5e}$ is optionally substituted $C_{3-7}$ cycloalkyl.
In some embodiments $R^{5e}$ is optionally substituted cycloalkylalkyl.
In some embodiments $R^{5e}$ is optionally substituted heterocyclyl.
In some embodiments $R^{5e}$ is optionally substituted heterocyclylalkyl.
In some embodiments $R^{5e}$ is optionally substituted aryl.
In some embodiments $R^{5e}$ is optionally substituted arylalkyl.
In some embodiments $R^{5e}$ is optionally substituted aryloxy.
In some embodiments $R^{5e}$ is optionally substituted arylalkynyl.
In some embodiments $R^{5e}$ is optionally substituted heteroaryl.
In some embodiments $R^{5e}$ is optionally substituted heteroarylalkyl.
In some embodiments $R^{5e}$ optionally substituted alkoxyheteroarylalkyl.

Exemplary embodiments include compounds having the formula (I) or an enantiomer, diastereomer, hydrate, solvate, prodrug, complex, or pharmaceutically acceptable salt form thereof wherein $Y^1$ is H, and Z is

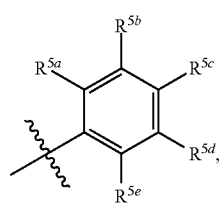

wherein $R^{5a}$, $R^{5b}$, $R^{5d}$, and $R^{5e}$ are all H, and wherein non-limiting examples of $X^1$, $X^2$, $Y^2$, $R^{5c}$ and $W^1$ are defined herein below in Table 1.

TABLE 1

Exemplary compounds of the formula (I)

| Group Number | $X^1$ | $X^2$ | $Y^2$ | $R^{5c}$ | $W^1$ |
|---|---|---|---|---|---|
| 1 | S | SO | H | OPhenyl | H |
| 2 | SO | S | H | OPhenyl | H |
| 3 | S | SO | H | OPhenyl | $CH_3$ |
| 4 | SO | S | H | OPhenyl | $CH_3$ |
| 5 | S | SO | $CO_2$-t-Butyl | OPhenyl | H |
| 6 | SO | S | $CO_2$-t-Butyl | OPhenyl | H |
| 7 | S | SO | $CO_2$-t-Butyl | OPhenyl | $CH_3$ |
| 8 | SO | S | $CO_2$-t-Butyl | OPhenyl | $CH_3$ |
| 9 | S | SO | $COCH_3$ | OPhenyl | $CO_2$—$CH_3$ |
| 10 | SO | S | $COCH_3$ | OPhenyl | $CO_2$—$CH_3$ |
| 11 | S | SO | H | $OCH_3$ | H |
| 12 | SO | S | H | $OCH_3$ | H |
| 13 | S | SO | H | $OCH_3$ | $CH_3$ |
| 14 | SO | S | H | $OCH_3$ | $CH_3$ |
| 15 | SO | SO | H | OPhenyl | H |
| 16 | SO | SO | H | $OCH_3$ | H |

Exemplary embodiments include compounds having formula (I) or an enantiomer, diastereomer, hydrate, solvate, prodrug, complex, or pharmaceutically acceptable salt form thereof: wherein $Y^1$ is H, and Z is

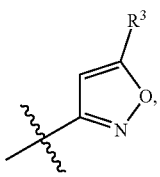

and wherein non-limiting examples of $X^1$, $X^2$, $Y^2$, $R^3$ and $W^1$ are defined herein below in Table 2.

TABLE 2

Exemplary compounds of the formula (I)

| Group Number | $X^1$ | $X^2$ | $Y^2$ | $R^3$ | $W^1$ |
|---|---|---|---|---|---|
| 1 | S | SO | H | Phenyl | H |
| 2 | SO | S | H | Phenyl | H |
| 3 | S | SO | H | $CH_2$Phenyl | $CH_3$ |
| 4 | SO | S | H | $CH_2$Phenyl | $CH_3$ |
| 5 | S | SO | $CO_2$-t-Butyl | c-propyl | H |
| 6 | SO | S | $CO_2$-t-Butyl | c-propyl | H |
| 7 | S | SO | $CO_2$-t-Butyl | c-propyl | $CH_3$ |
| 8 | SO | S | $CO_2$-t-Butyl | c-propyl | $CH_3$ |
| 9 | S | SO | $COCH_3$ | c-propyl | c-pentyl |
| 10 | SO | S | $COCH_3$ | c-propyl | c-pentyl |
| 11 | S | SO | H | c-butyl | $CH_3$ |
| 12 | SO | S | H | c-butyl | $CH_3$ |
| 13 | S | SO | H | Br | $CH_3$ |
| 14 | SO | S | H | Br | $CH_3$ |
| 15 | S | SO | H | i-propyl | H |
| 16 | SO | S | H | i-propyl | H |

Exemplary embodiments include compounds having formula (I) or an enantiomer, diastereomer, hydrate, solvate, prodrug, complex, or pharmaceutically acceptable salt form thereof: wherein $Y^1$ is H, and Z is

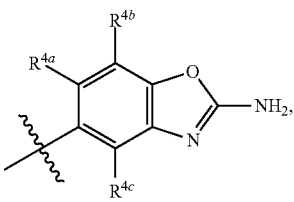

wherein $R^{4a}$ and $R^{4c}$ are H, and wherein non-limiting examples where $X^1$, $X^2$, $Y^2$, $R^{4b}$ or $W^1$ are defined herein below in Table 3.

TABLE 3

Exemplary compounds of the formula (I)

| Group Number | $X^1$ | $X^2$ | $Y^2$ | $R^{4b}$ | $W^1$ |
|---|---|---|---|---|---|
| 1 | S | SO | H | Cl | H |
| 2 | SO | S | H | Cl | H |
| 3 | S | SO | H | F | $CH_3$ |
| 4 | SO | S | H | F | $CH_3$ |
| 5 | S | SO | $CO_2$-t-Butyl | $OCH_3$ | H |
| 6 | SO | S | $CO_2$-t-Butyl | $OCH_3$ | H |
| 7 | S | SO | $CO_2$-t-Butyl | F | $CH_3$ |
| 8 | SO | S | $CO_2$-t-Butyl | F | $CH_3$ |
| 9 | S | SO | $COCH_3$ | c-propyl | c-pentyl |
| 10 | SO | S | $COCH_3$ | c-propyl | c-pentyl |
| 11 | S | SO | H | H | $CH_3$ |
| 12 | SO | S | H | H | $CH_3$ |
| 13 | S | SO | H | H | Ph |
| 14 | SO | S | H | H | Ph |
| 15 | S | SO | H | F | H |
| 16 | SO | S | H | F | H |

Exemplary embodiments include compounds having the formula (I) or an enantiomer, diastereomer, hydrate, solvate, prodrug, complex, or pharmaceutically acceptable salt form thereof wherein $Y^1$ is H, and Z is ethynylbenzene, and wherein non-limiting examples of $X^1$, $X^2$, $Y^2$, and $W^1$ are defined herein below in Table 4.

TABLE 4

Exemplary compounds of the formula (I)

| Group Number | $X^1$ | $X^2$ | $Y^2$ | $W^1$ |
|---|---|---|---|---|
| 1 | S | SO | H | H |
| 2 | SO | S | H | H |
| 3 | S | SO | H | $CH_3$ |
| 4 | SO | S | H | $CH_3$ |
| 5 | S | SO | $CO_2$-t-Butyl | H |
| 6 | SO | S | $CO_2$-t-Butyl | H |
| 7 | S | SO | $CO_2$-t-Butyl | $CH_3$ |
| 8 | SO | S | $CO_2$-t-Butyl | $CH_3$ |
| 9 | S | SO | $COCH_3$ | $CO_2$—$CH_3$ |
| 10 | SO | S | $COCH_3$ | $CO_2$—$CH_3$ |
| 11 | S | SO | H | c-pentyl |
| 12 | SO | S | H | c-pentyl |
| 13 | S | SO | H | c-propyl |
| 14 | SO | S | H | c-propyl |
| 15 | S | SO | H | $CH_2$Phenyl |
| 16 | SO | S | H | $CH_2$Phenyl |

For the purposes of demonstrating the manner in which the compounds of the present invention are named and referred to herein, bonds between two different substituents one of which being in a heterocycle are represented by plain lines (———) to denote above the plane as a mixture of both enantiomers and a dashed line (------) to denote bonds pointing downward as a mixture of enantiomers. Bonds to atoms above the plane of the drawing denoting absolute stereochemistry are represented by (—■). Bonds below the plane of the drawing denoting absolute stereochemistry are represented by (""""""). A wavy line denotes situations where the stereochemistry is unknown (∿).

For the purposes of demonstrating the manner in which the compounds of the present invention are named and referred to herein, the compound having the formula:

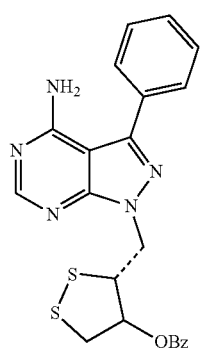

has the chemical name trans 3-((4-amino-3-phenyl-1H-pyrazolo[3,4-d]pyrimidin-1-yl)methyl)-1,2-dithiolan-4-yl benzoate).

For the purposes of demonstrating the manner in which the compounds of the present invention are named and referred to herein, the compound having the formula:

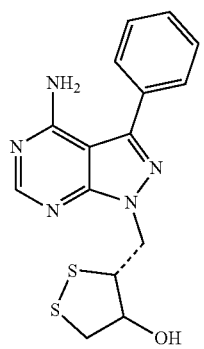

has the chemical name trans 3-((4-amino-3-phenyl-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

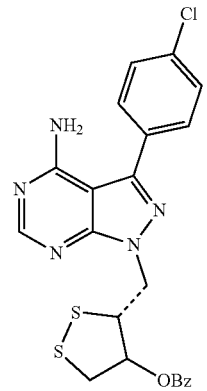

has the chemical name trans 3-((4-amino-3-(4-chlorophenyl)-1H-pyrazolo[3,4-d]pyrimidin-1-yl)methyl)-1,2-dithiolan-4-yl benzoate.

For the purposes of demonstrating the manner in which the compounds of the present invention are named and referred to herein, the compound having the formula:

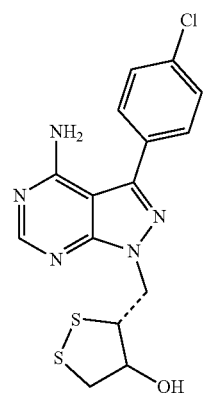

has the chemical name trans 3-((4-amino-3-(4-chlorophenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

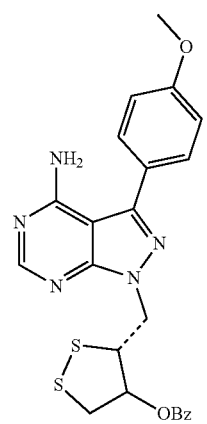

has the chemical name trans 3-((4-amino-3-(4-methoxyphenyl)-1H-pyrazolo[3,4-d]pyrimidin-1-yl)methyl)-1,2-dithiolan-4-yl benzoate.

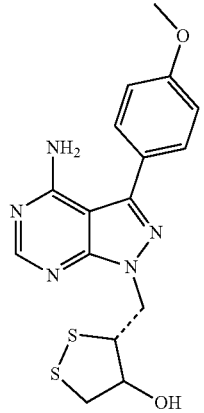

has the chemical name trans 3-((4-amino-3-(4-methoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

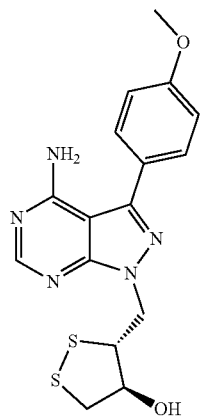

has the chemical name (3R,4S)-3-((4-amino-3-(4-methoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

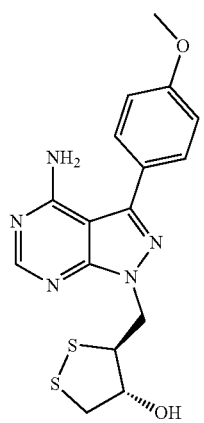 [SMILES: COc1ccc(-c2nn(C[C@@H]3SSC[C@H]3O)c3ncnc(N)c23)cc1]

has the chemical name (3S,4R)-3-((4-amino-3-(4-methoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

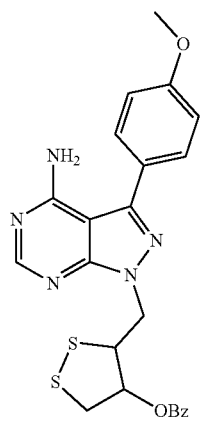

has the chemical name cis 3-((4-amino-3-(4-methoxyphenyl)-1H-pyrazolo[3,4-d]pyrimidin-1-yl)methyl)-1,2-dithiolan-4-yl benzoate.

For the purposes of demonstrating the manner in which the compounds of the present invention are named and referred to herein, the compound having the formula:

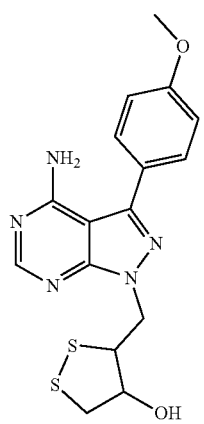 [SMILES: COc1ccc(-c2nn(CC3SSCC3O)c3ncnc(N)c23)cc1]

has the chemical name cis 3-((4-amino-3-(4-methoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

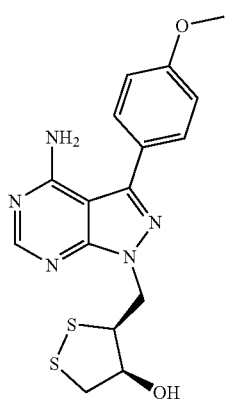 [SMILES: COc1ccc(-c2nn(C[C@@H]3SSC[C@@H]3O)c3ncnc(N)c23)cc1]

has the chemical name (3S,4S)-3-((4-amino-3-(4-methoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

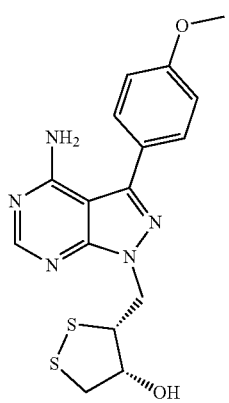 [SMILES: COc1ccc(-c2nn(C[C@H]3SSC[C@H]3O)c3ncnc(N)c23)cc1]

has the chemical name (3R,4R)-3-((4-amino-3-(4-methoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

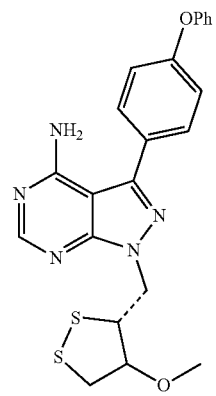

has the chemical name trans 1-((4-methoxy-1,2-dithiolan-3-yl)methyl)-3-(4-phenoxyphenyl)-1H-pyrazolo[3,4-d]pyrimidin-4-amine.

For the purposes of demonstrating the manner in which the compounds of the present invention are named and referred to herein, the compound having the formula:

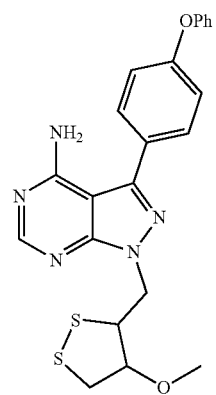 [SMILES: COC1CSSC1Cn1nc(-c2ccc(Oc3ccccc3)cc2)c2c(N)ncnc21]

has the chemical name cis 1-((4-methoxy-1,2-dithiolan-3-yl)methyl)-3-(4-phenoxyphenyl)-1H-pyrazolo[3,4-d]pyrimidin-4-amine.

For the purposes of demonstrating the manner in which the compounds of the present invention are named and referred to herein, the compound having the formula:

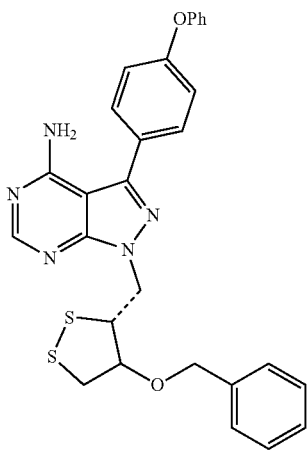

has the chemical name trans 1-((4-(benzyloxy)-1,2-dithiolan-3-yl)methyl)-3-(4-phenoxyphenyl)-1H-pyrazolo[3,4-d]pyrimidin-4-amine.

For the purposes of demonstrating the manner in which the compounds of the present invention are named and referred to herein, the compound having the formula:

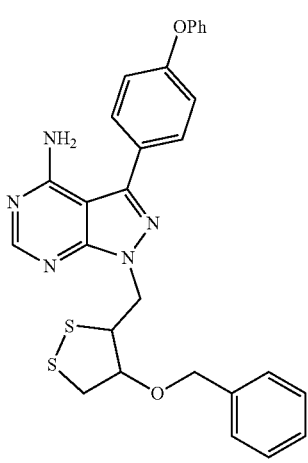 [SMILES: Nc1ncnc2c1c(-c1ccc(Oc3ccccc3)cc1)nn2CC1SSCC1OCc1ccccc1]

has the chemical name cis 1-((4-(benzyloxy)-1,2-dithiolan-3-yl)methyl)-3-(4-phenoxyphenyl)-1H-pyrazolo[3,4-d]pyrimidin-4-amine.

For the purposes of demonstrating the manner in which the compounds of the present invention are named and referred to herein, the compound having the formula:

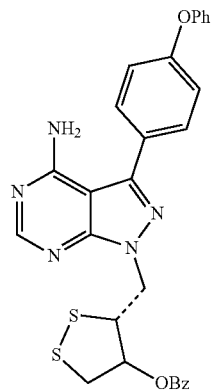

has the chemical name trans 3-((4-amino-3-(4-phenoxyphenyl)-1H-pyrazolo[3,4-d]pyrimidin-1-yl)methyl)-1,2-dithiolan-4-yl benzoate.

For the purposes of demonstrating the manner in which the compounds of the present invention are named and referred to herein, the compound having the formula:

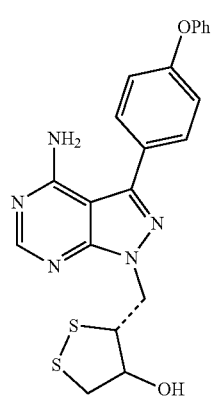

has the chemical name trans 3-((4-amino-3-(4-phenoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

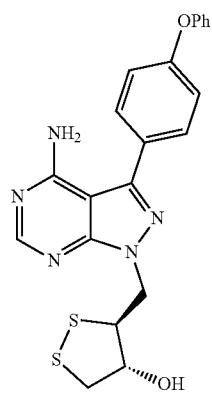 [SMILES: Nc1ncnc2c1c(-c1ccc(Oc3ccccc3)cc1)nn2C[C@@H]1SSC[C@H]1O]

has the chemical name (3S,4R)-3-((4-amino-3-(4-phenoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

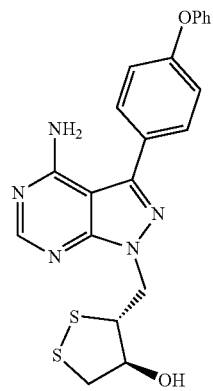 [SMILES: Nc1ncnc2c1c(-c1ccc(Oc3ccccc3)cc1)nn2C[C@H]1SSC[C@@H]1O]

has the chemical name (3R,4S)-3-((4-amino-3-(4-phenoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

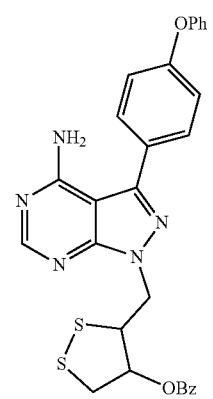

has the chemical name cis 3-((4-amino-3-(4-phenoxyphenyl)-1H-pyrazolo[3,4-d]pyrimidin-1-yl)methyl)-1,2-dithiolan-4-yl benzoate.

For the purposes of demonstrating the manner in which the compounds of the present invention are named and referred to herein, the compound having the formula:

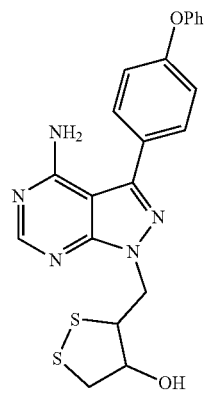 [SMILES: Nc1ncnc2c1c(-c1ccc(Oc3ccccc3)cc1)nn2CC1SSCC1O]

has the chemical name cis 3-((4-amino-3-(4-phenoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

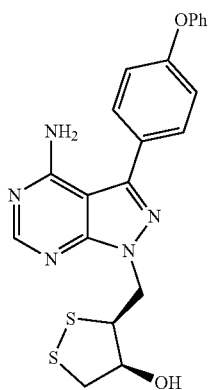 [SMILES: Nc1ncnc2c1c(-c1ccc(Oc3ccccc3)cc1)nn2C[C@@H]1SSC[C@@H]1O]

has the chemical name (3S,4S)-3-((4-amino-3-(4-phenoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

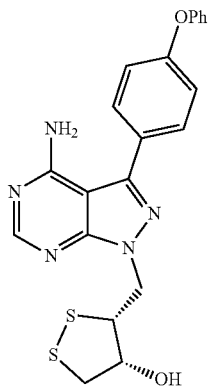 [SMILES: Nc1ncnc2c1c(-c1ccc(Oc3ccccc3)cc1)nn2C[C@H]1SSC[C@H]1O]

has the chemical name (3R,4R)-3-((4-amino-3-(4-phenoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

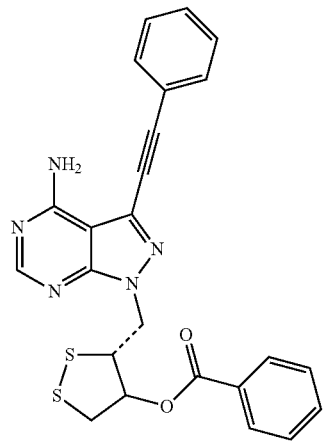

has the chemical name trans 3-((4-amino-3-(phenylethynyl)-1H-pyrazolo[3,4-d]pyrimidin-1-yl)methyl-1,2-dithiolan-4-yl benzoate.

For the purposes of demonstrating the manner in which the compounds of the present invention are named and referred to herein, the compound having the formula:

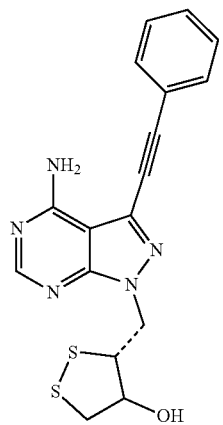

has the chemical name trans 3-(4-amino-3-(phenylethynyl)-1H-pyrazolo[3,4-d]pyrimidin-1-yl)methyl-1,2-dithiolan-4-ol.

For the purposes of demonstrating the manner in which the compounds of the present invention are named and referred to herein, the compound having the formula:

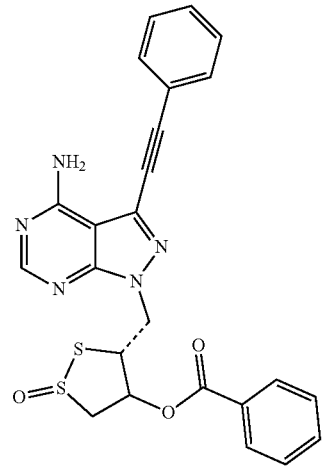

has the chemical name trans 3-((4-amino-3-(phenylethynyl)-1H-pyrazolo[3,4-d]pyrimidin-1-yl)methyl-1-oxido-1,2-dithiolan-4-yl benzoate.

For the purposes of demonstrating the manner in which the compounds of the present invention are named and referred to herein, the compound having the formula:

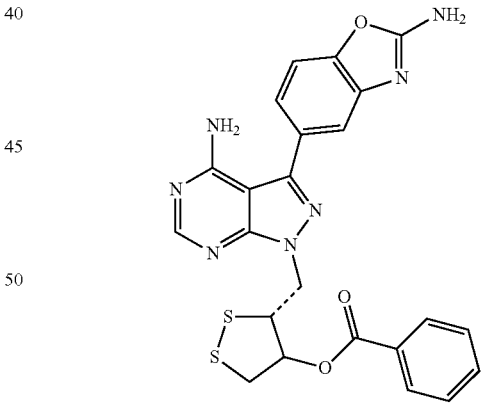

has the chemical name trans 3-((4-amino-3-(2-aminobenzo[d]oxazol-5-yl)-1H-pyrazolo[3,4-d]pyrimidin-1-yl)methyl)-1,2-dithiolan-4-yl benzoate.

For the purposes of demonstrating the manner in which the compounds of the present invention are named and referred to herein, the compound having the formula:

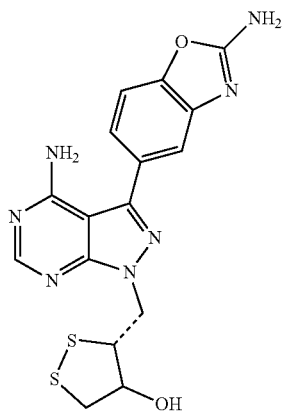

has the chemical name trans 3-((4-amino-3-(2-aminobenzo[d]oxazol-5-yl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

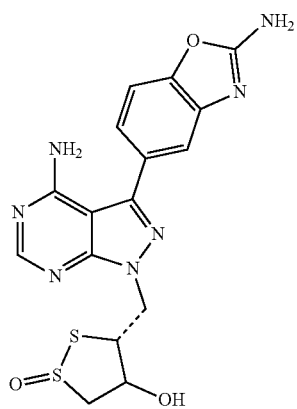

has the chemical name trans 3-((4-amino-3-(2-aminobenzo[d]oxazol-5-yl)-1H-pyrazolo[3,4-d]pyrimidin-1-yl)methyl)-4-hydroxy-1,2-dithiolane 1-oxide.

For the purposes of demonstrating the manner in which the compounds of the present invention are named and referred to herein, the compound having the formula:

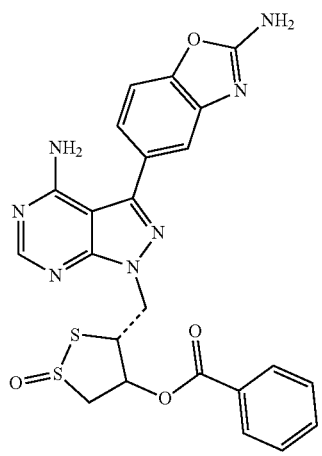

has the chemical name trans 3-((4-amino-3-(2-aminobenzo[d]oxazol-5-yl)-1H-pyrazolo[3,4-d]pyrimidin-1-yl)methyl)-1-oxido-1,2-dithiolan-4-yl benzoate.

For the purposes of demonstrating the manner in which the compounds of the present invention are named and referred to herein, the compound having the formula:

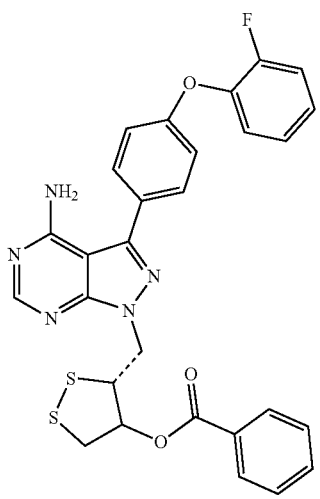

has the chemical name trans 3-((4-amino-3-(4-(2-fluorophenoxyphenyl)-1H-pyrazolo[3,4-d]pyrimidin-1-yl)methyl)-1,2-dithiolan-4-yl benzoate.

For the purposes of demonstrating the manner in which the compounds of the present invention are named and referred to herein, the compound having the formula:

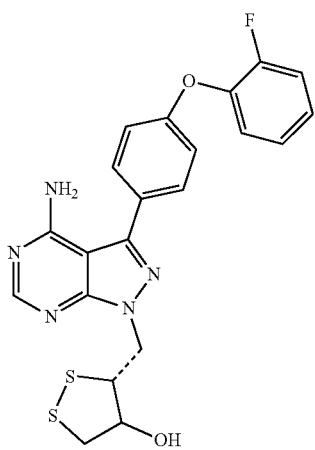

has the chemical name trans 3-((4-amino-3-(4-(2-fluorophenoxyphenyl)-1H-pyrazolo[3,4-d]pyrimidin-1-yl)methyl)-1,2-dithiolan-4-ol.

For the purposes of demonstrating the manner in which the compounds of the present invention are named and referred to herein, the compound having the formula:

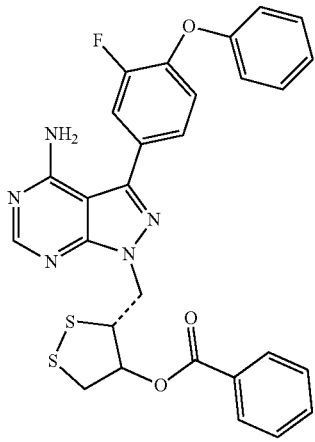

has the chemical name trans 3-((4-amino-3-(3-(3-fluoro-4-phenoxyphenyl)-1H-pyrazolo[3,4-d]pyrimidin-1-yl)methyl)-1,2-dithiolan-4-yl benzoate.

For the purposes of demonstrating the manner in which the compounds of the present invention are named and referred to herein, the compound having the formula:

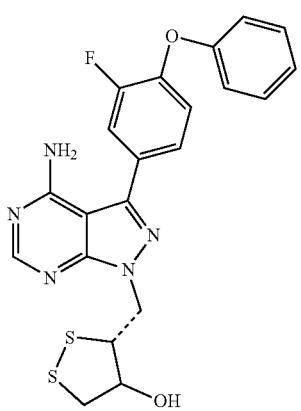

has the chemical name trans 3-((4-amino-3-(3-(3-fluoro-4-phenoxyphenyl)-1H-pyrazolo[3,4-d]pyrimidin-1-yl) methyl)-1,2-dithiolan-4-ol In all of the embodiments provided herein, examples of suitable optional substituents are not intended to limit the scope of the claimed invention. The compounds of the invention may contain any of the substituents, or combinations of substituents, provided herein.

It will also be appreciated by those of skilled in the art, may be administered to a mammal and thereafter metabolized in the body to form compounds of the invention which are pharmacologically active. Such derivatives may therefore be described as "prodrugs". All prodrugs of compounds of formula (I) are included within the scope of this invention.

It is understood that one skilled in the art would be able to make compounds of the invention by similar methods as shown below, or by methods known to one skilled in the art. It is also understood that one skilled in the art would be able to make in a similar manner as described below other compounds of formula (I) not specifically illustrated below by using appropriate starting components and modifying the parameters of the synthesis as needed. In general, starting materials may be obtained from sources such as Sigma Aldrich, TCI and the like, or synthesized according to sources known to those of skill in the art (see Smith, M. B. and J. March, *Advanced Organic Chemistry: Reactions, Mechanisms and Structure*, 5$^{th}$ edition (Wiley, December 2000).

Combination Therapy

In another embodiment of the invention, a compound of the disclosure may be combined with one or more additional compounds of the disclosure for the treatment of tyrosine kinases-mediated disease and conditions. The compound of the disclosure may be administered simultaneously, sequentially or separately with the one or more additional compounds of the disclosure for the treatment of tyrosine kinases-mediated disease and conditions. In a further embodiment of the invention, a compound of the disclosure may be combined with one or more additional compounds of the disclosure and an excipient for the treatment of tyrosine kinases-mediated disease and conditions.

In another embodiment of the invention, a compound of the disclosure may be combined with an anti-cancer agent for the treatment of tyrosine kinases-mediated disease and conditions. The compound of the disclosure may be administered simultaneously, sequentially or separately with for the treatment of tyrosine-mediated disease and conditions. Anti-cancer agents include receptor tyrosine kinase inhibitors such as erlotinib, neratinib, dacomitinib, afatinib, pelitinib, gefitinib, crizotinib, rociletinib, osimertinib, HM61713, AST-1306, WZ4002, and the like. Said anti-cancer agents also include non receptor tyrosine kinase inhibitors such as ibrutinib, pacritinib, tideglusib, RVX-208, BMS-536924, MNS, quizartinib, dovitinib, tandutinib, KW-2449, ENMD-2076, UNC-2025, AMG925, AZD2932, cabozantinib, R406, ruxolitinib, tofacitinib, AZD1480, fedratinib, AT9283, momelotinib, gandotinib, baricitinib, AZ960, CEP-33779, XL019, ruxolitinib, decernotinib, cerdulatinib, filgotinib, saracatinib, dasatinib, bosutinib, KX2-391, PP2, SU6656, WH-4-023, OSI 923, raf inhibitors, AZ 628, SGX-523, Dabrafenib, RO5126766, CEP-32496, ERK inhibitors SCH772984, VX-11e, ulxertinib, GDC-0994, MEK inhibitors including selumetinib, PD0325901, trametinib, U0126, PD184352, BIX 02189, pimasertib, AZD8330, binimetinib, GDC-0623, refametinib phosphatidylinositol 3-kinase (PI3K) inhibitors such as wortmannin, demethoxyviridin, LY294002, perifosine, idelalisib, PX-866, IPI-145, BAY 80-6946, BEZ235, RP6530, TGR 1202, SF1126, INK1117, GDC-0941, BKM120, XL147, XL765, Palomid 529, GSK1059615, ZSTK474, PWT33597, IC87114, TG100-115, CAL263, RP6503, PI-103, GNE-477, CUDC-907, AEZS-136, and the like, AKT inhibitors such as MK 2206, MKC-1, GSK 690693, FPA 124, AT7867, GDC-0068, ALM301, AZD5363, KP372-1 and the like, mTor inhibitors such as rapamycin, everolimus, temsirolimus, ridaforolimus, sirolimus, AZD8055, XL388, KU-0063794, GDC-0349, WYE-354, GSK1059615, PP242, Palomid 529, OSI-027, PF-05212384, WAY-600, WYE-125132, WYE-687, AZD2014, INK 128, Torin 1, Torin 2 and the like, c-Met inhibitors such as SU11274, K252a, PHA-665752, PHA-66752, PF-2341066, BMS-777607, JNJ-38877605, PF-04217903, MK-2461, GSK 1363089, AMG-458, tivantinib, INCB28060, cabozantinib, foretinib, and the like, vascular endothelial growth factor (VEGF) monoclonal antibodies such as bevacizumab, ranibizumab, and the like, PD-1 immunotherapy such as pembrolizumab, epidermal growth factor receptor (EGFR) inhibitor such as gefitinib, erlotinib, and the like, epidermal growth factor receptor (EGFR) monoclonal antibodies such as cetuximab, panitumumab and the like, Wnt pathway inhibitors such as XAV939 and the like, bioactive flavolignans such as silibinin and the like, DNA methylation inhibitors such as 5-aza-2'-deoxycytidine and the like, platinum based anticancer agents such as carboplatin, cisplatin, and the like. Anticancer agents also include paclitaxel, gemcitabine, docetaxel, vinorelbine, irinotecan, pemetrexed, and the like, dual anti-cancer therapies such as carboplatin/paclitaxel, carboplatin/gemcitabine, carboplatin/docetaxel, carboplatin/vinorelbine, carboplatin/irinotecan, carboplatin/pemetrexed, cisplatin/paclitaxel, cisplatin/gemcitabine, cisplatin/docetaxel, cisplatin/vinorelbine, cisplatin/irinotecan, cisplatin/pemetrexed, and the like. Anti-cancer agents also includes autophagy inducing agents such as imatinib and the like, Rexinoids or retinoid x receptor selective ligands such as baroxetene and the like, Cyclooxygenase-2 inhibitor such as rofecoxib and the like, Src family kinases and Bcr-Abl inhibitor such as bosulif and the like, and Recombinant adenoviral vector TRAIL protein.

In another embodiment of the invention, a compound of the disclosure may be combined with radiation therapy for the treatment of tyrosine kinases-mediated disease and conditions.

Kits

The present invention also provides kits that contain a pharmaceutical composition which includes one or more compounds of the invention. The kit also includes instructions for the use of the pharmaceutical composition for modulating the activity of RTK, for the treatment of cancer, as well as other utilities as disclosed herein. Preferably, a commercial package will contain one or more unit doses of the pharmaceutical composition.

Preparation of the Compounds of the Invention

The present invention further relates to processes for preparing the compounds of the disclosure. Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatograpy (HPLC), gas chromatography (GC), gel-permeation chromatography (GPC), or thin layer chromatography (TLC). Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

General Synthetic Schemes for Preparation of Compounds

The reagents used in the preparation of the compounds of this invention can be either commercially obtained or can be

Scheme 1

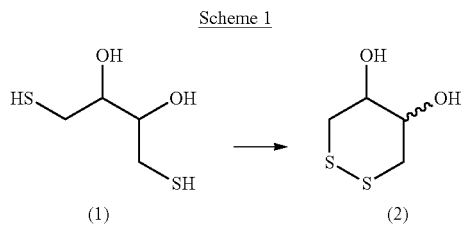 [SMILES: OC(CS)C(O)CS ; OC1CSSCC1O]

A compound of the formula (1), a known compound or compound prepared by known methods, is reacted with dimethylsulfoxide or potassium ferricyanide in a solvent such as water in the presence of a base such as potassium hydroxide, sodium hydroxide, lithium hydroxide and the like, optionally with heating, optionally with microwave irradiation to provide a compound of the formula (2).

Scheme 2

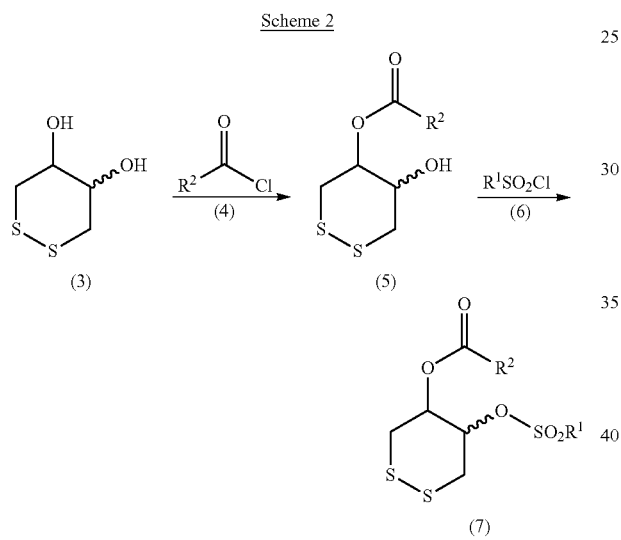

A compound of the formula (3), a known compound or compound prepared by known methods, is reacted with a known compound of formula (4) or compound prepared by known methods such as benzoyl chloride, p-nitrobenzoyl chloride and the like in the presence of a base such as, trimethylamine, pyridine, picoline, lutidine, diisopropylethylamine and the like in a solvent such as methylene chloride, 1,2-dichloroethane, acetonitrile, N,N dimethylformamide, N,N dimethylacetamide, dioxane, tetrahydrofuran optionally with heating, optionally with microwave irradiation to provide a compound of the formula (5).

A compound of the formula (5), a known compound or compound prepared by known methods, is reacted with a known compound of formula (6) or compound prepared by known methods such as methanesulfonyl chloride, trifluoromethanesulfonyl chloride, and the like in the presence of a base such as, trimethylamine, diisopropylethylamine, pyridine, picoline, lutidine, and the like in a solvent such as methylene chloride, 1,2-dichloroethane, acetonitrile, toluene, dioxane, tetrahydrofuran optionally with heating, optionally with microwave irradiation to provide a compound of the formula (7).

Scheme 3

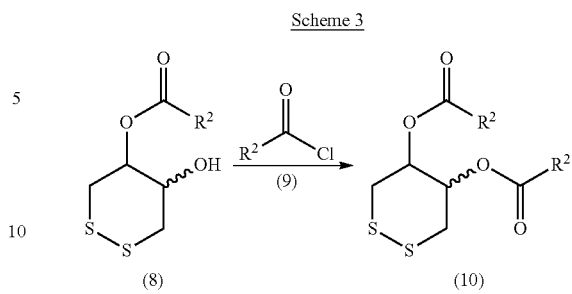

A compound of the formula (8), a known compound or compound prepared by known methods, is reacted with a known compound of formula (9) or compound prepared by known methods such as benzoyl chloride, p-nitrobenzoyl chloride and the like in the presence of a base such as, trimethylamine, pyridine, picoline, lutidine, diisopropylethylamine and the like in a solvent such as methylene chloride, 1,2-dichloroethane, acetonitrile, N,N dimethylformamide, N,N dimethylacetamide, dioxane, tetrahydrofuran optionally with heating, optionally with microwave irradiation to provide a compound of the formula (10).

Scheme 4

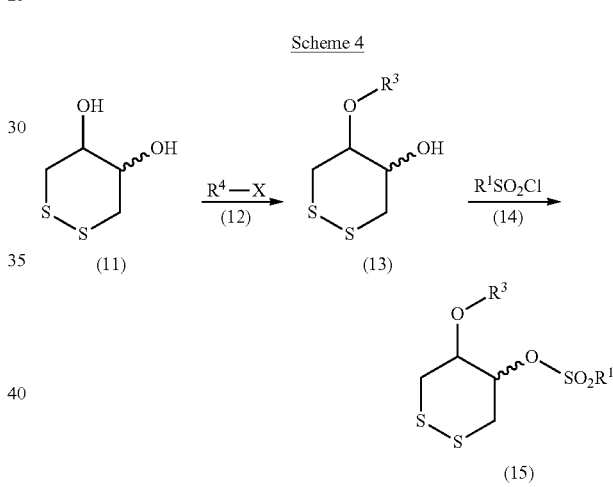

A compound of the formula (11), a known compound or compound prepared by known methods, is reacted with a known compound of formula (12) or compound prepared by known methods such as methyl iodide, ethyl iodide, benzyl bromide and the like in the presence of a base such as, sodium hydride, potassium hydride, trimethylamine, pyridine, picoline, lutidine, diisopropylethylamine and the like in a solvent such as tetrahydrofuran, ether, dioxane, methylene chloride, 1,2-dichloroethane, acetonitrile, N,N dimethylformamide, N,N dimethylacetamide, optionally with heating, optionally with microwave irradiation to provide a compound of the formula (13).

A compound of the formula (13), a known compound or compound prepared by known methods, is reacted with a known compound of formula (14) or compound prepared by known methods such as methanesulfonyl chloride, trifluoromethanesulfonyl chloride, and the like in the presence of a base such as, trimethylamine, diisopropylethylamine, pyridine, picoline, lutidine, and the like in a solvent such as methylene chloride, 1,2-dichloroethane, acetonitrile, toluene, dioxane, tetrahydrofuran optionally with heating, optionally with microwave irradiation to provide a compound of the formula (15).

Scheme 5

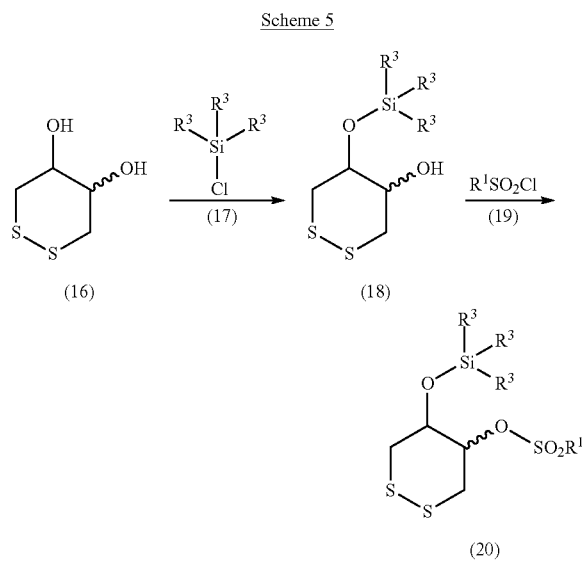

Scheme 7

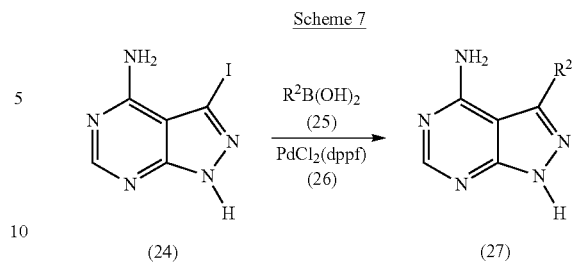

A compound of the formula (24), a known compound or compound prepared by known methods, is reacted with a known compound of formula (25) or compound prepared by known methods such as phenylboronic acid, p-methoxyphenylboronic acid, p-chlorophenylboronic acid and the like, in the presence of a phosphate salt such as potassium phosphate, sodium phosphate, and the like in the presence of a palladium catalyst (26) such as palladium acetate, tetrakis(triphenylphosphine)palladium(0), bis(triphenylphosphine)palladium(II) dichloride, (1,1'-bis(diphenylphosphino)ferrocene)palladium(II) dichloride and the like a solvent such as N,N dimethylformamide, N,N dimethylacetamide, acetonitrile, tetrahydrofuran, 1,4-dioxane, water, and the like, optionally with heating, optionally with microwave irradiation to provide a compound of the formula (27).

A compound of the formula (16), a known compound or compound prepared by known methods, is reacted with a known compound of formula (17) or compound prepared by known methods such as trimethylsilyl chloride, t-butyldimethylsilyl chloride, and the like in the presence of a base such as, imidazole, trimethylamine, pyridine, picoline, lutidine, diisopropylethylamine and the like in a solvent such as tetrahydrofuran, ether, dioxane, methylene chloride, 1,2-dichloroethane, N,N dimethylformamide, N,N dimethylacetamide, optionally with heating, optionally with microwave irradiation to provide a compound of the formula (18).

A compound of the formula (18), a known compound or compound prepared by known methods, is reacted with a known compound of formula (19) or compound prepared by known methods such as methanesulfonyl chloride, trifluoromethanesulfonyl chloride, and the like, in the presence of a base such as, trimethylamine, diisopropylethylamine, pyridine, picoline, lutidine, and the like in a solvent such as methylene chloride, 1,2-dichloroethane, acetonitrile, toluene, dioxane, tetrahydrofuran optionally with heating, optionally with microwave irradiation to provide a compound of the formula (20).

Scheme 8

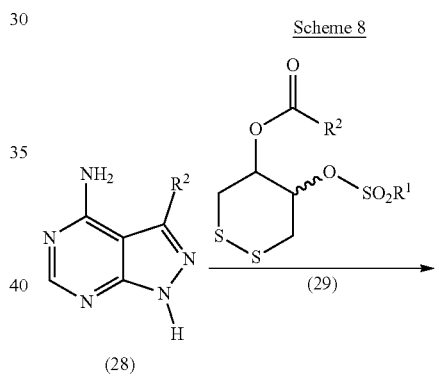

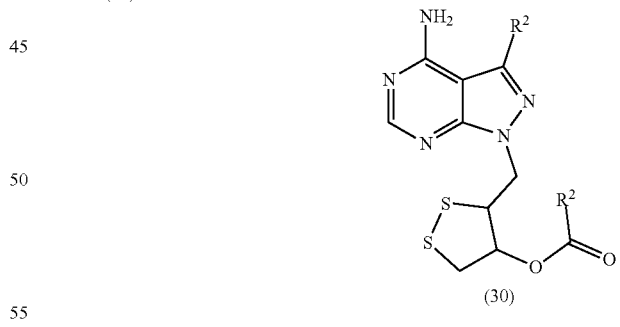

Scheme 6

A compound of the formula (21), a known compound or compound prepared by known methods, is reacted with a known compound of formula (22) such as N-iodosuccinimde or N-bromosuccinimide or compound prepared by known methods and the like in a solvent such as tetrahydrofuran, ether, dioxane, acetonitrile, N,N dimethylformamide, N,N dimethylacetamide, optionally with heating, optionally with microwave irradiation to provide a compound of the formula (23).

A compound of the formula (28), a known compound or compound prepared by known methods, is reacted with an inorganic base such as potassium carbonate, sodium carbonate, cesium carbonate, sodium hydride, potassium hydride, and the like in a polar aprotic solvent such as N,N dimethylformamide, N,N dimethylacetamide, acetonitrile, tetrahydrofuran, dioxane and the like, followed by reaction with a known compound of formula (29) or compound prepared by known methods such as 5-((methylsulfonyl)oxy)-1,2-dithian-4-yl benzoate, and the like, in a in a polar aprotic solvent such as such as N,N dimethylformamide, N,N dimethylacetamide, acetonitrile, tetrahydrofuran, dioxane and the like optionally with heating, optionally with microwave irradiation to produce a compound of formula (30).

fonate and the like, optionally with heating, optionally with microwave irradiation to produce a compound of formula (35).

Scheme 9

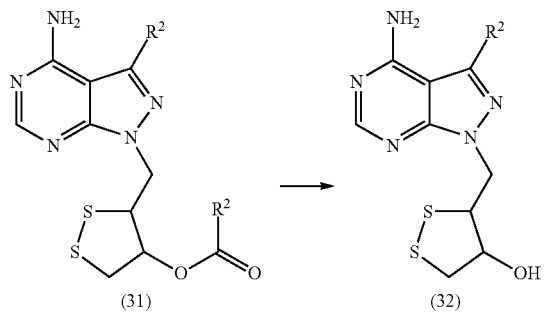

(31)  (32)

A compound of the formula (31), is reacted with a base such as lithium hydroxide, sodium hydroxide, potassium hydroxide, potassium carbonate, cesium carbonate and the like, in a solvent such as methanol, ethanol, N,N dimethylformamide, N,N dimethylacetamide, acetonitrile, tetrahydrofuran, dioxane and the like, optionally with heating, optionally with microwave irradiation to provide a compound of formula (32).

Scheme 10

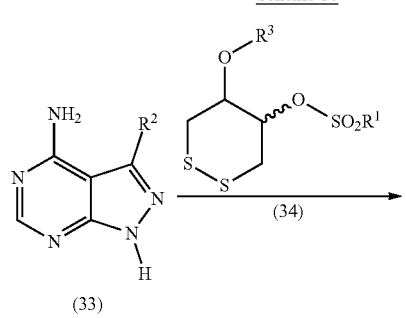

(33)

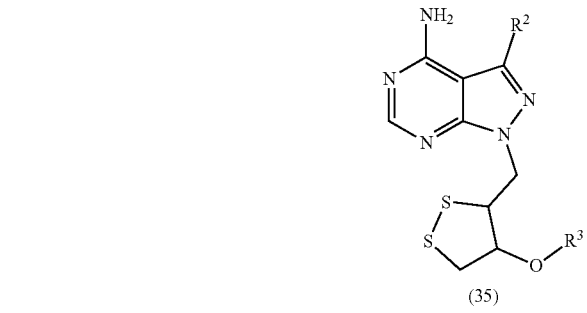

(35)

A compound of the formula (33), a known compound or compound prepared by known methods, is reacted with an inorganic base such as potassium carbonate, sodium carbonate, cesium carbonate, sodium hydride, potassium hydride, and the like in a polar aprotic solvent such as N,N dimethylformamide, N,N dimethylacetamide, acetonitrile, tetrahydrofuran, dioxane and the like, followed by further reaction with a compound of formula (34) or compound prepared by known methods such as 5-methoxy-1,2-dithian-4-yl methanesulfonate, 5-(benzyloxy)-1,2-dithian-4-yl methanesul- Scheme 11

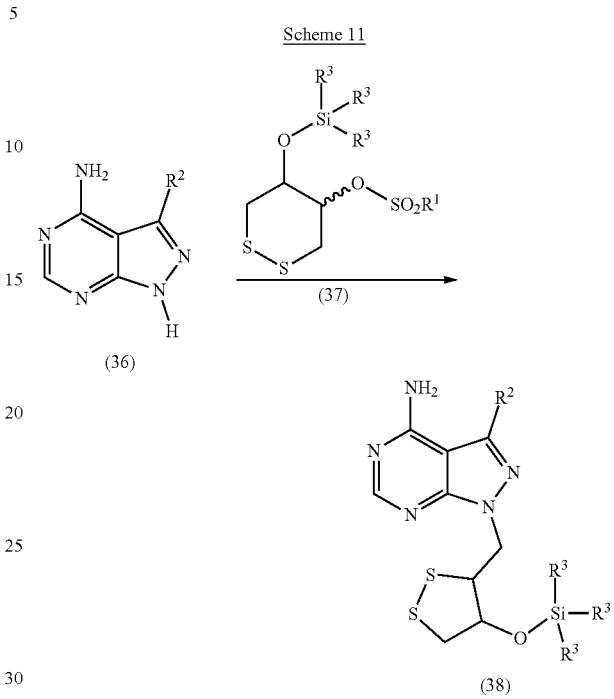

(36)  (37)

(38)

A compound of the formula (36), a known compound or compound prepared by known methods, is reacted with an inorganic base such as potassium carbonate, sodium carbonate, cesium carbonate, sodium hydride, potassium hydride, and the like in a polar aprotic solvent such as N,N dimethylformamide, N,N dimethylacetamide, acetonitrile, tetrahydrofuran, dioxane and the like, followed by reaction with a compound of formula (37) or compound prepared by known methods such as 5-tert-butyldimethylsilyloxy-1,2-dithian-4-yl methanesulfonate and the like, optionally with heating, optionally with microwave irradiation to provide a compound of formula (38).

Scheme 12

(39)  (40)

A compound of the formula (39) is reacted with a tetra-n-butylammonium fluoride, hydrofluoric acid in pyridine, camphorsulfonic acid and the like, in a solvent such as N,N dimethylformamide, N,N dimethylacetamide, acetonitrile, tetrahydrofuran, dioxane and the like optionally with heating, optionally with microwave irradiation to provide a compound of formula (40).

Scheme 13

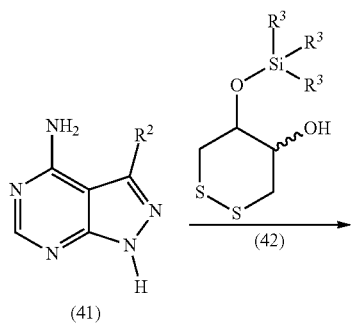

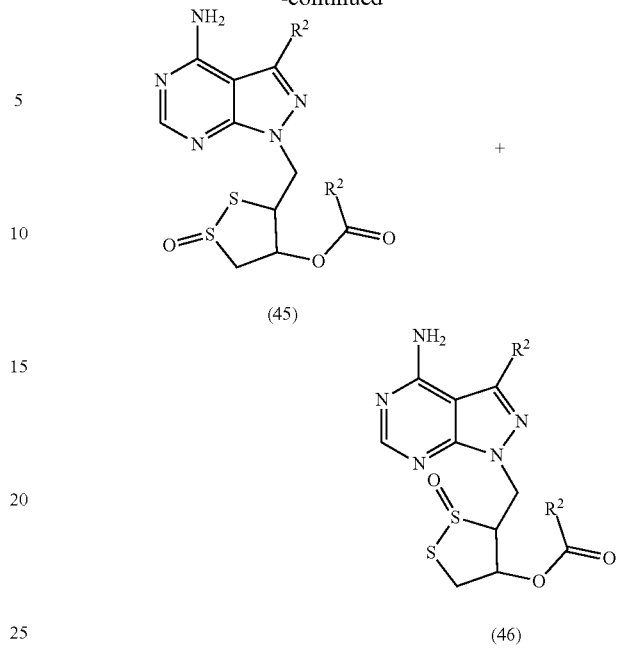

A compound of the formula (41), a known compound or compound prepared by known methods, is reacted with a compound of formula (42) such as 5-tert-butyldimethylsilyloxy-1,2-dithiane-4-ol and the like, in the presence of triphenylphosphine or resin-bound triphenylphosphine and an azodicarboxylate such as diethyl azodicarboxylate, diisopropyl azodicarboxylate, di-t-butylazodicarboxylate, di-(4-chlorobenzyl)azodicarboxylate in the presence of a solvent such as tetrahydrofuran, diethyl ether, dioxane and the like, optionally with heating, optionally with microwave irradiation to provide a compound of the formula (43).

Scheme 14

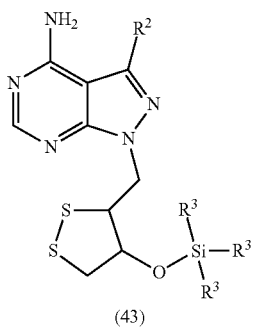

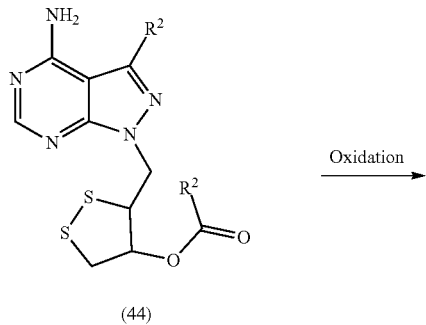

A compound of the formula (44) is reacted with an oxidizing agent such as m-chloroperoxybenzoic acid, monoperphthalic acid, peracetic acid, perpropionic acid, pertrifluoroacetic acid, potassium periodate, sodium metaperiodate, sodium perborate, potassium peroxymonosulfate (Oxone®), potassium peroxydisulfate, dimethyldioxirane, and the like, in the presence of a solvent such as tetrahydrofuran, ether, 1,4-dioxane, acetone, acetonitrile, methanol, ethanol, isopropanol, water, and the like, optionally with heating, optionally with microwave irradiation to provide compounds of the formula (45) and (46). Alternatively, a formula of the compound (44) is reacted with a sulfoxide such as diphenyl sulfoxide, dimethyl sulfoxide, and the like, in the presence of a rhenium catalyst such as $ReOCl_3$ $(PPh_3)_2$, and the like, in a solvent such as methylene chloride, 1,2-dichloroethane, chloroform, tetrahydrofuran, ether, 1,4-dioxane, acetone, acetonitrile, and the like, optionally with heating, optionally with microwave irradiation to provide compounds of the formula (45) and (46). Alternatively, a formula of the compound (44) is reacted with a urea hydrogen peroxide complex in the presence of a rhenium catalyst such as $ReOCl_3(PPh_3)_2$, and the like, in a solvent such as methylene chloride, 1,2-dichloroethane, chloroform, tetrahydrofuran, ether, 1,4-dioxane, acetone, acetonitrile, N,N-dimethylformamide, and the like, optionally with heating, optionally with microwave irradiation to provide compounds of the formula (45) and (46). Alternatively, a formula of the compound (44) is reacted with an oxidoreductase such as Baeyer-Villiger monooxygenase, cytochrome P450 2C9, cytochrome P450 2C19, cytochrome P450 3A4 and, in a solvent such as water, methanol, ethanol, isopropanol, acetonitrile, acetone, and the like, optionally with heating, optionally with microwave irradiation to provide compounds of the formula (45) and (46). Alternatively, a compound of the formula (44) is reacted with hydrogen peroxide in the presence titanium (IV) isopropoxide-diethyltartarate, optionally in the presence of an amino alcohol such as 2-amino-3-phenylpropan-1-ol, 2-amino-4-methylpentan-1-ol, 2-amino-4-(methylthio)butan-1-ol, 2-aminopropan-1-ol, and the like, in a solvent such as methylene chloride, 1,2-dichloroethane, chloroform, tetrahydrofuran, ether, 1,4-dioxane, acetone, acetonitrile, N,N-dimethylformamide, and the like optionally with heating, optionally with microwave irradiation to provide compounds of the formula (45) and (46). Alternatively, a compound of the formula of the compound (44) is electrochemically oxidized optionally in the presence of a buffer solution such as a sodium phosphate solution, a potassium phosphate solution, and the like to provide compounds of the formula (45) and (46). Alternatively, a compound of the formula of the compound (44) is photochemically oxidized in a solvent such as methylene chloride, 1,2-dichloroethane, chloroform, tetrahydrofuran, ether, 1,4-dioxane, acetone, acetonitrile, N,N-dimethylformamide, water, methanol, ethanol, isopropanol, and the like, optionally with heating, optionally with microwave irradiation to provide compounds of the formula (45) and (46). It is understood that one skilled in the art would readily understand that the ratio of products (45) through (46) will be controlled by the amount of oxidant added and would adjust the amount of oxidant accordingly to produce the desired ration of products.

Scheme 15

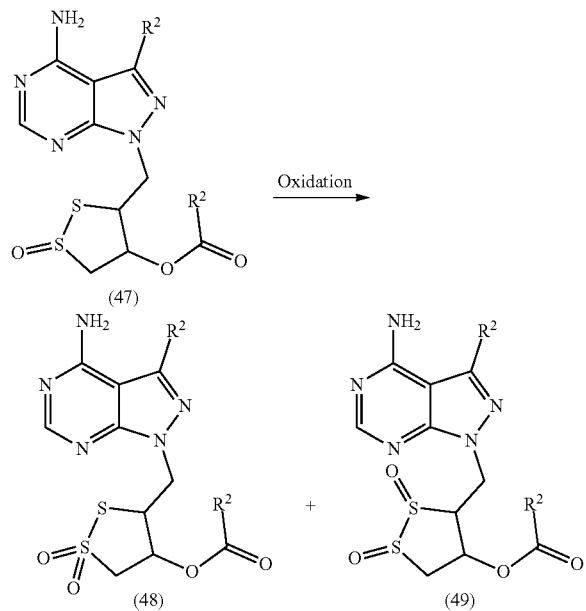

A compound of the formula (47) is reacted with an oxidizing agent such as m-chloroperoxybenzoic acid, monoperphthalic acid, peracetic acid, perpropionic acid, pertrifluoroacetic acid, potassium periodate, sodium metaperiodate, sodium perborate, potassium peroxymonosulfate (Oxone®), potassium peroxydisulfate, dimethyldioxirane, and the like, in the presence of a solvent such as tetrahydrofuran, ether, 1,4-dioxane, acetone, acetonitrile, methanol, ethanol, isopropanol, water, and the like, optionally with heating, optionally with microwave irradiation to provide compounds of the formula (48) and (49). Alternatively, a formula of the compound (47) is reacted with a sulfoxide such as diphenyl sulfoxide, dimethyl sulfoxide, and the like, in the presence of a rhenium catalyst such as ReOCl$_3$(PPh$_3$)$_2$, and the like, in a solvent such as methylene chloride, 1,2-dichloroethane, chloroform, tetrahydrofuran, ether, 1,4-dioxane, acetone, acetonitrile, and the like, optionally with heating, optionally with microwave irradiation to provide compounds of the formula (48) and (49). Alternatively, a formula of the compound (47) is reacted with a urea hydrogen peroxide complex in the presence of a rhenium catalyst such as ReOCl$_3$(PPh$_3$)$_2$, and the like, in a solvent such as methylene chloride, 1,2-dichloroethane, chloroform, tetrahydrofuran, ether, 1,4-dioxane, acetone, acetonitrile, N,N-dimethylformamide, and the like, optionally with heating, optionally with microwave irradiation to provide compounds of the formula (48) and (49). Alternatively, a formula of the compound (47) is reacted with an oxidoreductase such as Baeyer-Villiger monooxygenase, cytochrome P450 2C9, cytochrome P450 2C19, cytochrome P450 3A4 and, in a solvent such as water, methanol, ethanol, isopropanol, acetonitrile, acetone, and the like, optionally with heating, optionally with microwave irradiation to provide compounds of the formula (48) and (49). Alternatively, a compound of the formula (47) is reacted with hydrogen peroxide in the presence titanium (IV) isopropoxide-diethyltartarate, optionally in the presence of an amino alcohol such as 2-amino-3-phenylpropan-1-ol, 2-amino-4-methylpentan-1-ol, 2-amino-4-(methylthio)butan-1-ol, 2-aminopropan-1-ol, and the like, in a solvent such as methylene chloride, 1,2-dichloroethane, chloroform, tetrahydrofuran, ether, 1,4-dioxane, acetone, acetonitrile, N,N-dimethylformamide, and the like optionally with heating, optionally with microwave irradiation to provide compounds of the formula (48) and (49). Alternatively, a compound of the formula of the compound (47) is electrochemically oxidized optionally in the presence of a buffer solution such as a sodium phosphate solution, a potassium phosphate solution, and the like to provide compounds of the formula (48) and (49). Alternatively, a compound of the formula of the compound (47) is photochemically oxidized in a solvent such as methylene chloride, 1,2-dichloroethane, chloroform, tetrahydrofuran, ether, 1,4-dioxane, acetone, acetonitrile, N,N-dimethylformamide, water, methanol, ethanol, isopropanol, and the like, optionally with heating, optionally with microwave irradiation to provide compounds of the formula (48) and (49). It is understood that one skilled in the art would readily understand that the ratio of products (48) through (49) will be controlled by the amount of oxidant added and would adjust the amount of oxidant accordingly to produce the desired ration of products.

Scheme 16

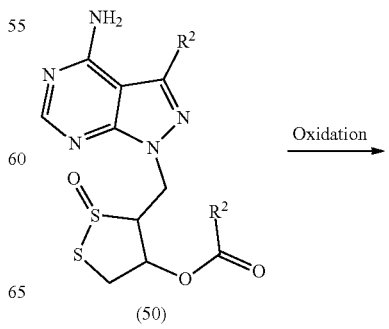

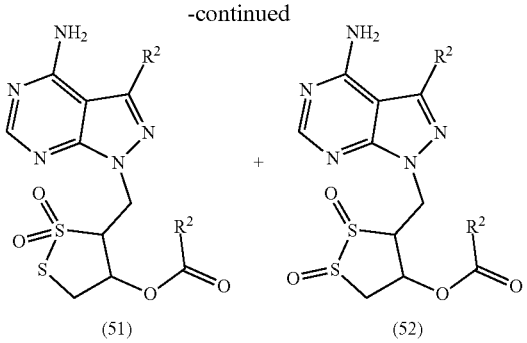

(51)  +  (52)

A compound of the formula (50) is reacted with an oxidizing agent such as m-chloroperoxybenzoic acid, monoperphthalic acid, peracetic acid, perpropionic acid, pertrifluoroacetic acid, potassium periodate, sodium metaperiodate, sodium perborate, potassium peroxymonosulfate (Oxone®), potassium peroxydisulfate, dimethyldioxirane, and the like, in the presence of a solvent such as tetrahydrofuran, ether, 1,4-dioxane, acetone, acetonitrile, methanol, ethanol, isopropanol, water, and the like, optionally with heating, optionally with microwave irradiation to provide compounds of the formula (51) and (52). Alternatively, a formula of the compound (50) is reacted with a sulfoxide such as diphenyl sulfoxide, dimethyl sulfoxide, and the like, in the presence of a rhenium catalyst such as $ReOCl_3(PPh_3)_2$, and the like, in a solvent such as methylene chloride, 1,2-dichloroethane, chloroform, tetrahydrofuran, ether, 1,4-dioxane, acetone, acetonitrile, and the like, optionally with heating, optionally with microwave irradiation to provide compounds of the formula (51) and (52). Alternatively, a formula of the compound (50) is reacted with a urea hydrogen peroxide complex in the presence of a rhenium catalyst such as $ReOCl_3(PPh_3)_2$, and the like, in a solvent such as methylene chloride, 1,2-dichloroethane, chloroform, tetrahydrofuran, ether, 1,4-dioxane, acetone, acetonitrile, N,N-dimethylformamide, and the like, optionally with heating, optionally with microwave irradiation to provide compounds of the formula (51) and (52). Alternatively, a formula of the compound (50) is reacted with an oxidoreductase such as Baeyer-Villiger monooxygenase, cytochrome P450 2C9, cytochrome P450 2C19, cytochrome P450 3A4 and, in a solvent such as water, methanol, ethanol, isopropanol, acetonitrile, acetone, and the like, optionally with heating, optionally with microwave irradiation to provide compounds of the formula (51) and (52). Alternatively, a compound of the formula (50) is reacted with hydrogen peroxide in the presence titanium (IV) isopropoxide-diethyltartarate, optionally in the presence of an amino alcohol such as 2-amino-3-phenylpropan-1-ol, 2-amino-4-methylpentan-1-ol, 2-amino-4-(methylthio)butan-1-ol, 2-aminopropan-1-ol, and the like, in a solvent such as methylene chloride, 1,2-dichloroethane, chloroform, tetrahydrofuran, ether, 1,4-dioxane, acetone, acetonitrile, N,N-dimethylformamide, and the like optionally with heating, optionally with microwave irradiation to provide compounds of the formula (51) and (52). Alternatively, a compound of the formula of the compound (50) is electrochemically oxidized optionally in the presence of a buffer solution such as a sodium phosphate solution, a potassium phosphate solution, and the like to provide compounds of the formula (51) and (52). Alternatively, a compound of the formula of the compound (50) is photochemically oxidized in a solvent such as methylene chloride, 1,2-dichloroethane, chloroform, tetrahydrofuran, ether, 1,4-dioxane, acetone, acetonitrile, N,N-dimethylformamide, water, methanol, ethanol, isopropanol, and the like, optionally with heating, optionally with microwave irradiation to provide compounds of the formula (51) and (52). It is understood that one skilled in the art would readily understand that the ratio of products (51) through (52) will be controlled by the amount of oxidant added and would adjust the amount of oxidant accordingly to produce the desired ration of products.

Scheme 17

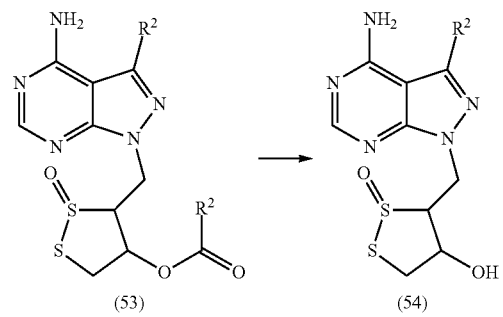

(53)  →  (54)

A compound of the formula (53), is reacted with a base such as lithium hydroxide, sodium hydroxide, potassium hydroxide, potassium carbonate, cesium carbonate and the like, in a solvent such as methanol, ethanol, N,N dimethylformamide, N,N dimethylacetamide, acetonitrile, tetrahydrofuran, dioxane and the like optionally with heating, optionally with microwave irradiation to provide a compound of formula (54).

Scheme 18

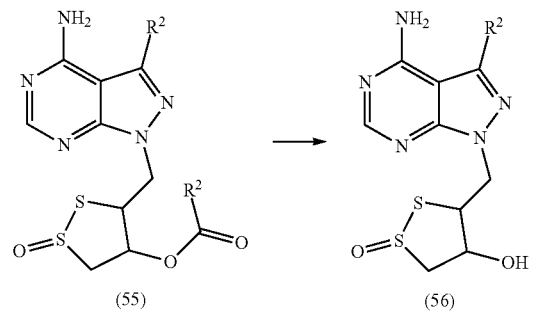

(55)  →  (56)

A compound of the formula (55), is reacted with a base such as lithium hydroxide, sodium hydroxide, potassium hydroxide, potassium carbonate, cesium carbonate and the like, in a solvent such as methanol, ethanol, N,N dimethylformamide, N,N dimethylacetamide, acetonitrile, tetrahydrofuran, dioxane and the like optionally with heating, optionally with microwave irradiation to provide a compound of formula (56).

Scheme 19

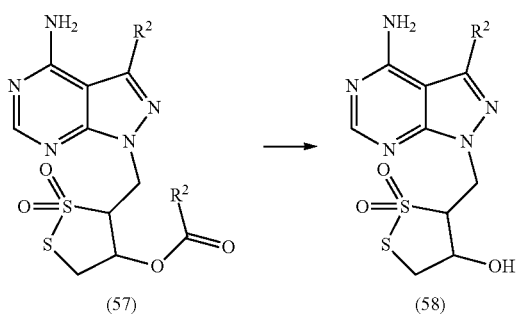

A compound of the formula (57), is reacted with a base such as lithium hydroxide, sodium hydroxide, potassium hydroxide, potassium carbonate, cesium carbonate and the like, in a solvent such as methanol, ethanol, N,N dimethylformamide, N,N dimethylacetamide, acetonitrile, tetrahydrofuran, dioxane and the like optionally with heating, optionally with microwave irradiation to provide a compound of formula (58).

Scheme 20

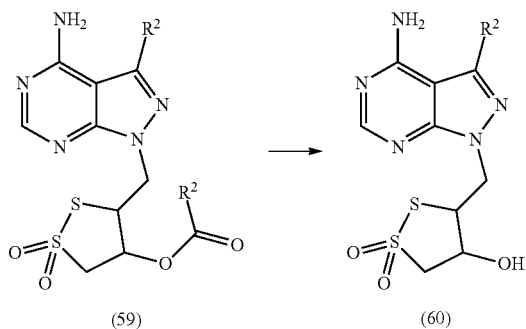

A compound of the formula (59), is reacted with a base such as lithium hydroxide, sodium hydroxide, potassium hydroxide, potassium carbonate, cesium carbonate and the like, in a solvent such as methanol, ethanol, N,N dimethylformamide, N,N dimethylacetamide, acetonitrile, tetrahydrofuran, dioxane and the like optionally with heating, optionally with microwave irradiation to provide a compound of formula (60).

The following examples further illustrate the present invention. It should be understood, however, that the invention is not limited solely to the particular examples given below.

Example 1

(4S,5S)-1,2-Dithiane-4,5-diol

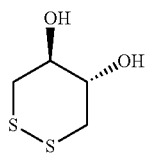

The compound (2S,3S)-1,4-dimercaptobutane-2,3-diol (4 g, 25.9 mmol) was dissolved in dimethylsulfoxide (2.3 g, 28.5 mmol) in an open beaker and heated to 110° C. with stirring for 3 hours. The reaction mixture was then cooled and dimethylsulfoxide was removed under vacuum to give a residual oil which was kept at room temperature for 20 minutes after which a white semi-solid was formed. About 25 mL of diethyl ether were added and the mixture was stirred for 10 minutes, then filtered. The solid was dried under vacuum to give a white solid (3.5 g, yield 90%). $^1$H NMR 400 MHz (DMSO-$d_6$): δ 5.23 (d, J=4.0 Hz, 2H), 3.39 (m, 2H), 3.06-3.02 (m, 2H), 2.54-2.50 (m, 2H); LCMS m/e: 135 [M+H−18]$^+$.

Example 2

(4S,5R)-1,2-Dithiane-4,5-diol

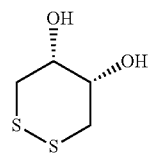

The compound (2R,3S)-1,4-dimercaptobutane-2,3-diol (2.5 g, 16.2 mmol) was dissolved in dimethylsulfoxide (1.4 g, 17.9 mmol) and in an open beaker was heated to 110° C. with vigorous stirring. After 3 hours, dimethylsulfoxide was removed under reduced pressure and the residual reaction mixture was allowed to stand at room temperature for 20 minutes. A white semi solid was formed to which was added diethyl ether (25 mL) and stirred for 10 minutes, then filtered. The resultant solid was dried under vacuum to give a white solid (2.3 g, yield 92%). $^1$H NMR 400 MHz (DMSO-$d_6$): δ 4.94 (m, 2H), 3.71 (m, 2H), 2.99-2.96 (m, 4H); LCMS m/e: 135 [M+H−18]$^+$.

Example 3 cis-1,2-Dithiane-4,5-diol

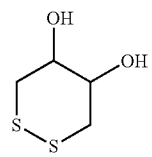

A solution of dithioerythritol (DTE, 22.0 g, 0.14 mol) in 537 mL of water was treated with potassium ferricyanide (0.8 M) solution (0.29 mol in 358 mL of water) until the yellow color persisted while maintaining pH 7 by addition of 2N KOH (0.29 mol in 143.2 mL of water). The solution was evaporated to dryness and 200 mL of ethanol was added to the crude product. After filtration, the clear filtrate was evaporated to dryness and crystallized from ethyl acetate/hexanes (2:1). The product was isolated by filtration as a white crystalline solid: m.p. 130-132° C.; $^1$H NMR (DMSO-$d_6$, 300 MHz) δ 2.70-3.00 (br s, 2H), 2.99 (dd, J=8.0, 13.2 Hz, 2H), 3.60-3.80 (br s, 2H), 4.80-5.00 (br s, 2H).

Example 4 trans 5-Hydroxy-1,2-dithian-4-yl benzoate

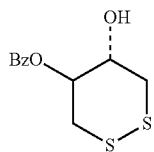

To a solution of trans-1,2-dithiane-4,5-diol (10.0 g, 0.065 mol), pyridine (15.9 mL, 0.20 mol) and methylene chloride (125 mL) at 0° C. was added benzoyl chloride (8.08 mL, 0.072 mol) over a period of 5 minutes. The reaction was then stirred for 15 hours at room temperature. The reaction mixture was then quenched with methanol (5.0 mL), washed with saturated aqueous sodium bicarbonate (1×50 mL), brine (1×50 mL), 1N HCl (1×50 mL), dried over sodium sulfate and concentrated to yield 19.2 g of crude product. The crude product was purified by column chromatography eluting with a gradient solvent of 5% to 20% ethyl acetate:hexanes to yield 10.85 g (65%) of the desired product as a white crystalline solid: m.p. 117-119° C.; $^1$H NMR (CDCl$_3$, 300 MHz) δ 2.62 (bd, J=5.8 Hz, 1H), 3.07 (dd, J=9.4, 13.5 Hz, 2H), 3.26-3.38 (m, 2H), 3.97-4.06 (m, 1H), 7.48 (t, J=7.9 Hz, 2H), 7.58-7.62 (m, 1H), 8.06 (d, J=7.0 Hz, 2H).

Example 5 trans 5-((Methylsulfonyl)oxy)-1,2-dithian-4-yl benzoate

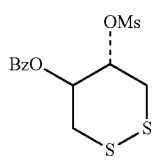

To a solution of trans 5-hydroxy-1,2-dithian-4-yl benzoate (0.55 g, 2.14 mmol) and triethylamine (0.96 mL, 6.86 mmol) in dichloromethane was added methanesulfonyl chloride (0.41 mL, 5.14 mmol) at 0° C. and the reaction mixture was stirred at room temperature for 2 hours. The mixture was then poured into water. The aqueous mixture extracted with ethyl acetate (3×300 mL) and the organic extracts were washed with water, dried over anhydrous Na$_2$SO$_4$ and concentrated at reduced pressure to give the title compound as a colorless solid (0.61 g, yield 90%). $^1$H NMR (CDCl$_3$, 400 MHz) δ 8.07 (d, J=8.0 Hz, 2H), 7.62-7.58 (m, 1H), 7.49-7.45 (m, 2H), 5.32-5.26 (m, 1H), 5.02-4.96 (m, 1H), 3.46-3.42 (m, 2H), 3.36-3.32 (m, 2H), 2.91 (s, 3H); LCMS m/e: 135 [M+H−32]$^+$.

Example 6 trans 5-(Benzoyloxy)-1,2-dithian-4-yl-4-nitrobenzoate

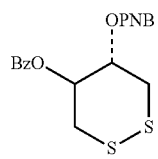

To a slurry of trans-1,2-dithiane-4-benzoate-5-ol (441 mg, 1.72 mmol), p-nitrobenzoic acid (1.44 g, 8.61 mmol), triphenyl phosphine (2.26 g, 8.61 mmol) in benzene (30 mL) at 0° C. was added diethylazodicarboxylate (DEAD, 1.36 mL, 1.50 g, 8.61 mmol) dropwise. The resulting clear yellow solution was then stirred overnight at room temperature. Thin layer chromatography (TLC) indicated that the starting material was consumed. The reaction mixture was adsorbed on silica gel (2.0 g) and purified by column chromatography (eluent 5% ethyl acetate/hexanes). The less polar compound gave 51 mg (8%) of the desired product; $^1$H NMR (CDCl$_3$, 400 MHz) δ 3.35 (m, 4H), 5.48 (m, 2H), 7.37 (t, J=7.8 Hz, 2H), 7.52 (t, J=7.3 Hz, 1H), 7.93 (d, J=7.3 Hz, 2H), 8.15 (dd, J=8.8 and 6.8 Hz, 4H).

Example 7 trans 1,2-Dithiane-4,5-diyl-dibenzoate

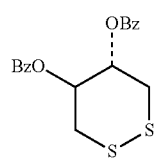

To a solution of trans-1,2-dithiane-4,5-diol (10.0 g, 0.065 mol), pyridine (15.9 mL, 15.57 g, 0.20 mol) and methylene chloride (125 mL) at 0° C. was added benzoyl chloride (8.08 mL, 0.072 mol) over a period of 5 min. The reaction was stirred for 15 hours at room temperature. The reaction mixture was then quenched with methanol (5 mL), washed with saturated aqueous sodium bicarbonate (1×50 mL), brine (1×50 mL), 1N HCl (1×50 mL), dried over anhydrous Na$_2$SO$_4$ and concentrated to yield 19.2 g of the crude product. The crude product comprising trans 5-hydroxy-1,2-dithian-4-yl benzoate and trans 1,2-dithiane-4,5-diyl-dibenzoate was purified by column chromatography eluting with a gradient solvent of 5% to 20% ethyl acetate/hexanes to yield 2.86 g (12%) of the desired product as a white crystalline solid: m.p. 139-141° C.; $^1$H NMR (CDCl$_3$, 300 MHz) δ 2.62 (bd, J=5.8 Hz, 1H), 3.07 (dd, J=4, 13.5 Hz, 2H), 3.26-3.38 (m, 2H), 3.97-4.06 (m, 1H), 7.48 (t, J=7.9 Hz, 2H), 7.58-7.62 (m, 1H), 7.58-7.62 (m, 1H), 8.06 (d, J=7.0 Hz, 2H).

Example 8 trans-5-tert-Butyldimethylsilyloxy-1,2-dithiane-4-ol

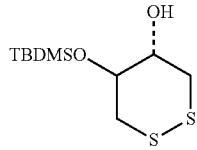

To a solution of trans-1,2-dithiane-4,5-diol (5.0 g, 0.033 mol), imidazole (3.14 g, 0.046 mol) and N,N dimethylformamide (DMF, 25 mL) at 0° C. was added a solution of tert-butyldimethylsilyl chloride (5.96 g, 0.040 mol) in N,N dimethylformamide (15 mL) over a period of 5 minutes. The reaction mixture was stirred for 20 hours at room temperature. The reaction mixture was then concentrated in vacuo, and the resulting residue dissolved in methylene chloride/methanol, then adsorbed on silica gel (3.0 g) and purified by column chromatography eluting with a gradient solvent of 2% to 5% ethyl acetate/hexanes to yield 7.77 g (99%) of the desired product as a clear, colorless oil; $^1$H NMR (CDCl$_3$, 300 MHz) δ 0.12 (d, J=3.8 Hz, 6H), 0.92 (s, 9H), 2.78 (bs, 1H), 2.82-3.70 (m, 4H), 3.58-3.70 (m, 2H).

Example 9 trans-5-tert-Butyldimethylsilyloxy-1,2-dithian-4-yl methanesulfonate

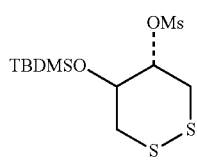

Methanesulfonyl chloride (0.93 mL, 137 mg, 1.2 mmol) was added to a solution of trans-5-tert-butyldimethylsilyloxy-1,2-dithiane-4-ol (266 mg, 1.0 mmol) and methylene chloride (15 mL) at 0° C. The reaction was stirred for 2 hours at room temperature at which time 5 drops of methanol were added. The reaction mixture was concentrated in vacuo, and the resulting residue dissolved in methylene chloride/methanol then adsorbed on silica gel (1.0 g) and purified by column chromatography eluting with a gradient solvent of 10% to 15% ethyl acetate/hexanes to yield 341 mg (99%) of the desired product as a clear, colorless oil which solidified on standing; $^1$H NMR (CDCl$_3$, 300 MHz) δ 0.12 (d, J=1.5 Hz, 6H), 0.92 (s, 9H), 3.05 (b s, 5H), 3.16 (t, J=11.0 Hz, 1H) 3.44 (d, J=13.7 Hz, 1H), 3.81-3.83 (m, 1H), 4.44-4.50 (m, 1H).

Example 10 trans 5-Methoxy-1,2-dithian-4-ol

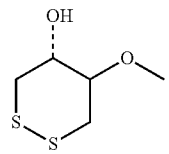

To a solution of (4S,5S)-1,2-dithiane-4,5-diol (0.8 g, 5.26 mmol) in dry tetrahydrofuran (150 mL) was added sodium hydride (NaH, 60%, 0.32 g, 7.9 mmol) at 0° C., stirred the reaction mixture for 15 minutes. Methyl iodide (0.49 mL, 7.9 mmol) was then added dropwise and the reaction mixture was stirred at room temperature for 12 hours. The reaction mixture was then quenched with dilute hydrochloric acid, poured into cold water and extracted with ethyl acetate (3×200 mL). The organic extracts were washed with water, dried over anhydrous Na$_2$SO$_4$, filtered and concentrated at reduced pressure to give the crude compound was purified by column chromatography on silica gel (100-200 mesh) eluting with 20% (v/v) ethyl acetate in hexanes. The title racemic compound was obtained as a white solid (0.6 g, yield 68%) and separated from the dimethylated compound, 4,5-dimethoxy-1,2-dithiane (150 mg). $^1$H NMR (DMSO-d$_6$, 400 MHz): δ 5.32 (m, br, 1H), 3.49 (m, 3H), 3.47-3.40 (m, 1H), 3.33-3.29 (m, 1H), 3.09-3.04 (m, 2H), 2.78-2.70 (m, 2H); LCMS m/e: 135 [M+H−32]$^+$.

Example 11 trans 5-Methoxy-1,2-dithian-4-yl methanesulfonate

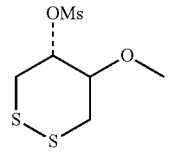

To a solution of trans 5-methoxy-1,2-dithian-4-ol (0.6 g, 3.61 mmol) and triethylamine (0.65 mL, 4.69 mmol) in dichloromethane was added methanesulfonyl chloride (0.28 mL, 3.61 mmol) at 0° C. and the reaction was stirred for 2 hours. The mixture was then poured into water and was extracted with ethyl acetate (3×200 mL). The combined extracts were washed with water, dried over anhydrous Na$_2$SO$_4$, filtered and concentrated at reduced pressure to produce the title racemic compound as a white solid (0.48 g, yield 55%). $^1$H NMR (DMSO-d$_6$, 400 MHz): δ 4.58-4.52 (m, 1H), 3.52-3.41 (m, 2H), 3.37 (s, 3H), 3.35-3.30 (m, 2H), 3.21 (s, 3H), 2.92-2.86 (m, 1H).

Example 12 trans 5-(Benzyloxy)-1,2-dithian-4-ol

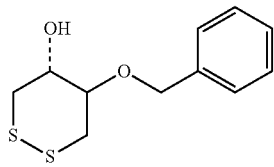 [SMILES: O[C@H]1CSSCC1OCc1ccccc1]

To a solution of (4S,5S)-1,2-dithiane-4,5-diol (0.7 g, 4.6 mmol) in dry N,N dimethylformamide (25 mL) was added sodium hydride (60%, 0.24 g, 5.9 mmol) at 0° C. The reaction mixture was stirred for 20 minutes followed by addition of benzyl bromide (0.66 mL, 5.6 mmol) dropwise and then left to stir at room temperature for 12 hours. The reaction mixture was then quenched with dilute hydrochloric acid and poured into water. The aqueous mixture was extracted with ethyl acetate (3×300 mL), washed with water, dried over anhydrous $Na_2SO_4$, filtered and concentrated at reduced pressure. The crude compound was purified by column chromatography on silica gel (100-200 mesh) eluting with 20% (v/v) ethyl acetate in hexanes to give the title compound as white solid (500 mg, yield 46%) separated from 4,5-dibenzyl-1,2-dithiane compound (180 mg). $^1$H NMR (DMSO-$d_6$, 400 MHz): δ 7.38-7.31 (m, 4H), 7.28 (d, J=6.9 Hz, 1H), 5.37 (d, J=4.9 Hz, 1H), 4.68-4.59 (m, 2H), 3.56-3.54 (m, 1H), 3.35-3.32 (m, 2H), 3.14-3.10 (m, 1H), 2.80-2.74 (m, 2H); LCMS m/e: 243 [M+1]$^+$.

Example 13 trans 5-(Benzyloxy)-1,2-dithian-4-yl methanesulfonate

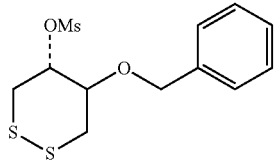

To a solution of trans 5-(benzyloxy)-1,2-dithian-4-ol (0.5 g, 2.07 mmol) and triethylamine (0.37 mL, 2.68 mmol) in dichloromethane was added methanesulfonyl chloride (0.16 mL, 2.07 mmol) at 0° C. The reaction mixture was stirred for 3 hours at room temperature and then carefully poured into water. The aqueous mixture was extracted with ethyl acetate (3×200 mL) and the combined organic extracts were washed with water, dried over anhydrous $Na_2SO_4$, filtered and concentrated at reduced pressure to furnish the title compound as a white solid (220 mg, yield 75%). $^1$H NMR (DMSO-$d_6$, 400 MHz): δ 7.38-7.29 (m, 5H), 4.71-4.60 (m, 2H), 3.68-3.65 (m, 1H), 3.64-3.60 (m, 1H), 3.59-3.52 (m, 1H), 3.49-3.40 (m, 2H), 3.11 (s, 3H), 2.99-2.96 (m, 1H); LCMS m/e: 321 [M+1]$^+$.

Example 14 cis-5-tert-Butyldimethylsilyloxy-1,2-dithiane-4-ol

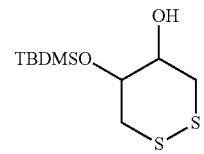 [SMILES: CC(C)(C)[Si](C)(C)OC1CSSCC1O]

To a solution of cis-1,2-dithiane-4,5-diol (5.0 g, 0.03 mol), imidazole (3.14 g, 0.05 mol) and N,N dimethylformamide (25 mL) at 0° C. was added a solution of tert-butyldimethylsilyl chloride (5.96 g, 0.040 mol) in N,N dimethylformamide (15 mL) over a period of 5 minutes. The reaction was then stirred for 20 hours at room temperature. The reaction mixture was concentrated in vacuo and the resulting mixture was dissolved in methylene chloride/methanol, adsorbed on silica gel (3.0 g) and purified by column chromatography eluting with a gradient solvent of 2% to 5% ethyl acetate/hexanes to yield 7.77 g (99%) of the desired product as a clear, colorless oil; $^1$H NMR (CDCl$_3$, 300 MHz) δ 0.12 (d, J=3.8 Hz, 6H), 0.92 (s, 9H), 2.78 (br s, 1H), 2.82-3.70 (m, 4H), 3.58-3.70 (m, 2H).

Example 15 cis 5-Hydroxy-1,2-dithian-4-yl benzoate

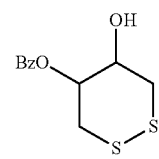

To solution of (4S,5R)-1,2-dithiane-4,5-diol (1 g, 6.57 mmol), and benzoyl chloride (0.84 mL, 7.23 mmol) in mixture of dichloromethane (15 mL) and N,N dimethylformamide (15 mL) were added triethylamine (1 mL, 7.23 mmol) and 4-dimethylaminopyridine (250 mg, 1.64 mmol) at 0° C. and stirred for 1 hour. The mixture was then poured into water and was extracted with ethyl acetate (3×400 mL). The combined extracts were washed with water, dried over anhydrous $Na_2SO_4$, filtered and concentrated at reduced pressure to give the crude compound which was purified by column chromatography on silica gel (100-200 mesh) eluting with 20% (v/v) ethyl acetate in hexanes to give the title compound as colorless solid (1.1 g, yield 65%) separated from the dibenzoylated compound 4,5-dibenzoate 1,2-dithiane (300 mg). $^1$H-NMR (CDCl$_3$, 400 MHz): δ 8.07 (d, J=8.0 Hz, 2H), 7.69-7.66 (m, 1H), 7.57-7.52 (m, 2H), 5.53-5.52 (m, 1H), 5.25 (m, 1H), 3.94 (m, 1H), 3.37-3.27 (m, 3H), 3.15 (s, 1H); LCMS m/e: 135 [M+H−32]$^+$.

Example 16 cis-4-tert-Butyldimethylsilyl)oxy)-1,2-dithian-4-yl methanesulfonate

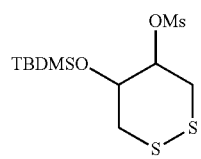 [SMILES: CC(C)(C)[Si](C)(C)OC1CSSCC1OS(C)(=O)=O]

To a solution of cis-tert-butyldimethylsilyloxy-5-hydroxy-1,2-dithiane (858 mg, 3.22 mmol), 2,6-lutidine (0.63 mg, 5.41 mmol), diisopropylethylamine (1.43 mL, 8.19 mmol) and methylene chloride (20 mL) at 0° C. was slowly added methanesulfonyl chloride (0.42 mL, 5.46 mmol). The reaction mixture was stirred at 0° C. for 30 minutes at which time 5 drops of methanol were added to quench the reaction. The reaction mixture was diluted with 15 mL of methylene chloride, washed with 1N HCl (3×) and brine (1×), dried over MgSO$_4$ and then concentrated in vacuo, The resulting residue was co-evaporated with toluene (2×) and dried under vacuum to yield 1.18 g (100%) of the desired product as a clear, colorless oil; $^1$H NMR (CDCl$_3$, 300 MHz) δ 0.12 (d, J=7 Hz, 6H), 0.92 (s, 9H), 2.5-4.3 (br m, 5H), 3.07 (br s, 3H), 4.80-5.00 (br s, 1H).

Example 17 cis 5-((Methylsulfonyl)oxy)-1,2-dithian-4-yl benzoate

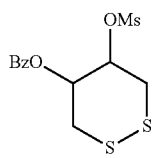

To a solution of cis 5-hydroxy-1,2-dithian-4-yl benzoate (2 g, 7.81 mmol) and triethylamine (1.6 mL, 11.71 mmol) in dichloromethane was added methanesulfonyl chloride (0.66 mL, 8.6 mmol) at 0° C. The reaction mixture was stirred for 2 hours at room temperature and then was poured into water. The mixture was extracted with ethyl acetate (3×300 mL) and the combined extracts were washed with water, dried over anhydrous Na$_2$SO$_4$, filtered and concentrated at reduced pressure to produce the title compound as colorless solid (1.8 g, yield 70%). $^1$H-NMR (CDCl$_3$, 400 MHz): δ 8.07 (d, J=8.0 Hz, 2H), 7.71-7.66 (m, 1H), 7.58-7.53 (m, 2H), 5.28-5.22 (m, 1H), 3.92-3.98 (m, 2H), 3.36-3.32 (m, 3H), 2.93 (s, 3H); LCMS m/e: 135 [M+H−32]$^+$.

Example 18 cis 5-Methoxy-1,2-dithian-4-ol

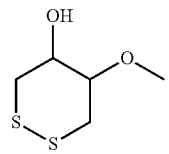

To a solution of (4S,5R)-1,2-dithiane-4,5-diol (0.5 g, 3.29 mmol) in dry tetrahydrofuran (20 mL) was added sodium hydride (60%, 0.19 g, 4.94 mmol) at 0° C., and the reaction mixture was stirred for 15 minutes. Methyl iodide (0.3 mL) was then added dropwise and the reaction mixture was stirred at room temperature for 12 hours. The reaction mixture was then quenched with dilute hydrochloric acid and poured into cold water. The aqueous layer was extracted with ethyl acetate (3×300 mL) and the organic extracts were washed with water, dried over anhydrous Na$_2$SO$_4$, filtered and concentrated at reduced pressure to give a crude oily compound which was purified by column chromatography on silica gel (100-200 mesh) eluting with 20% (v/v) ethyl acetate in hexanes to give the title compound as a white solid (160 mg, yield 30%) separated from the dimethylated compound, 4,5 dimethoxy-1,2-dithiane (50 mg). $^1$H NMR (DMSO-d$_6$, 400 MHz) δ 5.03 (m, br, 1H), 3.80 (m, br, 1H), 3.38 (m, 2H), 3.33 (s, 3H), 3.29 (m, 1H), 2.98-2.95 (m, 2H); LCMS m/e: 135 [M+H−32]$^+$.

Example 19 cis 5-Methoxy-1,2-dithian-4-yl methanesulfonate

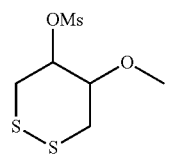

To a solution of 5-methoxy-1,2-dithian-4-ol (0.16 g, 0.96 mmol) and triethylamine (0.17 mL, 1.26 mmol) in dichloromethane was added methanesulfonyl chloride (0.082 mL, 1.06 mmol) at 0° C. The reaction mixture was allowed to warm up to room temperature and stirred for 2 hours. The mixture was then poured into water and extracted with ethyl acetate (3×300 mL). The combined extracts were washed with water, dried over anhydrous Na$_2$SO$_4$, filtered and concentrated at reduced pressure to furnish the title compound a (90 mg, yield 40%) as a colorless solid. $^1$H NMR (DMSO-d$_6$, 400 MHz): δ 4.56-4.53 (m, 1H), 3.50-3.41 (m, 2H), 3.37 (s, 3H), 3.36-3.32 (m, 2H), 3.19 (s, 3H), 2.92-2.86 (m, 1H).

Example 20 cis 5-(Benzyloxy)-1,2-dithian-4-ol

To a solution of (4S,5R)-1,2-dithiane-4,5-diol (1.0 g, 6.57 mmol) in dry N,N dimethylformamide (30 mL) was added NaH (60%, 0.34 g, 8.55 mmol) at 0° C., and the reaction mixture was stirred for 20 minutes before the addition of benzyl bromide (0.93 mL, 7.89 mmol) dropwise. The reaction mixture was then stirred at room temperature for 12 hours and quenched with dilute hydrochloric acid and poured into water. The aqueous solution was extracted with ethyl acetate (3×300 mL) and the combined extracts were washed with water, dried over anhydrous $Na_2SO_4$, filtered and concentrated at reduced pressure. The crude compound was purified by column chromatography on silica gel (100-200 mesh) eluting with 20% (v/v) ethyl acetate in hexanes to give the title compound as colorless solid (650 mg, yield 44%) separated from 4,5-dibenzyl-1,2-dithiane (200 mg). $^1$H NMR (DMSO-$d_6$, 400 MHz): δ 7.39-7.30 (m, 5H), 5.16 (s, 1H), 4.64-4.54 (m, 2H), 3.86-3.66 (m, 2H), 3.22-3.19 (m, 1H), 3.06-3.10 (m, 3H); LCMS m/e: 243 [M+1]$^+$.

Example 21 cis 5-(Benzyloxy)-1,2-dithian-4-yl methanesulfonate

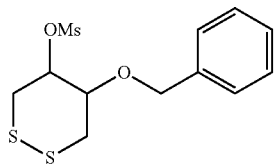 [SMILES: CS(=O)(=O)OC1CSSCC1OCc1ccccc1]

To a solution of cis 5-(benzyloxy)-1,2-dithian-4-ol (0.65 g, 2.68 mmol) and triethylamine (0.78 mL, 3.49 mmol) in dichloromethane was added methanesulfonyl chloride (0.22 mL, 2.68 mmol) at 0° C. The reaction mixture was stirred for 3 hours at room temperature and then poured into water. The aqueous mixture was extracted with ethyl acetate (3×200 mL) and the combined extracts were washed with water, dried over anhydrous $Na_2SO_4$, filtered and concentrated at reduced pressure to produce the title compound as a colorless solid (360 mg, yield 43%). $^1$H NMR (DMSO-$d_6$, 400 MHz): δ 7.36-7.28 (m, 5H), 4.70-4.60 (m, 2H), 3.60-3.62 (m, 1H), 3.50-3.48 (m, 1H), 3.42-3.38 (m, 2H), 3.32-3.25 (m, 1H), 3.10 (s, 3H), 2.97-2.95 (m, 1H); LCMS m/e: 321 [M+1]$^+$.

Example 22

3-Iodo-1H-pyrazolo[3,4-d]pyrimidin-4-amine

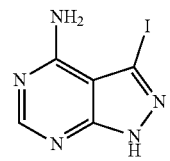 [SMILES: Nc1ncnc2[nH]nc(I)c12]

To a mixture of 1H-pyrazole[3,4-d]pyrimidine-4-amine (5 g, 37.03 mmol) in N,N dimethylformamide (40 mL) was added N-iodosuccinimide (12.5 g, 55.6 mmol) and the reaction mixture was heated at 80° C. for 12 hours under argon atmosphere. The resultant solid was filtered, rinsed with cold ethanol and dried in vacuum overnight to give the product as a pale brown solid (9 g, yield 93.7%). $^1$H-NMR (DMSO-$d_6$, 400 MHz): δ 13.80 (s, 1H), 8.17 (s, 1H), 7.00 (s, 2H); MS (ES) m/e 262 [M+1]$^+$.

Example 23

3-Phenyl-1H-pyrazolo[3,4-d]pyrimidin-4-amine

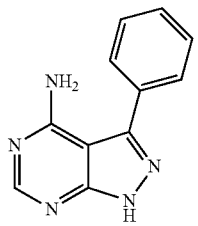 [SMILES: Nc1ncnc2[nH]nc(-c3ccccc3)c12]

To a stirred suspension of 3-iodo-1H-pyrazolo[3,4-d]pyrimidin-4-amine (2 g, 7.66 mmol), phenylboronic acid (1.12 g, 9.18 mmol) and $K_3PO_4$ (2.4 g, 11.3 mmol) in degassed N,N dimethylformamide:water (3:2, 20 mL), was added 1,1' (bisdiphenylphosphino)ferrocenepalladium(II) dichloride (Pd(dppf)Cl$_2$ (1.3 g, 1.15 mmol). The reaction mixture was purged with argon and heated at 120° C. for 18 hours. After cooling, the reaction mixture was filtered through celite and washed with ethyl acetate. The organic layer was poured into water (100 mL), extracted with ethyl acetate (3×400 mL) and the combined extracts were washed again with water. The combined organic layer was dried over anhydrous $Na_2SO_4$ filtered and evaporated to dryness to furnish the desired crude product which was purified by column chromatography over silica gel (100-200 mesh size) as a stationary phase and 5% (v/v) methanol in dichloromethane as eluent to give the title compound as a colorless solid (0.85 g, yield 53%). $^1$H NMR (DMSO-$d_6$, 400 MHz) δ 3.59 (s, 1H), 8.22 (s, 1H), (d, J=7.2 Hz, 2H), 7.55-7.46 (m, 3H), 6.50 (br s, 2H); MS (ES) m/e 212 [M+1]$^+$.

Example 24

3-(4-Chlorophenyl)-1H-pyrazolo[3,4-d]pyrimidin-4-amine

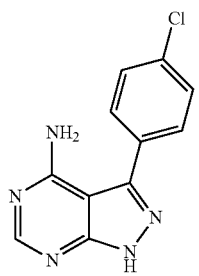 [SMILES: Nc1ncnc2[nH]nc(-c3ccc(Cl)cc3)c12]

To a stirred suspension of 3-iodo-1H-pyrazolo[3,4-d]pyrimidin-4-amine (2 g, 7.662 mmol), 4-chlorophenylboronic acid (1.44 g, 9.18 mmol) and $K_3PO_4$ (2.4 g, 11.3 mmol) in degassed N,N dimethylformamide:water (3:2, 20 mL), was added 1,1' (bisdiphenylphosphino)ferrocenepalladium(II) dichloride (Pd(dppf)Cl$_2$ (1.3 g, 1.15 mmol). The reaction mixture was flushed with argon and heated at 120° C. for 18 hours. After cooling, the reaction mixture was filtered through celite and washed with excess ethyl acetate. The organic layer was poured into water (100 mL), extracted with ethyl acetate (3×400 mL) and washed with water. The combined organic layer was dried over anhydrous $Na_2SO_4$ filtered and solvents were evaporated to furnish the desired crude product. The pure product was obtained by column chromatography over silica gel (100-200 mesh) as a stationary phase and 5% (v/v) methanol in dichloromethane as eluent to give the title compound as a colorless solid (0.49 g, yield 27%). $^1$H NMR (DMSO-do, 400 MHz) δ 13.64 (s, 1H), 8.22 (s, 1H), 7.68 (d, J=8.4 Hz, 2H), 7.59 (d, J=8.4 Hz, 2H), 6.8 (br s, 2H); MS (ES) m/e 246 [M+1]$^+$.

Example 25

3-(4-Methoxyphen 1)-1H-pyrazolo[3,4-d]pyrimidin-4-amine

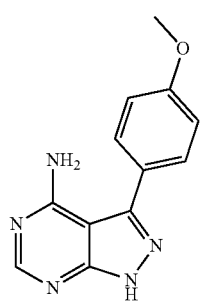 [SMILES: COc1ccc(-c2n[nH]c3ncnc(N)c23)cc1]

To a stirred suspension of 3-iodo-1H-pyrazolo[3,4-d]pyrimidin-4-amine (2 g, 7.66 mmol), 4-methoxyphenylboronic acid (1.44 g, 9.18 mmol) and $K_3PO_4$ (2.0 g, 7.66 mmol) in degassed N,N dimethylformamide:water (3:2, 20 mL), was added 1,1' (bisdiphenylphosphino)ferrocenepalladium(II) dichloride (Pd(dppf)Cl$_2$ (1.3 g, 1.15 mmol). The reaction mixture was flushed with argon and heated at 120° C. for 18 hours. After cooling, the reaction mixture was filtered through celite and washed with excess ethyl acetate. The organic layer was poured into water (100 mL), extracted with ethyl acetate (3×400 mL) washed with water. The combined organic layer was then dried over anhydrous $Na_2SO_4$ filtered and evaporated to dryness to furnish the desired crude product. The title compound was obtained by column chromatography over silica gel (100-200 mesh size) as a stationary phase and 5% (v/v) methanol in dichloromethane as eluent as a colorless solid (0.75 g, yield 42%). $^1$H NMR (DMSO-d$_6$, 400 MHz): δ 13.58 (s, 1H), 8.22 (s, 1H), 7.48-7.44 (m, 1H), 7.25-7.19 (m, 2H), 7.06-7.03 (m, 1H), 3.83 (s, 3H); MS (ES) m/e 242 [M+1]$^+$.

Example 26

3-(4-Phenoxyphenyl)-1H-pyrazolo[3,4-d]pyrimidin-4-amine

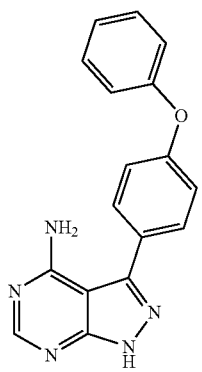 [SMILES: Nc1ncnc2[nH]nc(-c3ccc(Oc4ccccc4)cc3)c12]

To a stirred suspension of 3-iodo-1H-pyrazolo[3,4-d]pyrimidin-4-amine (0.1 g, 0.38 mmol), (4-phenoxyphenyl)boronic acid (0.09 g, 0.42 mmol) and $K_3PO_4$ (0.12 g, 0.56 mmol) in degassed N,N dimethylformamide:water (3:2, 2 mL), was added 1,1' (bisdiphenylphosphino)ferrocenepalladium(II) dichloride Pd(dppf)Cl$_2$ (0.09 g, 0.12 mmol). The reaction mixture was flushed with argon and heated at 120° C. for 5 hours. After cooling, the reaction mixture was filtered through celite and washed with excess ethyl acetate. The organic layer was poured into water (100 mL), extracted with ethyl acetate (3×200 mL) and washed with water. The organic layer was dried over anhydrous $Na_2SO_4$ filtered and evaporated to dryness to furnish the crude product. The title compound was obtained by column chromatography over silica gel (100-200 mesh size) as a stationary phase and 5% (v/v) methanol in dichloromethane as eluent to give the product as a colorless solid (0.03 g, yield 25.8%). $^1$H NMR (DMSO-do, 400 MHz) δ 3.54 (s, 1H), 8.21 (s, 1H), 7.66 (d, J=8.0 Hz, 2H), 7.43 (t, J=8.0 Hz, 2H), 7.20-7.12 (m, 5H); LCMS m/e: 304 [M+1]$^+$.

Example 27 trans 3-((4-Amino-3-phenyl-1H-pyrazolo[3,4-d]pyrimidin-1-yl)methyl)-1,2-dithiolan-4-yl benzoate)

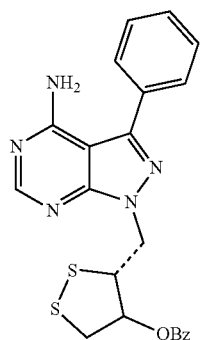

To a solution of 3-phenyl-1H-pyrazolo[3,4-d]pyrimidin-4-amine (0.3 g, 1.42 mmol) in dry N,N dimethylformamide was added $Cs_2CO_3$ (0.7 g, 2.14 mmol) stirred for 10 minutes followed by slow addition of trans 5-((methylsulfonyl)oxy)-1,2-dithian-4-yl benzoate (0.94 g, 2.81 mmol) at room temperature. The reaction mixture was stirred and heated at 80° C. for 2.5 hours. After cooling, the mixture was carefully poured into cold water and extracted with ethyl acetate (3×200 mL). The combined extracts were washed with water, dried over anhydrous $Na_2SO_4$, filtered and concentrated at reduced pressure. The pure product was obtained by column chromatography on silica gel (100-200 mesh) eluting with 1-2% (v/v) methanol in dichloromethane as a pale brown solid (190 mg, yield 30%). MS (ES) m/e 450 [M+1]$^+$.

Example 28 trans 3-((4-Amino-3-phenyl-1H-pyrazolo[3,4-d]pyrimidin-1-yl)methyl)-1,2-dithiolan-4-ol

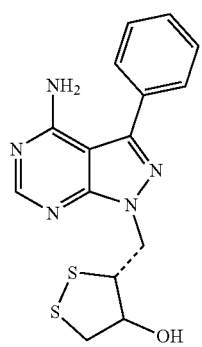

To a solution of trans 3-((4-amino-3-(4-phenoxyphenyl)-1H-pyrazolo[3,4-d]pyrimidin-1-yl)methyl)-1,2-dithiolan-4-yl benzoate (0.18 g, 0.40 mmol) in tetrahydrofuran (15 mL) was added 10% LiOH (5 mL) and was stirred for 4 hours at room temperature. The reaction mixture was then poured into water, acidified with saturated citric acid and extracted with ethyl acetate (3×200 mL). The combined organic extracts were dried over anhydrous $Na_2SO_4$ filtered and concentrated at reduced pressure. The pure product was obtained by column chromatography on silica gel (100-200 mesh) eluting with 0.5% (v/v) methanol in dichloromethane to give the title compound as a pale brown solid (70 mg, yield 50%). $^1$H NMR (DMSO-d$_6$, 400 MHz) δ 8.27 (s, 1H), 7.69 (d, J=7.6 Hz, 2H), 7.58-7.43 (m, 3H), 5.52 (d, J=4.4 Hz, 1H), 4.63-4.49 (m, 3H), 3.99 (bs, 1H), 3.45-3.37 (m, 1H), 3.08 (dd, J$_1$=11.6 Hz, J$_2$=3.6 Hz, 1H); MS (ES) m/e 346 [M+1]$^+$.

Example 29 trans 3-((4-Amino-3-(4-chlorophenyl)-1H-pyrazolo[3,4-d]pyrimidin-1-yl)methyl)-1,2-dithiolan-4-yl benzoate

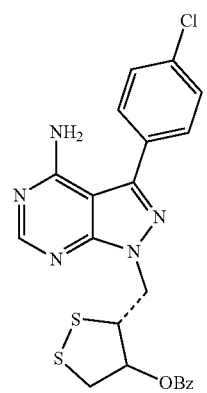

To a solution of 3-(4-chlorophenyl)-1H-pyrazolo[3,4-d]pyrimidin-4-amine (0.4 g, 1.63 mmol) in dry N,N dimethylformamide was added $Cs_2CO_3$ (1.0 g, 3.26 mmol) stirred for 10 minutes, followed by the addition of trans 5-((methylsulfonyl)oxy)-1,2-dithian-4-yl benzoate (1.0 g, 3.26 mmol). The reaction mixture was heated at 80° C. for 2.5 hours and was poured into cold water after cooling. The aqueous mixture extracted with ethyl acetate (3×200 mL), was washed with water, dried over anhydrous $Na_2SO_4$, filtered and concentrated at reduced pressure. The pure product was obtained by column chromatography on silica gel (100-200 mesh) eluting with 1-2% (v/v) methanol in dichloromethane to produce as a pale brown solid (230 mg, yield 29%). $^1$H NMR (DMSO-d$_6$, 400 MHz) δ 8.27 (s, 1H), 7.86 (d, J=7.6 Hz, 2H), 7.65-7.57 (m, 5H), 7.55-7.47 (m, 2H), 6.8 (s br, 2H), 5.81-5.78 (m, 1H), 4.75-4.72 (m, 2H), 4.45-4.42 (m, 1H), 3.72-3.68 (m, 1H), 3.46-3.42 (m, 1H); MS (ES) m/e 485 [M+1]$^+$.

Example 30 trans 3-((4-Amino-3-(4-chlorophenyl)-1H-pyrazolo[3,4-d]pyrimidin-1-yl)methyl)-1,2-dithiolan-4-ol

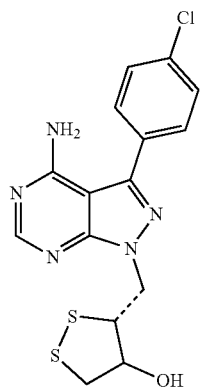

To a solution of trans 3-((4-amino-3-(4-chlorophenyl)-1H-pyrazolo[3,4-d]pyrimidin-1-yl)methyl)-1,2-dithiolan-4-yl benzoate (0.2 g, 0.41 mmol) in tetrahydrofuran (15 mL) was added 10% LiOH (6 mL) at room temperature. After stirring for 4 hours, the reaction mixture was poured into water, acidified with saturated citric acid and extracted with ethyl acetate (3×200 mL) and the combined organic extracts were dried over anhydrous $Na_2SO_4$ concentrated at reduced pressure. The pure product was obtained by column chromatography on silica gel (100-200 mesh) eluting with 0.5% (v/v) methanol in dichloromethane to give the title compound as pale brown solid (90 mg, yield 57%). $^1$H NMR (DMSO-$d_6$, 400 MHz) δ 8.27 (s, 1H), 7.70 (d, J=8.4 Hz, 2H), 7.61 (d, J=8.4 Hz, 2H), 5.53 (d, J=4.8 Hz, 2H), 4.59-4.52 (m, 3H), 4.01-3.92 (m, 1H), 3.44-3.40 (m, 1H), 3.09-3.05 (m, 1H); MS (ES) m/e 380 [M+1]$^+$.

Example 31 trans 3-((4-amino-3-(4-methoxyphenyl)-1H-pyrazolo[3,4-d]pyrimidin-1-yl)methyl)-1,2-dithiolan-4-yl benzoate

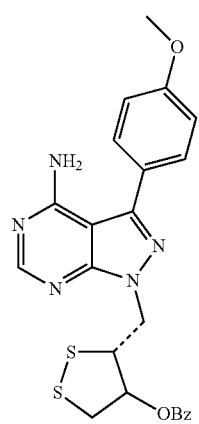

To a solution of 3-(4-methoxyphenyl)-1H-pyrazolo[3,4-d]pyrimidin-4-amine (0.4 g, 1.65 mmol) in dry N,N dimethylformamide was added $Cs_2CO_3$ (0.81 g, 2.48 mmol) and was stirred for 10 minutes followed by the addition of trans 5-((methylsulfonyl)oxy)-1,2-dithian-4-yl benzoate (1.1 g, 3.29 mmol). The reaction mixture was heated with stirring at 80° C. for 2.5 hours, cooled and then quenched with cold water. The aqueous mixture was extracted with ethyl acetate (3×300 mL) and the combined extracts were washed with water, dried over anhydrous $Na_2SO_4$, filtered and concentrated at reduced pressure. The pure product was obtained by column chromatography on silica gel (100-200 mesh) eluting with 1-2% (v/v) methanol in dichloromethane to produce as a pale brown solid (240 mg, yield 31%). MS (ES) m/e 480 [M+1]$^+$.

Example 32 trans 3-((4-Amino-3-(4-methoxyphenyl)-1H-pyrazolo[3,4-d]pyrimidin-1-yl)methyl)-1,2-dithiolan-4-ol

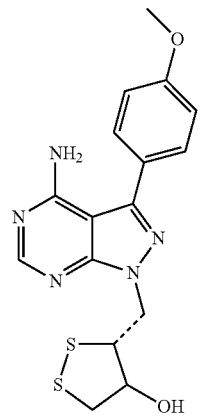

To a solution of trans 3-((4-amino-3-(4-methoxyphenyl)-1H-pyrazolo[3,4-d]pyrimidin-1-yl)methyl)-1,2-dithiolan-4-yl benzoate (0.22 g, 0.45 mmol) in tetrahydrofuran (20 mL) was added 10% LiOH (8 mL) at room temperature and the mixture was stirred for 4 hours. The reaction mixture was then poured into water, acidified with saturated citric acid and extracted with ethyl acetate (3×200 mL). The combined organic extracts were dried over anhydrous $Na_2SO_4$, filtered and concentrated at reduced pressure to give the crude product which was purified by column chromatography on silica gel (100-200 mesh) eluting with 0.5% (v/v) methanol in dichloromethane to give the title compound as pale brown solid (80 mg, yield 47%). $^1$H NMR 400 MHz (DMSO-$d_6$, 400 MHz) δ 8.27 (s, 1H), 7.47 (d, J=7.6 Hz, 2H), 7.26-7.20 (m, 3H), 7.07-7.05 (m, 1H), 5.53 (d, J=4.8 Hz, 2H), 4.63-4.48 (m, 3H), 4.01-3.96 (m, 1H), 3.83 (s, 3H), 3.45-3.40 (m, 1H), 3.09-3.06 (m, 1H); MS (ES) m/e 376 [M+1]$^+$.

Example 33

(3S,4R)-3-((4-Amino-3-(4-methoxyphenyl)-1H-pyrazolo[3,4-d]pyrimidin-1-yl)methyl)-1,2-dithiolan-4-ol and (3R,4S)-3-((4-Amino-3-(4-methoxyphenyl)-1H-pyrazolo[3,4-d]pyrimidin-1-yl)methyl)-1,2-dithiolan-4-ol The two enantiomers of trans 3-((4-amino-3-(4-methoxyphenyl)-1H-pyrazolo[3,4-d]pyrimidin-1-yl)methyl)-1,2-dithiolan-4-ol were separated by chiral HPLC techniques as peak 1 retention time 11.7 minutes (5 mg) and peak 2 retention time 19.7 minutes (7 mg) by following chiral HPLC conditions. Column: Chiralpak-IA (250*4.6*5.0 g); mobile phase-A: 0.1% diethylamine in n-hexanes; mobile phase-B: ethanol; mobile phase C:isopropanol:dichloromethane (90:10); method-isocratic: 10:80:10 (A:B:C); flow rate: 15.0 mL/min; Column temp: ambient; diluent: mobile phase; sample loading: 30 mg/injection; run time: 35 minutes.

A. Peak 1 Data (3S,4R)-3-((4-Amino-3-(4-methoxyphenyl)-1H-pyrazolo[3,4-d]pyrimidin-1-yl)methyl)-1,2-dithiolan-4-ol

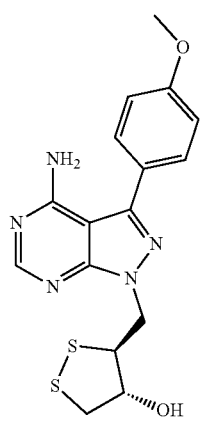 [SMILES: COc1ccc(-c2nn(C[C@@H]3SSC[C@H]3O)c3ncnc(N)c23)cc1]

$^1$H NMR 400 MHz (DMSO-$d_6$, 400 MHz) δ 8.27 (s, 1H), 7.47 (d, J=7.6 Hz, 2H), 7.26-7.20 (m, 3H), 7.07-7.05 (m, 1H), 5.53 (d, J=4.8 Hz, 2H), 4.63-4.48 (m, 3H), 4.01-3.96 (m, 1H), 3.83 (s, 3H), 3.45-3.40 (m, 1H), 3.09-3.06 (m, 1H); MS (ES) m/e 376 [M+1]$^+$.

B. Peak 2 Data (3R,4S)-3-((4-Amino-3-(4-methoxyphenyl)-1H-pyrazolo[3,4-d]pyrimidin-1-yl)methyl)-1,2-dithiolan-4-ol

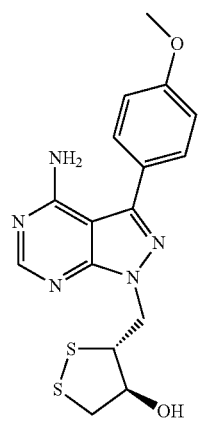 [SMILES: COc1ccc(-c2nn(C[C@H]3SSC[C@@H]3O)c3ncnc(N)c23)cc1]

$^1$H NMR (DMSO-$d_6$, 400 MHz) δ 8.27 (s, 1H), 7.47 (d, J=7.6 Hz, 2H), 7.26-7.20 (m, 3H), 7.07-7.05 (m, 1H), 5.53 (d, J=4.8 Hz, 2H), 4.63-4.48 (m, 3H), 4.01-3.96 (m, 1H), 3.83 (s, 3H), 3.45-3.40 (m, 1H), 3.09-3.06 (m, 1H); MS (ES) m/e 376 [M+1]$^+$.

Example 34 cis 3-((4-Amino-3-(4-methoxyphenyl)-1H-pyrazolo[3,4-d]pyrimidin-1-yl)methyl)-1,2-dithiolan-4-yl benzoate

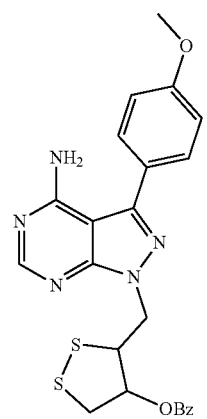

To a solution of 3-(4-methoxyphenyl)-1H-pyrazolo[3,4-d]pyrimidin-4-amine (0.5 g, 2.07 mmol) in dry N,N dimethylformamide was added $Cs_2CO_3$ (1.01 g, 3.12 mmol) and the resultant solution was stirred for 10 minutes followed by the slow addition of cis 5-((methylsulfonyl)oxy)-1,2-dithian-4-yl benzoate (2.07 g, 6.22 mmol). The reaction mixture was heated to 80° C. for 2.5 hours and then after cooling was poured carefully into water. The aqueous mixture was extracted with ethyl acetate (3×300 mL) and the combined extracts were washed with water, dried over anhydrous $Na_2SO_4$, filtered and concentrated at reduced pressure. The pure product was obtained by column chromatography on silica gel (100-200 mesh) eluting with 1-2% (v/v) methanol in dichloromethane to furnish the title compound as a pale brown solid (600 mg, yield 60%). MS (ES) m/e 480 [M+1]$^+$.

Example 35 cis 3-((4-Amino-3-(4-methoxyphenyl)-1H-pyrazolo[3,4-d]pyrimidin-1-yl)methyl)-1,2-dithiolan-4-ol

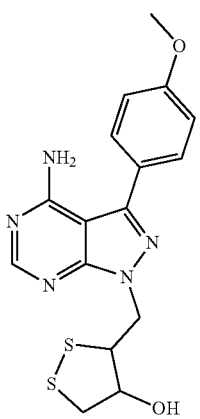 [SMILES: COc1ccc(-c2nn(CC3SSCC3O)c3ncnc(N)c23)cc1]

To a solution of cis 3-((4-amino-3-(4-methoxyphenyl)-1H-pyrazolo[3,4-d]pyrimidin-1-yl)methyl)-1,2-dithiolan-4-yl benzoate (0.6 g, 1.25 mmol) in tetrahydrofuran (20 mL) was added 10% LiOH (10 mL) at room temperature and the reaction mixture was stirred for 4 hours followed by addition of cold water. The reaction mixture was then acidified with saturated citric acid and extracted with ethyl acetate (3×200 mL). The combined organic extracts were dried over anhydrous Na$_2$SO$_4$, filtered and concentrated at reduced pressure. The pure product was obtained by column chromatography on silica gel (100-200 mesh) eluting with 0.5% (v/v) methanol in dichloromethane to give the title compound as a pale brown solid (100 mg crude).

Example 36

(3S,4S)-3-((4-Amino-3-(4-methoxyphenyl)-1H-pyrazolo[3,4-d]pyrimidin-1-yl)methyl)-1,2-dithiolan-4-ol and (3R,4R)-3-((4-amino-3-(4-methoxyphenyl)-1H-pyrazolo[3,4-d]pyrimidin-1-yl)methyl)-1,2-dithiolan-4-ol The two enantiomers were separated as peak 1 retention time 7.6 minutes (10 mg) and peak 2 retention time 9.1 minutes (8 mg) by following chiral HPLC conditions.

Column: Chiralpak-IA (250*4.6*5.0p); mobile phase-A: 0.1% diethylamine in n-hexanes; mobile phase B: isopropanol:dichloromethane (80:20); method-isocratic: 70:30 (A:B); flow rate: 15.0 mL/min; column temp: ambient; diluent: mobile phase; sample loading: 20 mg/injection; runtime: 45 minutes.

A. Peak 1 Data (3S,4S)-3-((4-Amino-3-(4-methoxyphen 1)-1H-pyrazolo[3,4-d]pyrimidin-1-yl)methyl)-1,2-dithiolan-4-ol

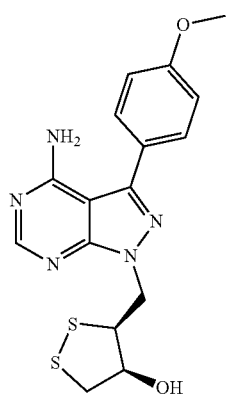 [SMILES: COc1ccc(-c2nn(C[C@@H]3SSC[C@@H]3O)c3ncnc(N)c23)cc1]

$^1$H NMR 400 MHz (DMSO-d$_6$): δ 8.27 (s, 1H), 7.60 (d, J=8.4 Hz, 2H), 7.11 (d, J=8.4 Hz, 2H), 5.66 (d, J=4.8 Hz, 2H), 4.81-4.61 (m, 3H), 4.12-4.07 (m, 1H), 3.83 (s, 3H), 3.43-3.39 (m, 1H), 3.12 (dd, J$_1$=11.6 Hz, J$_2$=3.2 Hz, 1H); MS (ES) m/e 376 [M+1]$^+$.

B. Peak 2 Data (3R,4R)-3-((4-Amino-3-(4-methoxyphenyl)-1H-pyrazolo[3,4-d]pyrimidin-1-yl)methyl)-1,2-dithiolan-4-ol

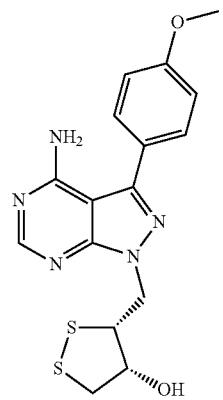 [SMILES: COc1ccc(-c2nn(C[C@H]3SSC[C@H]3O)c3ncnc(N)c23)cc1]

$^1$H NMR 400 MHz (DMSO-d$_6$): δ 8.27 (s, 1H), 7.60 (d, J=8.4 Hz, 2H), 7.11 (d, J=8.4 Hz, 2H), 5.66 (d, J=4.8 Hz, 2H), 4.81-4.61 (m, 3H), 4.12-4.07 (m, 1H), 3.83 (s, 3H), 3.43-3.39 (m, 1H), 3.12 (dd, J$_1$=11.6 Hz, J$_2$=3.2 Hz, 1H); MS (ES) m/e 376 [M+1]$^+$.

Example 37 trans 1-((4-Methoxy-1,2-dithiolan-3-yl)methyl)-3-(4-phenoxyphenyl)-1H-pyrazolo[3,4-d]pyrimidin-4-amine

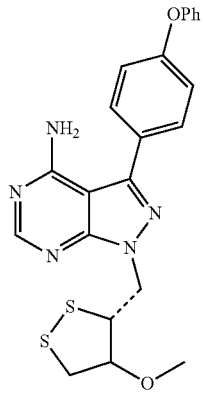

To a solution of 3-(4-phenoxyphenyl)-1H-pyrazolo[3,4-d]pyrimidin-4-amine (0.50 g, 0.16 mmol) in dry N,N dimethylformamide was added Cs$_2$CO$_3$ (96 mg, 0.83 mmol) and stirred for 10 minutes followed by the addition of trans 5-methoxy-1,2-dithian-4-yl-methanesulfonate (0.2 g, 0.3 mmol). The reaction mixture was heated for 2 hours at 80° C. then cooled and poured into cold water. The aqueous solution was extracted with ethyl acetate (3×150 mL) and the combined extracts were washed with water, dried over anhydrous Na$_2$SO$_4$, filtered and concentrated at reduced pressure. The pure product was obtained by column chromatography on silica gel (100-200 mesh) eluting with 1-2% (v/v) methanol in dichloromethane to furnish the title compound as a pale brown solid (15 mg, yield 18%). $^1$H NMR (DMSO-d$_6$, 400 MHz): δ 8.27 (s, 1H), 7.67 (d, J=8.0 Hz, 2H), 7.45-7.42 (m, 2H), 7.22-7.12 (m, 5H), 4.60-4.57 (m, 2H), 4.24 (m, 1H), 4.13 (m, 1H), 3.49-3.45 (m, 1H), 3.23-3.20 (m, 1H), 3.12 (s, 3H); LCMS m/e: 452 [M+1]$^+$.

Example 38 cis 1-((4-Methoxy-1,2-dithiolan-3-yl)methyl)-3-(4-phenoxyphenyl)-1H-pyrazolo[3,4-d]pyrimidin-4-amine

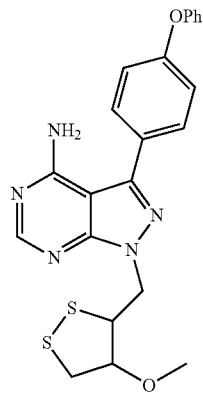 [SMILES: COC1CSSC1Cn1nc(-c2ccc(Oc3ccccc3)cc2)c2c(N)ncnc21]

To a solution of 3-(4-phenoxyphenyl)-1H-pyrazolo[3,4-d]pyrimidin-4-amine (30 mg, 0.099 mmol) in dry dimethylformamide was added $Cs_2CO_3$ (48 mg, 0.149 mmol) and was stirred for 15 minutes followed by the addition of cis 5-methoxy-1,2-dithian-4-yl methanesulfonate (0.12 g, 0.49 mmol). The reaction mixture was heated for 2 hours at 80° C., cooled and poured into water. The aqueous solution was extracted with ethyl acetate (3×150 mL) and the combined extracts were washed with water, dried over anhydrous $Na_2SO_4$, filtered and concentrated at reduced pressure. The pure product was obtained by column chromatography on silica gel (100-200 mesh) eluting with 1-2% (v/v) methanol in dichloromethane to furnish the title compound as a pale brown solid (8 mg, yield 19%). $^1$H NMR (DMSO-d$_6$, 400 MHz) δ 8.26 (s, 1H), 7.68 (d, J=8.8 Hz, 2H), 7.45-7.41 (m, 2H), 7.20-7.11 (m, 5H), 4.80-4.76 (m, 1H), 4.68-4.62 (m, 1H), 4.46-4.44 (m, 1H), 4.28-4.23 (m, 1H), 3.50-3.31 (m, 2H), 3.36 (s, 3H); LCMS m/e: 452 [M+1]$^+$.

Example 39 trans 1-((4-(Benzyloxy)-1,2-dithiolan-3-yl)methyl)-3-(4-phenoxyphenyl)-1H-pyrazolo[3,4-d]pyrimidin-4-amine

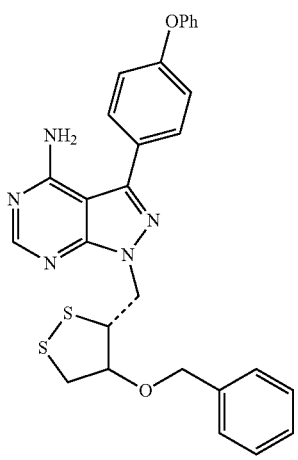

To a solution of 3-(4-phenoxyphenyl)-1H-pyrazolo[3,4-d]pyrimidin-4-amine (40 mg, 0.132 mmol) in dry N,N dimethylformamide (10 mL) was added $Cs_2CO_3$ (65 mg, 0.19 mmol) and was stirred for 10 minutes followed by the addition of trans 5-((methylsulfonyl)oxy)-1,2-dithian-4-yl benzoate (0.21 g, 0.66 mmol). The reaction mixture was heated for 2 hours at 80° C., then cooled, and poured into water. The aqueous solution was extracted with ethyl acetate (3×200 mL) and the combined extracts were washed with water, dried over anhydrous $Na_2SO_4$, filtered and concentrated at reduced pressure. The pure product was obtained by column chromatography on silica gel (100-200 mesh) eluting with 1-2% (v/v) methanol in dichloromethane to produce as a pale brown solid (10 mg, yield 15%). $^1$H NMR (DMSO-d$_6$, 400 MHz) δ 8.24 (s, 1H), 7.65 (d, J=8.8 Hz, 2H), 7.46-7.42 (m, 2H), 7.22-7.08 (m, 10H), 4.58-4.55 (m, 2H), 4.38 (m, 1H), 4.33 (s, 1H), 4.24-4.20 (m, 1H), 3.53-3.49 (m, 1H), 3.29-3.26 (m, 1H); LCMS m/e: 528 [M+1]$^+$.

Example 40 cis 1-((4-(Benzyloxy)-1,2-dithiolan-3-yl)methyl)-3-(4-phenoxyphenyl)-1H-pyrazolo[3,4-d]pyrimidin-4-amine

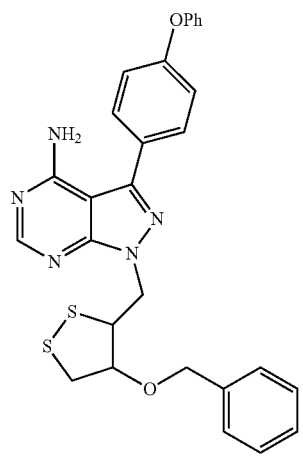 [SMILES: Nc1ncnc2c1c(-c1ccc(Oc3ccccc3)cc1)nn2CC1SSCC1OCc1ccccc1]

To a solution of 3-(4-phenoxyphenyl)-1H-pyrazolo[3,4-d]pyrimidin-4-amine (40 mg, 0.132 mmol) in dry N,N dimethylformamide (10 mL) was added $Cs_2CO_3$ (65 mg, 0.19 mmol) and was stirred for 10 minutes followed by the addition of cis 5-((methylsulfonyl)oxy)-1,2-dithian-4-yl benzoate (0.21 g, 0.66 mmol). The reaction mixture was heated for 2 hours 80° C., cooled and poured into water. The aqueous solution was extracted with ethyl acetate (3×200 mL) and the combined extracts were washed with water, dried over anhydrous $Na_2SO_4$, filtered and concentrated at reduced pressure. The pure product was obtained by column chromatography on silica gel (100-200 mesh) eluting with 1-2% (v/v) methanol in dichloromethane to furnish the title compound as a pale brown solid (20 mg, yield 30%). $^1$H NMR (DMSO-d$_6$, 400 MHz) δ 8.25 (s, 1H), 7.65 (d, J=7.8 Hz, 2H), 7.45-7.40 (m, 7H), 7.18-7.08 (m, 5H), 4.85-4.80 (m, 1H), 4.72-4.68 (m, 3H), 4.57-4.54 (m, 1H), 4.34-4.29 (m, 1H), 3.45-3.41 (m, 2H); LCMS m/e: 528 [M+1]$^+$.

Example 41 trans 3-((4-Amino-3-(4-phenoxyphenyl)-1H-pyrazolo[3,4-d]pyrimidin-1-yl)methyl)-1,2-dithiolan-4-yl benzoate

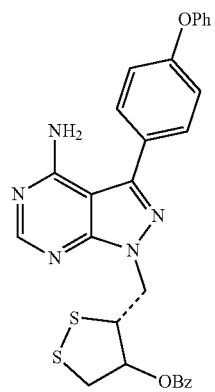

To a solution of 3-(4-phenoxyphenyl)-1H-pyrazolo[3,4-d]pyrimidin-4-amine (0.55 g, 1.8 mmol) in dry N,N dimethylformamide was added $Cs_2CO_3$ (0.9 g, 2.7 mmol) and was stirred for 10 minutes followed by the addition of trans 5-((methylsulfonyl)oxy)-1,2-dithian-4-yl benzoate (0.77 g, 2.3 mmol). The reaction mixture heated for 2 hours at 80° C. and then cooled and poured into water. The aqueous solution was extracted with ethyl acetate (3×200 mL) and the combined extracts were washed with water, dried over anhydrous $Na_2SO_4$, filtered and concentrated at reduced pressure. The pure product was obtained by column chromatography on silica gel (100-200 mesh) eluting with 1-2% (v/v) methanol in dichloromethane to furnish the title compound as pale brown solid (160 mg, yield 17%). $^1$H-NMR (DMSO-$d_6$, 400 MHz) δ 8.26 (s, 1H), 7.83 (d, J=7.2 Hz, 2H), 7.65-7.63 (m, 2H), 7.62 (d, J=8.8 Hz, 2H), 7.51-7.41 (m, 5H), 7.18-7.11 (m, 5H), 5.80 (m, 1H), 4.73 (d, J=7.2 Hz, 2H), 4.63-4.52 (m, 1H), 3.73 (dd, $J_1$=12.8 Hz, $J_2$=5.6 Hz, 1H), 3.47 (dd, $J_1$=12.8 Hz, $J_2$=2.8 Hz, 1H); LCMS m/e: 542 [M+1]$^+$.

Example 42 trans 3-((4-Amino-3-(4-phenoxyphenyl)-1H-pyrazolo[3,4-d]pyrimidin-1-yl)methyl)-1,2-dithiolan-4-ol

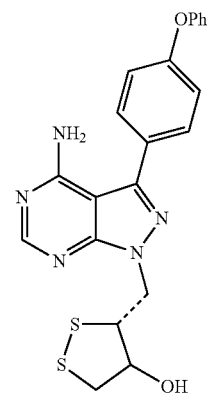

To a solution of trans 3-((4-amino-3-(4-phenoxyphenyl)-1H-pyrazolo[3,4-d]pyrimidin-1-yl)methyl)-1,2-dithiolan-4-yl benzoate (0.8 g, 1.478 mmol) in tetrahydrofuran (60 mL) was added 10% LiOH (30 mL) and was stirred for 4 hours at room temperature and then was poured into water, acidified with saturated citric acid and extracted with ethyl acetate (3×300 mL). The combined extracts were dried over anhydrous $Na_2SO_4$, filtered and concentrated at reduced pressure. The pure product was obtained by column chromatography on silica gel (100-200 mesh) eluting with 0.5% (v/v) methanol in dichloromethane to give the title compound as a pale brown solid (310 mg, yield 47%). %).
$^1$H-NMR (DMSO-$d_6$, 400 MHz) δ 8.26 (s, 1H), 7.67 (d, J=8.8 Hz, 2H), 7.45-7.42 (m, 2H), 7.19-7.12 (m, 5H), 5.33 (d, J=4.8 Hz, 1H), 4.62-4.47 (m, 3H), 4.01-4.00 (m, 1H), 3.73 (dd, J=12.8 Hz, $J_2$=5.6 Hz, 1H), 3.47 (dd, J=12.8 Hz, $J_2$=2.8 Hz, 1H); LCMS m/e: 438 [M+1]$^+$.

Example 43

(3S,4R)-3-((4-Amino-3-(4-phenoxyphenyl)-1H-pyrazolo[3,4-d]pyrimidin-1-yl)methyl)-1,2-dithiolan-4-ol and (3R,4S)-3-((4-amino-3-(4-phenoxyphenyl)-1H-pyrazolo[3,4-d]pyrimidin-1-yl)methyl)-1,2-dithiolan-4-ol The two enantiomers of trans 3-((4-amino-3-(4-phenoxyphenyl)-1H-pyrazolo[3,4-d]pyrimidin-1-yl)methyl)-1,2-dithiolan-4-ol were separated as peak 1, retention time 8.4 minutes (20 mg) and peak 2 retention time 10.4 minutes (19 mg) by the following chiral HPLC conditions:
Column: Chiralpak-IA (250*4.6*5.0 g); mobile phase-A:n-hexanes (0.1% trifluoroacetic acid); mobile phase-C: isopropanol:dichloromethane (90:10) isocratic: 50:50 (A:C); flow rate: 15.0 mL/min; column temp: ambient; diluent: mobile phase+dichloromethane; sample loading: 25 mg/injection; runtime: 20 minutes.
A. Peak 1 Data (3S,4R)-3-((4-Amino-3-(4-phenoxyphenyl)-1H-pyrazolo[3,4-d]pyrimidin-1-yl)methyl)-1,2-dithiolan-4-ol

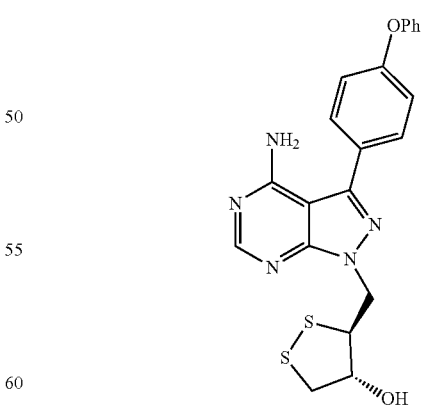

$^1$H NMR 400 MHz (DMSO-$d_6$, 400 MHz) δ 8.26 (s, 1H), 7.67 (d, J=8.4 Hz, 2H), 7.43 (t, J=8.0 Hz, 2H), 7.21-7.11 (m, 5H), 5.53 (d, J=4.8 Hz, 1H), 4.62-4.47 (m, 3H), 4.01-3.98 (m, 1H), 3.42 (dd, $J_1$=11.6 Hz, $J_2$=4.8 Hz, 1H), 3.07 (dd, $J_1$=12.0 Hz, $J_2$=4.0 Hz, 1H); MS (ES) m/e 438 [M+1]$^+$.

B. Peak 2 Data (3R,4S)-3-((4-Amino-3-(4-phenoxyphenyl)-1H-pyrazolo[3,4-d]pyrimidin-1-yl)methyl)-1,2-dithiolan-4-ol

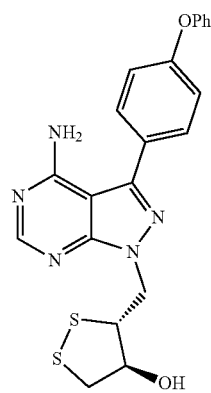 [SMILES: Nc1ncnc2c1c(-c1ccc(Oc3ccccc3)cc1)nn2C[C@H]1SSC[C@@H]1O]

$^1$H NMR 400 MHz (DMSO-d$_6$, 400 MHz) δ 8.26 (s, 1H), 7.67 (d, J=8.4 Hz, 2H), 7.43 (t, J=8.0 Hz, 2H), 7.21-7.11 (m, 5H), 5.53 (d, J=4.8 Hz, 1H), 4.62-4.47 (m, 3H), 4.01-3.98 (m, 1H), 3.42 (dd, J$_1$=11.6 Hz, J$_2$=4.8 Hz, 1H), 3.07 (dd, J$_1$=12.0 Hz, J$_2$=4.0 Hz, 1H); MS (ES) m/e 438 [M+1]$^+$.

Example 44 cis 3-((4-Amino-3-(4-phenoxyphenyl)-1H-pyrazolo[3,4-d]pyrimidin-1-yl)methyl)-1,2-dithiolan-4-yl benzoate

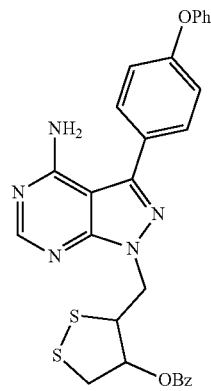

To a solution of 3-(4-phenoxyphenyl)-1H-pyrazolo[3,4-d]pyrimidin-4-amine (0.2 g, 0.66 mmol) in dry N,N dimethylformamide was added Cs$_2$CO$_3$ (0.32 g, 0.99 mmol). The solution was stirred for 10 minutes, followed by the addition of cis 5-((methylsulfonyl)oxy)-1,2-dithian-4-yl benzoate (1.1 g, 3.29 mmol) and was heated for 2 hours at 80° C. After cooling, it was poured into water and extracted with ethyl acetate (3×300 mL). The combined extracts were washed with water, dried over anhydrous Na$_2$SO$_4$, filtered and concentrated at reduced pressure. The pure product was obtained by column chromatography on silica gel (100-200 mesh) eluting with 1-2% (v/v) methanol in dichloromethane to furnish the title compound as a pale brown solid (70 mg, yield 20%) and proceeded next step. LCMS m/e: 542 [M+1]$^+$.

Example 45 cis 3-((4-Amino-3-(4-phenoxyphenyl)-1H-pyrazolo[3,4-d]pyrimidin-1-yl)methyl)-1,2-dithiolan-4-ol

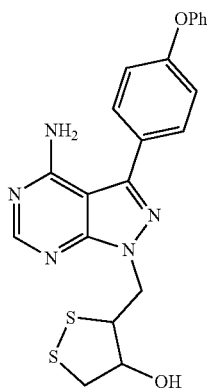 [SMILES: Nc1ncnc2c1c(-c1ccc(Oc3ccccc3)cc1)nn2CC1SSCC1O]

To a solution of cis 3-((4-amino-3-(4-phenoxyphenyl)-1H-pyrazolo[3,4-d]pyrimidin-1-yl)methyl)-1,2-dithiolan-4-yl benzoate (900 mg, 1.48 mmol) in tetrahydrofuran (80 mL) was added 10% aqueous LiOH (40 mL) at room temperature and was stirred for 4 hours. The reaction mixture was then poured into water, acidified with saturated citric acid and extracted with ethyl acetate (3×300 mL) and the combined extracts were dried over anhydrous Na$_2$SO$_4$, filtered and concentrated at reduced pressure. The pure product was obtained by column chromatography on silica gel (100-200 mesh) eluting with 0.5% (v/v) methanol in dichloromethane to give the title compound as a pale brown solid (360 mg, yield 50%). $^1$H-NMR (DMSO-d$_6$, 400 MHz): δ 8.26 (s, 1H), 7.91 (d, J=7.6 Hz, 2H), 7.42 (d, J=7.6 Hz, 2H), 7.19-7.11 (m, 5H), 5.66 (bs, 1H), 4.81-4.76 (m, 2H), 4.68-4.62 (m, 1H), 4.12-4.08 (m, 1H), 3.40 (dd, J=11.6 Hz, J$_2$=4.8 Hz, 1H), 3.10 (dd, J$_1$=11.6 Hz, J$_2$=3.2 Hz, 1H); LCMS m/e: 438 [M+1]$^+$.

Example 46

(3S,4S)-3-((4-Amino-3-(4-phenoxyphenyl)-1H-pyrazolo[3,4-d]pyrimidin-1-yl)methyl)-1,2-dithiolan-4-ol and (3R,4R)-3-((4-amino-3-(4-phenoxyphenyl)-1H-pyrazolo[3,4-d]pyrimidin-1-yl)methyl)-1,2-dithiolan-4-ol The two enantiomers of cis 3-((4-amino-3-(4-phenoxyphenyl)-1H-pyrazolo[3,4-d]pyrimidin-1-yl)methyl)-1,2-dithiolan-4-ol were separated as peak 1 retention time 6.5 minutes (20 mg) and peak 2 retention time 9.1 minutes (26 mg) by the following chiral HPLC conditions: Column: Chiralpak-IA (250*4.6*5.0 g); mobile phase-A: n-hexanes; mobile phase-B: 0.3% trifluoroacetic acid in ethanol:dichloromethane (85:15); isocratic: 40:60(A:B); flow rate: 15.0 mL/min; column temp: ambient; diluent: mobile phase; sample loading: 25 mg/inj; run time: 25 minutes.

A. Peak 1 Data (3S,4S)-3-((4-Amino-3-(4-phenoxyphenyl)-1H-pyra-zolo[3,4-d]pyrimidin-1-yl)methyl)-1,2-dithiolan-4-ol

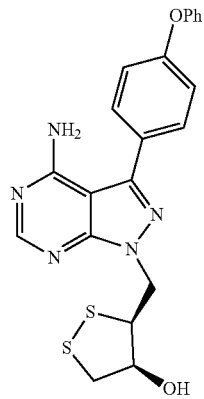 [SMILES: Nc1ncnc2c1c(-c1ccc(Oc3ccccc3)cc1)nn2C[C@@H]1SSC[C@@H]1O]

¹H NMR 400 MHz (DMSO-d₆): δ 8.26 (s, 1H), 7.67 (d, J=8.4 Hz, 2H), 7.45-7.413 (m, 2H), 7.19-7.11 (m, 5H), 5.53 (d, J=4.8 Hz, 1H), 4.62-4.47 (m, 3H), 4.01-3.96 (m, 1H), 3.44 (dd, J, =11.6 Hz, J₂=4.8 Hz, 1H), 3.07 (dd, J, =12.0 Hz, J₂=4.0 Hz, 1H); MS (ES) m/e 438 [M+1]⁺.

B. Peak 2 Data (3R,4R)-3-((4-Amino-3-(4-phenoxyl)enyl)-1H-pyra-zolo[3,4-d]pyrimidin-1-yl)methyl)-1,2-dithiolan-4-ol

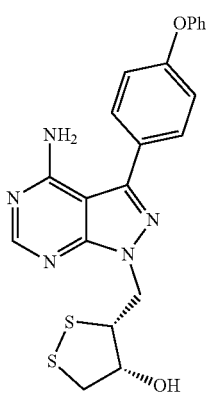

¹H NMR (DMSO-d₆, 400 MHz): δ 8.26 (s, 1H), 7.67 (d, J=8.4 Hz, 2H), 7.45-7.41 (m, 2H), 7.19-7.11 (m, 5H), 5.53 (d, J=4.8 Hz, 1H), 4.62-4.47 (m, 3H), 4.01-3.96 (m, 1H), 3.44 (dd, J₁=11.6 Hz, J₂=4.8 Hz, 1H), 3.07 (dd, J₁=12.0 Hz, J₂=4.0 Hz, 1H); MS (ES) m/e 438 [M+1]⁺.

Example 47 trans 1-((4-((tert-Butyldimethylsilyl)oxy)-1,2-dithi-olan-3-yl)methyl)-3-(4-phenoxyphenyl)-1H-pyrazolo[3,4-d]pyrimidin-4-amine

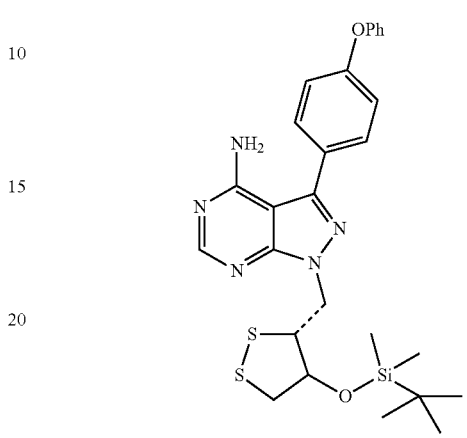

To a slurry of trans-4-tert-butyldimethylsilyloxy-5-hy-droxy-1,2-dithiane (200 mg, 0.75 mmol), of 3-(4-phenoxy-phenyl)-1H-pyrazolo[3,4-d]pyrimidin-4-amine (342 mg, 1.13 mmol), and triphenylphosphine (296 mg, 1.13 mmol) in N,N dimethylformamide (1 mL) at 0° C. under argon atmosphere was added diethyl azodicarboxylate (0.18 mL, 1.13 mmol) dropwise and the mixture was stirred at room temperature for 16 hours. The reaction mixture was then quenched with one drop of acetic acid and methanol, diluted and filtered through celite pad. The filtrate was concentrated in vacuo to give a residue which was diluted with methanol and adsorbed into silica gel (5 g) and then purified by flash chromatography using ethyl acetate/hexanes (3/7) as an eluent. to give the desired product (174 mg, 43%) as a colorless oil: ¹H NMR (DMSO-d₆, 400 MHz): δ 8.27 (s, 1H), 7.51 (d, J=8.4 Hz, 2H), 7.41 (m, 2H), 7.25-7.08 (m, 5H), 5.53 (d, J=4.8 Hz, 1H), 4.62-4.47 (m, 3H), 4.01-3.96 (m, 1H), 3.07 (dd, J₁=11.6 Hz, J₂=4.8 Hz, 1H), 2.82 (dd, J₁=11.0 Hz, J₂=4.0 Hz, 1H), 2.62 (m, 1H), 0.98 (s, 9H), 0.21 (s, 6H).

Example 48 trans-1-((4-((tert-Butyldimethylsilyl)oxy)-1,2-dithi-olan-3-yl)methyl)-3-(4-phenoxyphenyl)-1H-pyrazolo[3,4-d]pyrimidin-4-amine To a solution of 3-(4-phenoxyphenyl)-1H-pyrazolo[3,4-d]pyrimidin-4-amine (0.46 g, 1.5 mmol) in dry N,N dim-ethylformamide was added Cs₂CO₃ (0.7 g, 2.1 mmol) and was stirred for 10 minutes followed by the addition of trans-5-tert-butyldimethylsilyloxy-1,2-dithian-4-yl meth-anesulfonate (0.70 g, 2.1 mmol). The reaction mixture heated for 2 hours at 80° C. and then cooled and poured into water. The aqueous solution was extracted with ethyl acetate (3×200 mL) and the combined extracts were washed with water, dried over anhydrous Na₂SO₄, filtered and concen-trated at reduced pressure. The pure product was obtained by column chromatography on silica gel (100-200 mesh) elut-ing with ethyl acetate/hexanes (3/7) methanol in dichlo-romethane to furnish the title compound as pale brown solid (120 mg, yield 17%). $^1$H NMR (DMSO-$d_6$, 400 MHz): δ 8.27 (s, 1H), 7.51 (d, J=8.4 Hz, 2H), 7.41 (m, 2H), 7.25-7.08 (m, 5 H), 5.53 (d, J=4.8 Hz, 1H), 4.62-4.47 (m, 3H), 4.01-3.96 (m, 1H), 3.07 (dd, J=11.6 Hz, $J_2$=4.8 Hz, 1H), 2.82 (dd, J=11.0 Hz, $J_2$=4.0 Hz, 1H), 2.62 (m, 1H), 0.98 (s, 9H), 0.21 (s, 6H).

Example 49 trans 3-((4-Amino-3-(4-phenoxyphenyl)-1H-pyrazolo[3,4-d]pyrimidin-1-yl)methyl)-1,2-dithiolan-4-ol

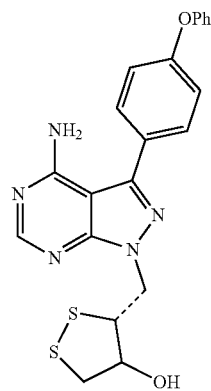

A solution of trans 1-((4-((tert-butyldimethylsilyl)oxy)-1,2-dithiolan-3-yl)methyl)-3-(4-phenoxyphenyl)-1-1H-pyrazolo[3,4-d]pyrimidin-4-amine (70 mg, 0.17 mmol), glacial acetic acid (17 uL, 0.3 mmol), tetra-n-butylammonium fluoride in tetrahydrofuran (1.0 M, 0.19 mL, 0.19 mmol) and tetrahydrofuran (2.0 mL) was stirred under argon atmosphere for 1.5 hours. The reaction mixture was quenched with 1 drop of acetic acid, dissolved in methanol and concentrated to produce a crude mixture which was dissolved in methanol, adsorbed on silica gel and purified by flash chromatography (eluent ethyl acetate). Concentration of the fractions gave the product as a light yellow powder (29.5 mg, 59%). $^1$H NMR 400 MHz (DMSO-$d_6$, 400 MHz) δ 8.26 (s, 1H), 7.67 (d, J=8.4 Hz, 2H), 7.43 (t, J=8.0 Hz, 2H), 7.21-7.11 (m, 5H), 5.53 (d, J=4.8 Hz, 1H), 4.62-4.47 (m, 3H), 4.01-3.98 (m, 1H), 3.42 (dd, $J_1$=11.6 Hz, $J_2$=4.8 Hz, 1H), 3.07 (dd, $J_1$=12.0 Hz, $J_2$=4.0 Hz, 1H); MS (ES) m/e 438 [M+1]$^+$.

Example 50

3-(Phenylethynyl)-1H-pyrazolo[3,4-d]pyrimidin-4-amine

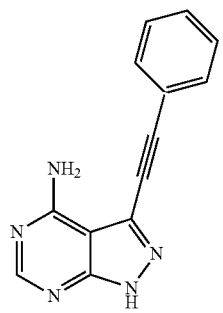

To a solution of 3-iodo-1H-pyrazolo[3,4-d]pyrimidin-4-amine (2.0 g, 7.7 mmol) was added sequentially, phenyl acetylene (3.1 g, 30.7 mmol), copper (I) iodide (0.3 g, 1.5 mmol) and triethylamine (2.3 g, 23.0 mmol) in N,N dimethylformamide (20 mL). The reaction mixture was purged with nitrogen atmosphere and 1,1' (bisdiphenylphosphino)ferrocenepalladium(II) dichloride (Pd(dppf)Cl$_2$ (0.6 g, 0.77 mmol) was slowly added at room temperature followed by heating at 80° C. for 6 hours. The reaction mixture was cooled, filtered through celite and then poured into ice water and was extracted with ethyl acetate. The combined organic layer extracts were dried over anhydrous Na$_2$SO$_4$ and concentrated in vacuo to give a crude oil which was purified by column chromatography on silica gel (100-200 mesh), eluting with 50% ethyl acetate:hexanes mixture to afford the title compound (0.31 g, 17%) as a light brown solid. $^1$H NMR (DMSO-$d_6$, 400 MHz): δ 13.83 (s, 1H), 8.22 (s, 1H), 7.72 (dd, J=7.6 Hz, $J_2$=4.0 Hz, 2H), 7.46 (dd, $J_1$=5.2 Hz, $J_2$=4.0 Hz, 3H); LCMS (retention time 5.0 minutes, m/e 236 [M+1]$^+$, 95.9%), Capcell pack C18 150*4.6, 3 column at 254 nm.

Example 51 trans 3-((4-Amino-3-(phenylethynyl)-1H-pyrazolo[3,4-d]pyrimidin-1-yl)methyl-1,2-dithiolan-4-yl benzoate

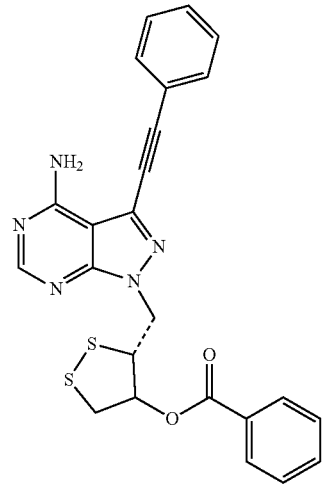

To a solution of 3-(phenylethynyl)-1-1H-pyrazolo[3,4-d]pyrimidin-4-amine (0.5 g, 2.1 mmol) in dry N,N dimethylformamide (15 mL) was added Cs$_2$CO$_3$ (1.0 g, 3.2 mmol) and was stirred for 10 minutes followed by the addition of trans 5-((methylsulfonyl)oxy)-1,2-dithian-4-yl benzoate (1.4 g, 4.2 mmol). The reaction mixture heated for 3 hours at 80° C. and then cooled and poured into water. The aqueous solution was extracted with ethyl acetate (3×200 mL) and the combined extracts were washed with water, dried over anhydrous Na$_2$SO$_4$, filtered and concentrated at reduced pressure. The pure product was obtained by column chromatography on silica gel (100-200 mesh) eluting with 40% ethyl acetate:hexanes to furnish the title compound as pale brown solid (200 mg, yield 17%). $^1$H-NMR (DMSO-$d_6$, 400 MHz) δ 8.27 (s, 1H), 7.90 (d, J=7.6 Hz, 2H), 7.73-7.64 (m, 4H), 7.53-7.47 (m, 6H), 5.76 (d, J=2 Hz, 1H), 4.71 (d, J=7.6 Hz, 2H), 4.35 (dd, $J_1$=7.0 Hz, $J_2$=5.4 Hz, 1H), 3.74

(dd, $J_1$=10.0 Hz, $J_2$=7.6 Hz, 1H), 3.47 (dd, $J_1$=12.8 Hz, $J_2$=3.0 Hz, 1H); HPLC (retention time 9.6 minutes, 91.7%), Capcell pack C18 150*4.6, 3 column at 254 nm.

Example 52 trans 3-(4-Amino-3-(phenylethynyl)-1H-pyrazolo[3,4-d]pyrimidin-1-yl)methyl-1,2-dithiolan-4-ol

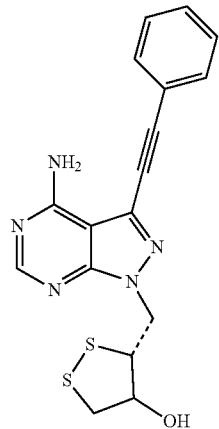

To a solution of trans 3-((4-amino-3-(phenylethynyl)-1-1H-pyrazolo[3,4-d]pyrimidin-1-yl)methyl-1,2-dithiolan-4-yl-benzoate (100 mg, 0.21 mmol) in tetrahydrofuran (10 mL) and methanol (1 mL) was added LiOH (17 mg, 0.42 mmol) and the reaction mixture was stirred for 3 hours at room temperature. The reaction mixture was quenched with ice water, acidified with citric acid and extracted with ethyl acetate. The extracts were combined, dried over anhydrous $Na_2SO_4$, filtered and evaporated in vacuo to afford the title compound as a pale yellow solid (40 mg, 51%). $^1$H NMR (DMSO-$d_6$, 400 MHz) δ 8.37 (s, 1H), 8.08 (d, J=6.0 Hz, 1H), 7.61-7.55 (m, 2H), 7.47-7.40 (m, 3H), 6.12 (bs, 1H), 4.62 (m, 1H), 4.51 (dd, J, =14.5 Hz, $J_2$=8.8 Hz, 1H), 4.09 (m, 1H), 3.25 (m, 1H), 3.09 (d, J=6.9 Hz, 1H); LCMS (retention time 6.8 minutes, 91.7%), Capcell pack C18 150*4.6, 3μ column at 254 nm.

Example 53 trans 3-((4-Amino-3-(phenylethynyl)-1H-pyrazolo[3,4-d]pyrimidin-1-yl)methyl-1-oxido-1,2-dithiolan-4-yl benzoate

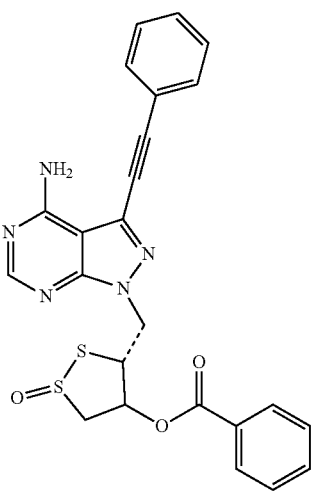

To a solution of trans 3-((4-amino-3-(phenylethynyl)-1-1H-pyrazolo[3,4-d]pyrimidin-1-yl)methyl-1,2-dithiolan-4-yl-benzoate (100 mg, 0.21 mmol) in glacial acetic acid (5 mL) was added 30% hydrogen peroxide (7 mg, 2.2 mmol) in glacial acetic acid (2 mL) at 0° C. and then stirred at room temperature for 16 hours. The reaction mixture was then carefully concentrated to dryness and the solvents were removed by co-distilling with toluene to afford the title compound as a light brown solid (50 mg, 49%). LCMS (retention time 7.6 minutes, 55.2%), Capcell pack C18 150*4.6, 3μ column at 254 nm.

Example 54

6-(4-Amino-1H-pyrazolo[3,4-d]pyrimidin-3-yl)benzo[d]oxazol-2-amine

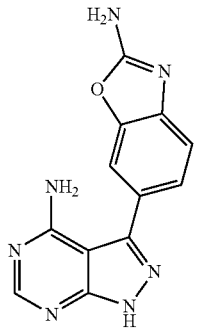 [SMILES: Nc1nc2ccc(-c3n[nH]c4ncnc(N)c34)cc2o1]

To a solution of 3-iodo-1H-pyrazolo[3,4-d]pyrimidin-4-amine (2.0 g, 7.7 mmol) and benzo[d]oxazol-2-amine (3.0 g, 11.5 mmol) in N,N dimethylformamide (20 mL) was added a solution of NaOH (0.61 g, 15.3 mmol) in water (10 mL). The reaction mixture was purged with nitrogen atmosphere and 1,1' (bisdiphenylphosphino)ferrocenepalladium(II) dichloride (Pd(dppf)Cl$_2$ (0.56 g, 0.76 mmol) was slowly added at room temperature followed by heating at 120° C. for 16 hours. The reaction mixture was cooled, poured into ice water and was extracted with ethyl acetate. The combined organic layer extracts were dried over anhydrous $Na_2SO_4$, filtered, and concentrated in vacuo to give a crude oil which was purified by column chromatography on silica gel (100-200 mesh), eluting with 80% ethyl acetate:hexanes mixture to afford the title compound (0.32 g, 16%) as a light brown solid. $^1$H NMR (DMSO-$d_6$, 400 MHz): δ 13.56 (s, 1H), 8.21 (s, 1H), 7.56 (d, J=16.8 Hz, 2H), 7.43 (dd, $J_1$=21.0 Hz, $J_2$=1.2 Hz, 2H), 7.23 (dd, $J_1$=6.4 Hz, $J_2$=1.6 Hz, 1H) LCMS (retention time 3.6 minutes, m/e 268 [M+1]$^+$, 97.5%), Capcell pack C18 150*4.6, 3 column at 254 nm.

Example 55 trans 3-((4-Amino-3-(2-aminobenzo[d]oxazol-5-yl)-1H-pyrazolo[3,4-d]pyrimidin-1-yl)methyl)-1,2-dithiolan-4-yl benzoate

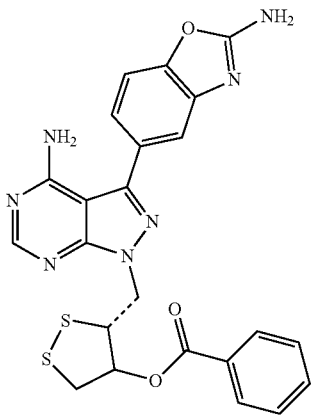

To a solution of 6-(4-amino-1H-pyrazolo[3,4-d]pyrimidin-3-yl)benzo[d]oxazol-2-amine (200 mg, 0.74 mmol) in dry N,N dimethylformamide (10 mL) was added $Cs_2CO_3$ (360 mg, 1.1 mmol) and was stirred for 10 minutes followed by the addition of trans 5-((methylsulfonyl)oxy)-1,2-dithian-4-yl benzoate (480 mg, 1.5 mmol). The reaction mixture heated for 3 hours at 80° C. and then cooled and poured into water. The aqueous solution was extracted with ethyl acetate (3×200 mL) and the combined extracts were washed with water, dried over anhydrous $Na_2SO_4$, filtered and concentrated at reduced pressure. The pure product was obtained by column chromatography on silica gel (100-200 mesh) eluting with 2% methanol in dichloromethane to furnish the title compound as pale brown solid (50 mg, yield 13%). $^1$H-NMR (DMSO-$d_6$, 400 MHz) δ 8.26 (s, 1H), 7.95 (m, 1H), 7.86 (d, J=6.0 Hz, 2H), 7.65 (t, J=4.0 Hz, 2H), 7.53-7.47 (m, 3H), 7.35 (d, J=1.2 Hz, 1H), 7.17 (dd, $J_1$=6.4 Hz, $J_2$=1.2 Hz, 1H), 5.83 (m, 1H), 4.74 (dd, J, =11.2 Hz, $J_2$=6.0 Hz, 1H), 4.72 (dd, $J_1$=11.6 Hz, $J_2$=4.4 Hz, 1H), 4.49 (dt, $J_1$=4.0 Hz, $J_2$=2.0 Hz, 1H), 3.74 (dd, $J_1$=10.0 Hz, $J_2$=4.0 Hz, 2H), 3.47 (dd, $J_1$=6.8 Hz, $J_2$=4.0 Hz, 2H); HPLC (retention time 6.2 minutes, [M+1]$^+$, 82.0%), Capcell pack C18 150*4.6, 3 column at 254 nm.

Example 56 trans 3-((4-Amino-3-(2-aminobenzo[d]oxazol-5-yl)-1H-pyrazolo[3,4-d]pyrimidin-1-yl)methyl)-1,2-dithiolan-4-ol

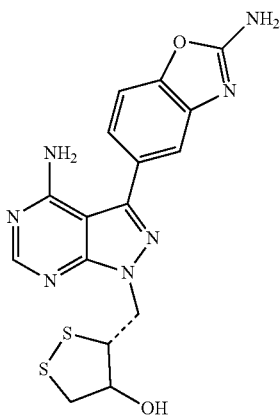

To a solution of trans 3-((4-amino-3-(2-aminobenzo[d]oxazol-5-yl)-1H-pyrazolo[3,4-d]pyrimidin-1-yl)methyl)-1,2-dithiolan-4-yl benzoate (100 mg, 0.19 mmol) in tetrahydrofuran (60 mL) and methanol (1 mL) was added LiOH (16 mg, 0.39 mmol) and the reaction mixture was stirred for 3 hours at room temperature. The reaction mixture was quenched with ice water, acidified with citric acid and extracted with ethyl acetate. The extracts were combined, dried over anhydrous $Na_2SO_4$, filtered and evaporated in vacuo to afford the title compound as a pale yellow solid (60 mg, 34%). $R_f$=0.3, 10% methanol in dichloromethane); LCMS (retention time 3.7 minutes, 34.7%), Capcell pack C18 150*4.6, 3μ column at 254 nm.

Example 57 trans 3-((4-Amino-3-(2-aminobenzo[d]oxazol-5-yl)-1H-pyrazolo[3,4-d]pyrimidin-1-yl)methyl)-1-oxido-1,2-dithiolan-4-yl benzoate

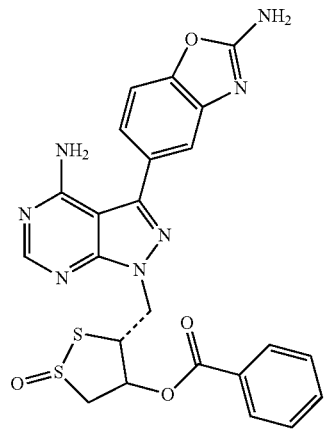

To a solution of trans 3-((4-amino-3-(2-aminobenzo[d]oxazol-5-yl)-1H-pyrazolo[3,4-d]pyrimidin-1-yl)methyl)-1,2-dithiolan-4-ol (100 mg, 0.24 mmol) in glacial acetic acid (5 mL) was added 30% hydrogen peroxide (9 mg, 2.7 mmol) in glacial acetic acid (2 mL) at 0° C. and then stirred at room temperature for 16 hours. The reaction mixture was then carefully concentrated to dryness and the solvents were removed by co-distilling with toluene to afford the title compound as a light brown solid (50 mg, 49%). LCMS (2 diastereomers: retention time 7.3 minutes, 35.0%, retention time 7.5 minutes, 28.0%), Capcell pack C18 150*4.6, 3μ column at 254 nm.

Example 58 trans 3-((4-Amino-3-(2-aminobenzo[d]oxazol-5-yl)-1H-pyrazolo[3,4-d]pyrimidin-1-yl)methyl)-4-hydroxy-1,2-dithiolane 1-oxide

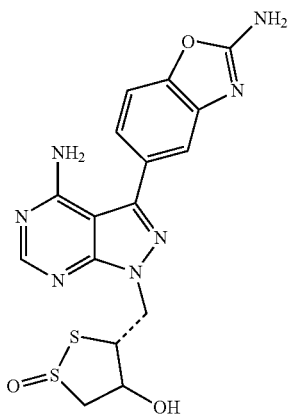

To a solution of trans 3-((4-amino-3-(2-aminobenzo[d]oxazol-5-yl)-1H-pyrazolo[3,4-d]pyrimidin-1-yl)methyl)-1,2-dithiolan-4-yl benzoate (100 mg, 0.24 mmol) in glacial acetic acid (5 mL) was added 30% hydrogen peroxide (9 mg, 2.7 mmol) in glacial acetic acid (2 mL) at 0° C. and then stirred at room temperature for 16 hours. The reaction mixture was then carefully concentrated to dryness and the solvents were removed by co-distilling with toluene to afford the title compound as a light brown solid (50 mg, 49%). LCMS (2 diastereomers: retention time 4.3 minutes, 12.0%, retention time 5.2 minutes, 64.0%), Capcell pack C18 150*4.6, 3µ column at 254 nm.

Example 59

1-(4-Bromophenoxy)-2-fluorobenzene

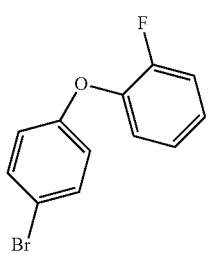 [SMILES: Fc1ccccc1Oc1ccc(Br)cc1]

To a solution containing 2-fluorophenol (10 g, 89.2 mmol), copper (I) bromide (1.3 g, 107.0 mmol) and potassium tert butoxide (11.0 g, 98.1 mmol) in dry N,N dimethylformamide (80 mL) was heated for 4 hours at 150° C. and then cooled to room temperature. The reaction mixture was filtered through celite and the filtrate was dissolved in ethyl acetate and washed with brine and water. The combined organic extracts were dried over anhydrous $Na_2SO_4$, filtered and evaporated in vacuo to afford a crude compound which was purified by flash chromatography on silica gel (100-200 mesh) eluting with 40% ethyl acetate in hexanes to afford the title compound as an off white solid (2.6 g, 11%). $^1$H-NMR (CDCl$_3$, 400 MHz) δ 7.41 (d, J=9.0 Hz, 2H), 7.18 (m, 1H), 7.12 (m, 2H), 7.07 (m, 1H), 6.85 (d, J=9.0 Hz, 2H).

Example 60

(4-(2-Fluorophenoxy)phenyl)boronic acid

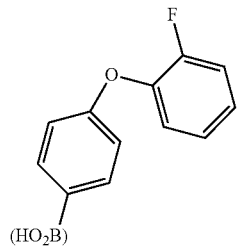

To a solution of 1-(4-bromophenoxy)-2-fluorobenzene (10 g, 37.4 mmol), in tetrahydrofuran (150 mL) at −78° C. was added n-butyllithium (2.5 M, 22.4 mL, 56.2 mmol) and the reaction mixture was stirred at that temperature for 1 hour. Triisopropyl borate (10.3 g, 44.9 mmol) was then added and the reaction was allowed to warm up to room temperature with stirring for 6 hours. The reaction mixture was then quenched with a saturated solution of ammonium chloride and concentrated under reduced pressure. The resultant residue was diluted with an aqueous solution of 30% KOH and neutralized to pH 2-3 with dilute HCl. The resulting solution was extracted with ethyl acetate and the combined extracts were dried over anhydrous $Na_2SO_4$, filtered and evaporated in vacuo to afford a crude compound which was purified by flash chromatography on silica gel (100-200 mesh) eluting with 40% ethyl acetate in hexanes to afford the title compound as an off white solid (2.6 g, 11%). $^1$H-NMR (CDCl$_3$, 400 MHz) δ 8.16 (d, J=8.6 Hz, 2H), 7.20 (m, 4H), 7.06 (d, J=8.6 Hz, 2H).

Example 61

3-(4-(2-Fluorophenoxy)phenyl-1H-pyrazolo[3,4-d]pyrimidin-4-amine

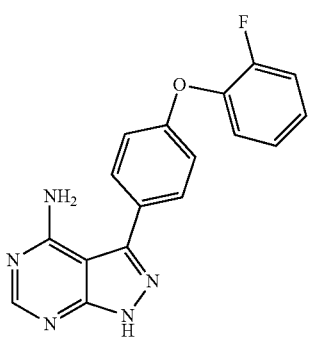 [SMILES: Nc1ncnc2[nH]nc(-c3ccc(Oc4ccccc4F)cc3)c12]

To a solution containing 3-iodo-1H-pyrazolo[3,4-d]pyrimidin-4-amine (3.0 g, 11.5 mmol) and (4-(2-fluorophenoxy)phenyl)boronic acid in N,N dimethylformamide (20 mL) was added NaOH (900 mg, 22.9 mmol). The reaction mixture was purged with nitrogen atmosphere and 1,1' (bisdiphenylphosphino)ferrocenepalladium(II) dichloride (Pd(dppf)Cl$_2$ (840 mg, 1.1 mmol) was slowly added at room temperature followed by heating at 120° C. for 16 hours. The reaction mixture was cooled, filtered through celite and then poured into ice water and was extracted with ethyl acetate. The combined organic layer extracts were dried over anhydrous Na$_2$SO$_4$ and concentrated in vacuo to give a crude oil which was purified by column chromatography on silica gel (100-200 mesh), eluting with 50% ethyl acetate:hexanes mixture to afford the title compound (500 mg, 13.5%) as a light brown solid. $^1$H NMR (DMSO-d$_6$, 400 MHz): δ 13.55 (s, 1H), 8.21 (s, 1H), 7.71 (m, 2H), 7.66 (d, J=8.6 Hz, 2H), 7.44 (m, 1H), 7.29 (m, 3H), 7.12 (m, J=8.4 Hz, 2H).

Example 62 trans 3-((4-Amino-3-(4-(2-fluorophenoxyphenyl)-1H-pyrazolo[3,4-d]pyrimidin-1-yl)methyl)-1,2-dithiolan-4-yl benzoate

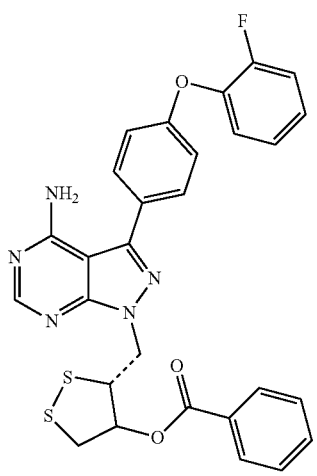

To a solution of 3-(4-(2-fluorophenoxy)phenyl-1H-pyrazolo[3,4-d]pyrimidin-4-amine (500 mg, 1.6 mmol) in dry N,N dimethylformamide (15 mL) was added Cs$_2$CO$_3$ (750 mg, 2.3 mmol) and was stirred for 10 minutes followed by the addition of trans 5-((methylsulfonyl)oxy)-1,2-dithian-4-yl benzoate (1.03 g, 3.1 mmol). The reaction mixture heated for 3 hours at 80° C. and then cooled and poured into water. The aqueous solution was extracted with ethyl acetate (3×200 mL) and the combined extracts were washed with water, dried over anhydrous Na$_2$SO$_4$, filtered and concentrated at reduced pressure. The pure product was obtained by column chromatography on silica gel (100-200 mesh) eluting with 50% ethyl acetate in hexanes to furnish the title compound as pale brown solid (300 mg, yield 35%). $^1$H-NMR (DMSO-d$_6$, 400 MHz) δ 8.26 (s, 1H), 7.95 (m, 1H), 7.86 (d, J=6.0 Hz, 2H), 7.65 (t, J=4.0 Hz, 2H), 7.53-7.47 (m, 3H), 7.35 (d, J=1.2 Hz, 1H), 7.17 (dd, J$_1$=6.4 Hz, J$_2$=1.2 Hz, 1H), 5.83 (m, 1H), 4.74 (dd, J$_1$=11.2 Hz, J$_2$=6.0 Hz, 1H), 4.72 (dd, J$_1$=11.6 Hz, J$_2$=4.4 Hz, 1H), 4.49 (dt, J$_1$=4.0 Hz, J$_2$=2.0 Hz, 1H), 3.74 (dd, J$_1$=10.0 Hz, J$_2$=4.0 Hz, 2H), 3.47 (dd, J$_1$=6.8 Hz, J$_2$=4.0 Hz, 2H); HPLC (retention time 10.0 minutes, [M+1]$^+$, 85.0%), Capcell pack C18 150*4.6, 3μ column at 254 nm.

Example 63 trans 3-((4-Amino-3-(4-(2-fluorophenoxyphenyl)-1H-pyrazolo[3,4-d]pyrimidin-1-yl)methyl)-1,2-dithiolan-4-ol

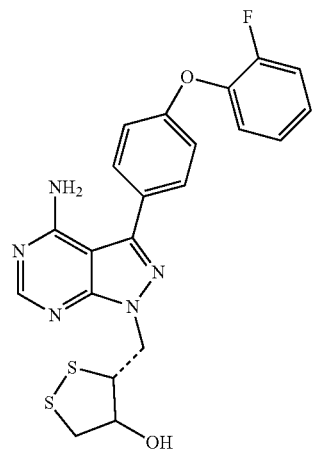

To a solution of trans 3-((4-amino-3-(4-(2-fluorophenoxyphenyl)-1H-pyrazolo[3,4-d]pyrimidin-1-yl)methyl)-1,2-dithiolan-4-yl benzoate (200 mg, 0.35 mmol) in tetrahydrofuran (10 mL) and methanol (1 mL) was added LiOH (20 mg, 0.71 mmol) and the reaction mixture was stirred for 3 hours at room temperature. The reaction mixture was quenched with ice water, acidified with citric acid and extracted with ethyl acetate. The extracts were combined, dried over anhydrous Na$_2$SO$_4$, filtered and evaporated in vacuo to afford the title compound as a pale yellow solid (90 mg, 57%). $^1$H NMR (CDCl3,400 MHz) δ 8.35 (s, 1H), 8.09 (d, J=7.1 Hz, 1H), 7.63 (d, J=8.6 Hz, 1H), 7.60 (d, J=8.6 Hz, 1H), 7.47 (m, 1H), 7.21 (m, 4H), 7.14 (d, J=8.6 Hz, 2H), 4.68 (m, 1H), 4.62 (m, 1H), 4.54 (dd, J$_1$=14.5 Hz, J$_2$=9.0 Hz, 2H), 4.09 (m, 1H), 3.51 (m, 1H), 3.25 (dd, J$_1$=11.6 Hz, J$_2$=2.3 Hz, 1H); MS: m/e 456[M+1]$^+$; LCMS (retention time 6.0 minutes, 77.4%), Capcell pack C18 150*4.6, 3μ column at 254 nm.

Example 64

4-Bromo-2-fluoro-1-phenoxybenzene

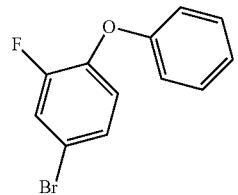 [SMILES: Fc1cc(Br)ccc1Oc1ccccc1]

To a solution containing 4-bromo-2-fluorophenol (10.0 g, 52.7 mmol), phenyl boronic acid (19.3 g, 157.9 mmol), copper (II) acetate (1.2 g, 5.8 mmol) and triethylamine (36.7 mL, 263.3 mmol) in dichloromethane (200 mL) was stirred at room temperature for 16 hours. The reaction mixture was filtered through celite and the filtrate was washed with brine and water. The combined organic extracts were dried over anhydrous Na$_2$SO$_4$, filtered and evaporated in vacuo to afford a crude compound which was purified by flash chromatography on silica gel (100-200 mesh) eluting with 5% ethyl acetate in hexanes to afford the title compound as an off white solid (4.1 g, 11%). $^1$H NMR (CDCl$_3$, 400 MHz) δ 7.35 (m, 2H), 7.24 (d, J=1.6 Hz, 1H), 7.21 (m, 1H), 7.11 (t, J=7.6 Hz, 1H), 6.96 (m, 3H).

Example 65

(3-Fluoro-4-phenoxyphenyl)boronic acid

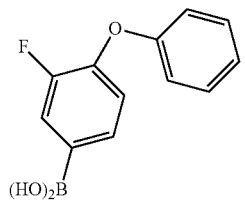 [SMILES: OB(O)c1ccc(Oc2ccccc2)c(F)c1]

To a solution of 4-bromo-2-fluoro-1-phenoxybenzene (10 g, 37.4 mmol), in tetrahydrofuran (150 mL) at −78° C. was added n-butyllithium (2.5 M, 22.4 mL, 56.2 mmol) and the reaction mixture was stirred at that temperature for 1 hour. Triisopropyl borate (10.3 g, 44.9 mmol) was then added and the reaction was allowed to warm up to room temperature with stirring for 6 hours. The reaction mixture was then quenched with a saturated solution of ammonium chloride and concentrated under reduced pressure. The resultant residue was diluted with an aqueous solution of 30% KOH and neutralized to pH 2-3 with dilute HCl. The resulting solution was extracted with ethyl acetate and the combined extracts were dried over anhydrous Na$_2$SO$_4$, filtered and evaporated in vacuo to afford a crude compound which was purified by flash chromatography on silica gel (100-200 mesh) eluting with 30% ethyl acetate in hexanes to afford the title compound as an off white solid (3.9 g, 45%). $^1$H-NMR (CDCl$_3$, 400 MHz) δ 8.16 (d, J=8.6 Hz, 2H), 7.20 (m, 4H), 7.06 (d, J=8.6 Hz, 2H); LCMS (retention time 6.9 minutes, 82.5%), Capcell pack C18 150*4.6, 3 column at 254 nm.

Example 66

3-(3-Fluoro-4-phenoxyphenyl-1H-pyrazolo[3,4-d]pyrimidin-4-amine

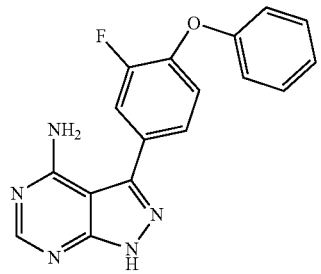 [SMILES: Nc1ncnc2[nH]nc(-c3ccc(Oc4ccccc4)c(F)c3)c12]

To a solution containing 3-iodo-1H-pyrazolo[3,4-d]pyrimidin-4-amine (2.0 g, 7.7 mmol) and (3-fluoro-4-phenoxyphenyl)boronic acid in N,N dimethylformamide (15 mL) was added NaOH (610 mg, 15.3 mmol). The reaction mixture was purged with nitrogen atmosphere and 1,1' (bisdiphenylphosphino)ferrocenepalladium(II) dichloride (Pd(dppf)Cl$_2$ (560 mg, 0.77 mmol) was slowly added at room temperature followed by heating at 120° C. for 16 hours. The reaction mixture was cooled, filtered through celite and then poured into ice water and was extracted with ethyl acetate. The combined organic layer extracts were dried over anhydrous Na$_2$SO$_4$ and concentrated in vacuo to give a crude oil which was purified by column chromatography on silica gel (100-200 mesh), eluting with 50% ethyl acetate:hexanes mixture to afford the title compound (450 mg, 18.2%) as a light yellow solid. LCMS (retention time 7.3 minutes, 91.5%), Capcell pack C18 150*4.6, 3 column at 254 nm.

Example 67 trans 3-((4-Amino-3-(3-fluoro-4-phenoxyphenyl)-1H-pyrazolo[3,4-d]pyrimidin-1-yl)methyl)-1,2-dithiolan-4-yl benzoate

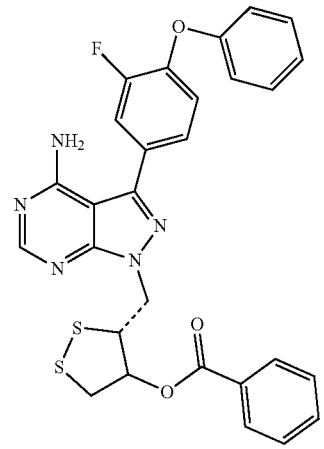

To a solution of 3-(3-fluoro-4-phenoxyphenyl-1H-pyrazolo[3,4-d]pyrimidin-4-amine (500 mg, 1.6 mmol) in dry N,N dimethylformamide (10 mL) was added Cs$_2$CO$_3$ (750 mg, 2.3 mmol) and was stirred for 10 minutes followed by the addition of trans 5-((methylsulfonyl)oxy)-1,2-dithian-4-yl benzoate (1.03 g, 3.1 mmol). The reaction mixture heated for 3 hours at 80° C. and then cooled and poured into water. The aqueous solution was extracted with ethyl acetate and the combined extracts were washed with water, dried over anhydrous Na$_2$SO$_4$, filtered and concentrated at reduced pressure. The pure product was obtained by column chromatography on silica gel (100-200 mesh) eluting with 40% ethyl acetate in hexanes to furnish the title compound as pale brown solid (200 mg, yield 23%). $^1$H-NMR (DMSO-d$_6$, 400 MHz) δ 8.41 (s, 1H), 8.02 (bs, 3H), 7.88 (d, J=6.0 Hz, 2H), 7.55-7.34 (m, 10H), 7.15 (dd, J$_1$=8.0 Hz, J$_2$=7.2 Hz, 1H), 7.05 (d, J=6.4 Hz, 1H), 5.43 (bs, 1H), 4.83 (d, J=7.8 Hz, 2H), 4.40 (t, J=4.0 Hz, 1H), 3.74 (dd, J$_1$=10.0 Hz, J$_2$=4.4 Hz, 1H), 3.29 (d, J$_1$=6.0 Hz, 1H); HPLC (retention time 10.7 minutes, [M+1]$^+$, 95.0%), Capcell pack C18 150*4.6, 3µ column at 254 nm.

Example 68 trans 3-((4-Amino-3-(3-(3-fluoro-4-phenoxyphenyl)-1H-pyrazolo[3,4-d]pyrimidin-1-yl)methyl)-1,2-dithiolan-4-ol

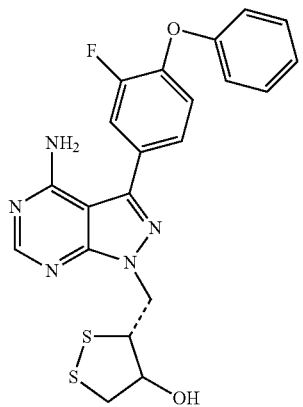

To a solution of trans 3-((4-amino-3-(3-(3-fluoro-4-phenoxyphenyl)-1H-pyrazolo[3,4-d]pyrimidin-1-yl)methyl)-1,2-dithiolan-4-yl benzoate (100 mg, 0.17 mmol) in tetrahydrofuran (10 mL) and methanol (1 mL) was added an aqueous solution of LiOH (20 mg, 0.71 mmol) in water (2 mL) and the reaction mixture was stirred for 3 hours at room temperature. The reaction mixture was quenched with ice water, acidified with citric acid and extracted with ethyl acetate. The extracts were combined, dried over anhydrous $Na_2SO_4$, filtered and evaporated in vacuo to afford the title compound as a pale yellow solid (30 mg, 31%); LCMS (retention time 7.15 minutes, 53%), Capcell pack C18 150*4.6, 3μ column at 254 nm.

Formulations

The present invention also relates to compositions or formulations which comprise the kinase inhibitors according to the present invention. In general, the compositions of the present invention comprise an effective amount of one or more 1,2-dithiolane and salts thereof according to the present invention which are effective for providing treatment or prevention of diseases that involve modulation of tyrosine kinases including NRTs such as SRFs and Tec and, RTKs such as FLT3, RET, FRK families. Said diseases include, for example, neurodegeneration, neuroprotection, Alzheimer's disease, ischemic stroke, autoimmune diseases, T-cell disorders, cancer such as, melanoma, adenocarcinoma, carcinoma, leukemia, chronic lymphoblastic leukemia, acute myeloid leukemia, adenocarcinoma, thyroid cancer, papillary thyroid carcinoma, medullary thyroid carcinoma, non-small cell lung cancer, small cell lung cancer, glioblastoma multiforme, colon, breast, prostate, testicular cancer malignant peripheral nerve sheath tumors. The method comprises administering to a subject an effective amount of a compound or composition according to the present invention and an excipient.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known kinase inhibitors. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and *arachis* oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more compounds of the disclosure according to the present invention and one or more excipients; from about 0.01 mg to about 100 mg of one or more compounds of the disclosure according to the present invention and one or more excipients; and from about 0.1 mg to about 10 mg of one or more compounds of the disclosure according to the present invention and one or more excipients.

Biological Activity

The following are abbreviations used in this section:
qPCR—quantitative polymerase chain reaction
BSA—bovine serum albumin
DTT—dithiothreitol
PBS—phosphate buffer saline
TWEEN 20—polyethoxylated sorbitan and oleic acid
Hepes—4-(2-hydroxyethyl)-1-piperazineethanesulfonic acid
EGTA—ethylene glycol-bis(2-aminoethyl ether)-N,N,N', N'-tetraacetic acid
Brij 35—polyoxyethyleneglycol dodecyl ether
ATP—adenosine triphosphate
ADP—adenosine diphosphate
Km—Michaelis constant The compounds of this invention are tested in the following Standard Pharmacological Test Procedures.

Methods for In Vitro Evaluation Assays known in the art for testing compounds are used to test compounds of this invention and to assess the biological activities. In order to support that this invention described herein, the following biological assays are set forth. Examples are for illustrative purposes only and are not met to be limiting.

Representative compounds of this invention, when tested in the assays described below demonstrated a binding constant Kd (nM) or $IC_{50}$ activity level (nM) as set forth in tables 5-22 wherein:
"A" refers to a Kd or $IC_{50}$ activity level of <5 nM;
"B" refers to a Kd or $IC_{50}$ activity level of from 5 nM to 99 nM;
"C" refers to a Kd or $IC_{50}$ activity level of from 100 nM to 999 nM;
"D" refers to a Kd or $IC_{50}$ activity level of 1,000 to 10,000 nM.

Data in tables 5-7 were obtained in the rabbit reticulocyte lysate assay. Data in tables 8-12 were obtained in the KINOMEscan™ assay. Data in tables 13-20 were obtained in the radioisotope filter binding assay. Data in table 21 were obtained in kinase binding assay CaPBA and data in table 22 were obtained in radiometric $^{33}$PanQinase$^R$ assay.

1. Rabbit Reticulocyte Lysate Assay Design:

KinaseSeeker is a homogeneous competition binding assay where the displacement of an active site dependent probe by an inhibitor is measured by a change in luminescence signal. Luminescence readout translates into a highly sensitive and robust assay with low background and minimal interference from test compounds.

10 mM stock solutions of test compounds were serially diluted in DMSO to make assay stocks. Prior to initiating $IC_{50}$ determinations, the test compounds were evaluated for false positive against split-luciferase.

Each test compound was screened in duplicate against target kinase at 7 different concentrations. For kinase assays, Cfluc-kinase was translated along with Fos-Nfluc using a cell-free system (rabbit reticulocyte lysate) at 30° C. for 90 min. 24 uL aliquot of this lysate containing either 1 uL of DMSO (for no-inhibitor control) or compound solution in DMSO was incubated for 30 minutes at room temperature followed by 1 hour in presence of a kinase specific probe. 80 uL of luciferin assay reagent was added to each solution and luminescence was immediately measured on a luminometer.

The % Inhibition and % Activity Remaining was calculated using the following equation:

% Inhibition=[($ALU_{Control}$−$ALU_{Sample}$)/$ALU_{Control}$]× 100

% Activity Remaining=100−% Inhibition

The % Activity was plotted against compound concentration and the $IC_{50}$ was determined for each compound using a 7-point curve (Jester, B. W.; et. al. *J. Am. Chem. Soc.* 2010, 132, 11727-11735. Jester, B. W., et. al. *J. Med. Chem.* 2012, 55, 1526-1537). Biological activity of representative compounds of the disclosure are described in Table 5.

pound to compete with the immobilized ligand is measured via quantitative PCR of the DNA tag.

For most assays, kinase-tagged T7 phage strains were prepared in an *E. coli* host derived from the BL21 strain. *E. coli* were grown to log-phase and infected with T7 phage and incubated with shaking at 32° C. until lysis. The lysates

TABLE 5

$IC_{50}$ Activity Levels Against SRC Family Kinases in nM

| Compounds Of Example # | Compound Name | SRC | BLK | FGR | YES1 | LCK | HCK |
|---|---|---|---|---|---|---|---|
| 43 B. | (3R,4S)-3-((4-amino-3-(4-phenoxyphenyl)-1H-pyrazolo[3,4-d]pyrimidin-1-yl)methyl)-1,2-dithiolan-4-ol | C | C | C | C | C | C |
| 46 B. | (3R,4R)-3-((4-amino-3-(4-phenoxyphenyl)-1H-pyrazolo[3,4-d]pyrimidin-1-yl)methyl)-1,2-dithiolan-4-ol | | | C | B | | |

TABLE 6

% Inhibition Against SRC Family Kinases at 1 µM

| Compounds Of Example # | Compound Name | SRC | CSK | FGR | FYN | YES1 | HCK | LYN |
|---|---|---|---|---|---|---|---|---|
| 33 A. | (3S,4R)-3-((4-amino-3-(4-methoxyphenyl)-1H-pyrazolo[3,4-d]pyrimidin-1-yl)methyl)-1,2-dithiolan-4-ol | 12 | 6 | 2 | 7 | 15 | 12 | |
| 33 B. | (3R,4S)-3-((4-amino-3-(4-methoxyphenyl)-1H-pyrazolo[3,4-d]pyrimidin-1-yl)methyl)-1,2-dithiolan-4-ol | 12 | 6 | 3 | 7 | 6 | 13 | |
| 44 A. | (3S,4R)-3-((4-amino-3-(4-phenoxyphenyl)-1H-pyrazolo[3,4-d]pyrimidin-1-yl)methyl)-1,2-dithiolan-4-ol | 49 | 50 | 84 | 33 | 90 | 73 | 33 |
| 43 B. | (3R,4S)-3-((4-amino-3-(4-phenoxyphenyl)-1H-pyrazolo[3,4-d]pyrimidin-1-yl)methyl)-1,2-dithiolan-4-ol | | 70 | | 77 | | | 57 |

TABLE 7

$IC_{50}$ Activity Levels Against Bruton Tyrosine Kinase in nM

| Compounds Of Example # | Compound Name | BTK |
|---|---|---|
| 42 | trans 3-((4-amino-3-(4-phenoxyphenyl)-1H-pyrazolo[3,4-d]pyrimidin-1-yl)methyl)-1,2-dithiolan-4-ol | C |
| 43 A. | (3S,4R)-3-((4-amino-3-(4-phenoxyphenyl)-1H-pyrazolo[3,4-d]pyrimidin-1-yl)methyl)-1,2-dithiolan-4-ol | D |
| 43 B. | (3R,4S)-3-((4-amino-3-(4-phenoxyphenyl)-1H-pyrazolo[3,4-d]pyrimidin-1-yl)methyl)-1,2-dithiolan-4-ol | C |
| 46 A. | (3S,4S)-3-((4-amino-3-(4-phenoxyphenyl)-1H-pyrazolo[3,4-d]pyrimidin-1-yl)methyl)-1,2-dithiolan-4-ol | D |
| 46 B. | (3R,4R)-3-((4-amino-3-(4-phenoxyphenyl)-1H-pyrazolo[3,4-d]pyrimidin-1-yl)methyl)-1,2-dithiolan-4-ol | D |

2. Kinase Assay (Kd):

KINOMEscan™ is based on a competition binding assay that quantitatively measures the ability of a test compound of the invention to compete with an immobilized, active-site directed ligand. The Kinase assay is performed by combining three components: DNA-tagged kinase; immobilized ligand; and a test compound. The ability of the test compound to compete with the immobilized ligand is measured via quantitative PCR of the DNA tag.

were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR.

TABLE 8

Kd Values in nM Against Representative TEC Family Kinases

| Compounds Of Example # | Compound Name | BTK | BMX |
|---|---|---|---|
| 37 | trans 1-((4-methoxy-1,2-dithiolan-3-yl)methyl)-3-(4-phenoxyphenyl)-1H-pyrazolo[3,4-d]pyrimidin-4-amine SAB217 | B | C |
| 38 | cis 1-((4-methoxy-1,2-dithiolan-3-yl)methyl)-3-(4-phenoxyphenyl)-1H-pyrazolo[3,4-d]pyrimidin-4-amine | B | C |
| 39 | trans 1-((4-(benzyloxy)-1,2-dithiolan-3-yl)methyl)-3-(4-phenoxyphenyl)-1H-pyrazolo[3,4-d]pyrimidin-4-amine | D | |
| 40 | cis 1-((4-(benzyloxy)-1,2-dithiolan-3-yl)methyl)-3-(4-phenoxyphenyl)-1H-pyrazolo[3,4-d]pyrimidin-4-amine | C | |
| 42 | trans 3-((4-amino-3-(4-phenoxyphenyl)-1H-pyrazolo[3,4-d]pyrimidin-1-yl)methyl)-1,2-dithiolan-4-ol | B | C |
| 45 | cis 3-((4-amino-3-(4-phenoxyphenyl)-1H-pyrazolo[3,4-d]pyrimidin-1-yl)methyl)-1,2-dithiolan-4-ol | B | |

TABLE 9

Kd Values in nM Against Representative MEK5 Kinase

| Compounds Of Example # | Compound Name | MEK5 |
|---|---|---|
| 28 | trans 3-((4-amino-3-phenyl-1H-pyrazolo[3,4-d]pyrimidin-1-yl)methyl)-1,2-dithiolan-4-ol | B |
| 30 | trans 3-((4-amino-3-(4-chlorophenyl)-1H-pyrazolo[3,4-d]pyrimidin-1-yl)methyl)-1,2-dithiolan-4-ol | A |
| 36 B. | (3R,4R)-3-((4-amino-3-(4-methoxyphenyl)-1H-pyrazolo[3,4-d]pyrimidin-1-yl)methyl)-1,2-dithiolan-4-ol | B |
| 37 | trans 1-((4-methoxy-1,2-dithiolan-3-yl)methyl)-3-(4-phenoxyphenyl)-1H-pyrazolo[3,4-d]pyrimidin-4-amine | A |
| 38 | cis 1-((4-methoxy-1,2-dithiolan-3-yl)methyl)-3-(4-phenoxyphenyl)-1H-pyrazolo[3,4-d]pyrimidin-4-amine | A |
| 39 | trans 1-((4-(benzyloxy)-1,2-dithiolan-3-yl)methyl)-3-(4-phenoxyphenyl)-1H-pyrazolo[3,4-d]pyrimidin-4-amine | B |
| 40 | cis 1-((4-(benzyloxy)-1,2-dithiolan-3-yl)methyl)-3-(4-phenoxyphenyl)-1H-pyrazolo[3,4-d]pyrimidin-4-amine | B |
| 43 A. | (3S,4R)-3-((4-amino-3-(4-phenoxyphenyl)-1H-pyrazolo[3,4-d]pyrimidin-1-yl)methyl)-1,2-dithiolan-4-ol | A |

TABLE 10

Kd Values in nM Against mTOR Kinase

| Compounds Of Example # | Compound Name | mTOR |
|---|---|---|
| 36 B. | (3R,4R)-3-((4-amino-3-(4-methoxyphenyl)-1H-pyrazolo[3,4-d]pyrimidin-1-yl)methyl)-1,2-dithiolan-4-ol | C |
| 37 | trans 1-((4-methoxy-1,2-dithiolan-3-yl)methyl)-3-(4-phenoxyphenyl)-1H-pyrazolo[3,4-d]pyrimidin-4-amine | D |
| 43 A. | (3S,4R)-3-((4-amino-3-(4-phenoxyphenyl)-1H-pyrazolo[3,4-d]pyrimidin-1-yl)methyl)-1,2-dithiolan-4-ol | D |
| 43 B. | (3R,4S)-3-((4-amino-3-(4-phenoxyphenyl)-1H-pyrazolo[3,4-d]pyrimidin-1-yl)methyl)-1,2-dithiolan-4-ol SAB297 | C |
| 46 A. | 3S,4S)-3-((4-amino-3-(4-phenoxyphenyl)-1H-pyrazolo[3,4-d]pyrimidin-1-yl)methyl)-1,2-dithiolan-4-ol | C |
| 46 B. | (3R,4R)-3-((4-amino-3-(4-phenoxyphenyl)-1H-pyrazolo[3,4-d]pyrimidin-1-yl)methyl)-1,2-dithiolan-4-ol | C |

TABLE 11

Kd Values in nM Against MAPK Pathway Kinases

| Compounds Of Example # | Compound Name | ERK1 | ERK2 | BRAF | BRAF (V600E) |
|---|---|---|---|---|---|
| 42 | trans 3-((4-amino-3-(4-phenoxyphenyl)-1H-pyrazolo[3,4-d]pyrimidin-1-yl)methyl)-1,2-dithiolan-4-ol | | | D | |
| 46 A. | (3S,4S)-3-((4-amino-3-(4-phenoxyphenyl)-1H-pyrazolo[3,4-d]pyrimidin-1-yl)methyl)-1,2-dithiolan-4-ol | | | D | |
| 46 B. | (3R,4R)-3-((4-amino-3-(4-phenoxyphenyl)-1H-pyrazolo[3,4-d]pyrimidin-1-yl)methyl)-1,2-dithiolan-4-ol | D | D | D | D |

TABLE 12

Kd Values in nM Against MEK Kinases Isoforms

| Compounds Of Example # | Compound Name | MEK1 | MEK2 | MEK3 | MEK4 | MEK5 | MEK6 | MEK7 |
|---|---|---|---|---|---|---|---|---|
| 43 B. | (3R,4S)-3-((4-amino-3-(4-phenoxyphenyl)-1H-pyrazolo[3,4-d]pyrimidin-1-yl)methyl)-1,2-dithiolan-4-ol | B | | | | A | | |
| 46 A. | (3S,4S)-3-((4-amino-3-(4-phenoxyphenyl)-1H-pyrazolo[3,4-d]pyrimidin-1-yl)methyl)-1,2-dithiolan-4-ol | C | | | | A | D | D |
| 46 B. | (3R,4R)-3-((4-amino-3-(4-phenoxyphenyl)-1H-pyrazolo[3,4-d]pyrimidin-1-yl)methyl)-1,2-dithiolan-4-ol | B | C | D | D | A | D | D |

3. Radioisotope Filter Binding Assay:

In this assay format, it directly detects the true product without the use of modified substrates or coupling enzymes (Uitdehaag, J. C., et al. *Br. J. Pharmacol.* 2012, 166, 858-876; Hastie, C. J., et al. *Nat. Protoc.* 2006, 1, 968-971) according to equation 1.

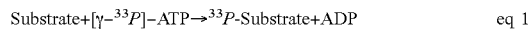

$$\text{Substrate} + [\gamma\text{-}^{33}P]\text{-ATP} \rightarrow {}^{33}P\text{-Substrate} + \text{ADP} \quad \text{eq 1}$$

The protocol calls for test compound of the invention to be incubated with kinase, substrate, cofactors, and radioisotope-labeled ATP ($^{33}$P-gamma-ATP). The reaction mixtures are then spotted onto filter papers which bind the radioisotope labeled catalytic product. Unreacted phosphate is removed via washing. The reagents used include base reaction buffer; 20 mM Hepes (pH 7.5), 10 mM MgCl2, 1 mM EGTA, 0.02% Brij35, 0.02 mg/ml BSA, 0.1 mM Na$_3$VO$_4$, 2 mM DTT, 1% DMSO. The reaction procedure include the following steps: (1) prepare indicated substrate in freshly prepared base reaction buffer, (2) deliver any required cofactors to the substrate solution above, (3) deliver indicated kinase into the substrate solution and gently mix, (4) deliver compounds in DMSO into the kinase reaction mixture by Acoustic technology (Echo550; nanoliter range), incubate for 20 minutes at room temperature, (5) deliver $^{33}$P-ATP (specific activity 10 µCi/µL) into the reaction mixture to initiate the reaction, (6) incubate kinase reaction for 2 hours at room temperature, (7) reactions are spotted onto P81 ion exchange paper, (8) detect kinase activity by filter-binding method.

TABLE 13

IC$_{50}$ Activity Levels Against SRC Family Kinases in nM

| Compounds Of Example # | Compound Name | SRC | YES1 | FGR | FYN | BLK | LCK | HCK | LYN | CSK |
|---|---|---|---|---|---|---|---|---|---|---|
| 37 | trans 1-((4-methoxy-1,2-dithiolan-3-yl)methyl)-3-(4-phenoxyphenyl)-1H-pyrazolo[3,4-d]pyrimidin-4-amine | | | | B | | | | | |
| 40 | cis 1-((4-(benzyloxy)-1,2-dithiolan-3-yl)methyl)-3-(4-phenoxyphenyl)-1H-pyrazolo[3,4-d]pyrimidin-4-amine | | | | D | | | | | |
| 43 A. | (3S,4R)-3-((4-amino-3-(4-phenoxyphenyl)-1H-pyrazolo[3,4-d]pyrimidin-1-yl)methyl)-1,2-dithiolan-4-ol | C | A | A | A | A | A | A | B | |
| 43 B. | (3R,4S)-3-((4-amino-3-(4-phenoxyphenyl)-1H-pyrazolo[3,4-d]pyrimidin-1-yl)methyl)-1,2-dithiolan-4-ol | B | A | A | A | B | A | A | B | B |

TABLE 13-continued

IC$_{50}$ Activity Levels Against SRC Family Kinases in nM

| Compounds Of Example # | Compound Name | SRC | YES1 | FGR | FYN | BLK | LCK | HCK | LYN | CSK |
|---|---|---|---|---|---|---|---|---|---|---|
| 46 A. | (3S,4S)-3-((4-amino-3-(4-phenoxyphenyl)-1H-pyrazolo[3,4-d]pyrimidin-1-yl)methyl)-1,2-dithiolan-4-ol | C | A | B | B | B | B | B | C | |
| 46 B. | (3R,4R)-3-((4-amino-3-(4-phenoxyphenyl)-1H-pyrazolo[3,4-d]pyrimidin-1-yl)methyl)-1,2-dithiolan-4-ol | B | A | A | A | A | A | B | B | |
| 62 | trans 3-((4-amino-3-(4-(2-fluorophenoxyphenyl)-1H-pyrazolo[3,4-d]pyrimidin-1-yl)methyl)-1,2-dithiolan-4-yl benzoate | | | | B | | | | | |
| 63 | trans 3-((4-amino-3-(4-(2-fluorophenoxyphenyl)-1H-pyrazolo[3,4-d]pyrimidin-1-yl)methyl)-1,2-dithiolan-4-ol | | | | B | | | | | |
| 67 | trans 3-((4-amino-3-(3-(3-fluoro-4-phenoxyphenyl)-1H-pyrazolo[3,4-d]pyrimidin-1-yl)methyl)-1,2-dithiolan-4-yl benzoate | | | | C | | | | | |

TABLE 14

IC$_{50}$ Activity Levels Against FYN Mutant in nM

| Compounds Of Example # | Compound Name | FYN-Y531F |
|---|---|---|
| 43 A. | (3S,4R)-3-((4-amino-3-(4-phenoxyphenyl)-1H-pyrazolo[3,4-d]pyrimidin-1-yl)methyl)-1,2-dithiolan-4-ol | B |
| 43 B. | (3R,4S)-3-((4-amino-3-(4-phenoxyphenyl)-1H-pyrazolo[3,4-d]pyrimidin-1-yl)methyl)-1,2-dithiolan-4-ol | C |
| 46 A. | (3S,4S)-3-((4-amino-3-(4-phenoxyphenyl)-1H-pyrazolo[3,4-d]pyrimidin-1-yl)methyl)-1,2-dithiolan-4-ol | B |
| 46 B. | (3R,4R)-3-((4-amino-3-(4-phenoxyphenyl)-1H-pyrazolo[3,4-d]pyrimidin-1-yl)methyl)-1,2-dithiolan-4-ol | B |

TABLE 15

IC$_{50}$ Activity Levels in nM Against Representative TEC Family Kinases

| Compounds Of Example # | Compound Name | BTK | BMX | ITK |
|---|---|---|---|---|
| 43 A. | (3S,4R)-3-((4-amino-3-(4-phenoxyphenyl)-1H-pyrazolo[3,4-d]pyrimidin-1-yl)methyl)-1,2-dithiolan-4-ol | B | | |
| 43 B. | (3R,4S)-3-((4-amino-3-(4-phenoxyphenyl)-1H-pyrazolo[3,4-d]pyrimidin-1-yl)methyl)-1,2-dithiolan-4-ol | B | B | D |
| 46 A. | (3S,4S)-3-((4-amino-3-(4-phenoxyphenyl)-1H-pyrazolo[3,4-d]pyrimidin-1-yl)methyl)-1,2-dithiolan-4-ol | B | | |
| 46 B. | (3R,4R)-3-((4-amino-3-(4-phenoxyphenyl)-1H-pyrazolo[3,4-d]pyrimidin-1-yl)methyl)-1,2-dithiolan-4-ol | B | | |

TABLE 16

IC$_{50}$ Activity Levels Against Type III NRT Kinases in nM

| Compounds Of Example # | Compound Name | FLT3 | FLT3-ITD |
|---|---|---|---|
| 43 A. | (3S,4R)-3-((4-amino-3-(4-phenoxyphenyl)-1H-pyrazolo[3,4-d]pyrimidin-1-yl)methyl)-1,2-dithiolan-4-ol | B | C |
| 43 B. | (3R,4S)-3-((4-amino-3-(4-phenoxyphenyl)-1H-pyrazolo[3,4-d]pyrimidin-1-yl)methyl)-1,2-dithiolan-4-ol | C | C |
| 46 A. | (3S,4S)-3-((4-amino-3-(4-phenoxyphenyl)-1H-pyrazolo[3,4-d]pyrimidin-1-yl)methyl)-1,2-dithiolan-4-ol | B | C |

TABLE 16-continued

IC$_{50}$ Activity Levels Against Type III NRT Kinases in nM

| Compounds Of Example # | Compound Name | FLT3 | FLT3-ITD |
|---|---|---|---|
| 46 B. | (3R,4R)-3-((4-amino-3-(4-phenoxyphenyl)-1H-pyrazolo[3,4-d]pyrimidin-1-yl)methyl)-1,2-dithiolan-4-ol | B | C |

TABLE 17

IC$_{50}$ Activity Levels Against FRK Family Kinases in nM

| Compounds Of Example # | Compound Name | BRK | FRK |
|---|---|---|---|
| 43 A. | (3S,4R)-3-((4-amino-3-(4-phenoxyphenyl)-1H-pyrazolo[3,4-d]pyrimidin-1-yl)methyl)-1,2-dithiolan-4-ol | B | |
| 43 B. | (3R,4S)-3-((4-amino-3-(4-phenoxyphenyl)-1H-pyrazolo[3,4-d]pyrimidin-1-yl)methyl)-1,2-dithiolan-4-ol | B | B |
| 46 A. | (3S,4S)-3-((4-amino-3-(4-phenoxyphenyl)-1H-pyrazolo[3,4-d]pyrimidin-1-yl)methyl)-1,2-dithiolan-4-ol | B | |
| 46 B. | (3R,4R)-3-((4-amino-3-(4-phenoxyphenyl)-1H-pyrazolo[3,4-d]pyrimidin-1-yl)methyl)-1,2-dithiolan-4-ol | B | |

TABLE 18

IC$_{50}$ Activity Levels Against MAPK Pathway Kinases in nM

| Compounds Of Example # | Compound Name | ARAF | BRAF | CRAP | KDR/VEGFR2 |
|---|---|---|---|---|---|
| 43 A. | (3S,4R)-3-((4-amino-3-(4-phenoxyphenyl)-1H-pyrazolo[3,4-d]pyrimidin-1-yl)methyl)-1,2-dithiolan-4-ol | C | | D | |
| 43 B. | (3R,4S)-3-((4-amino-3-(4-phenoxyphenyl)-1H-pyrazolo[3,4-d]pyrimidin-1-yl)methyl)-1,2-dithiolan-4-ol | | | | |
| 46 A. | (3S,4S)-3-((4-amino-3-(4-phenoxyphenyl)-1H-pyrazolo[3,4-d]pyrimidin-1-yl)methyl)-1,2-dithiolan-4-ol | D | D | D | D |
| 46 B. | (3R,4R)-3-((4-amino-3-(4-phenoxyphenyl)-1H-pyrazolo[3,4-d]pyrimidin-1-yl)methyl)-1,2-dithiolan-4-ol | C | D | D | D |

TABLE 19

IC$_{50}$ Activity Levels Against RTKs (c-Kit, RET, HER4) and AurA, CHK2 Kinases in nM

| Compounds Of Example # | Compound Name | AurA | CHK2 | c-KIT | RET | HER4 |
|---|---|---|---|---|---|---|
| 46 A. | (3S,4S)-3-((4-amino-3-(4-phenoxyphenyl)-1H-pyrazolo[3,4-d]pyrimidin-1-yl)methyl)-1,2-dithiolan-4-ol | | | D | C | D |
| 46 B. | (3R,4R)-3-((4-amino-3-(4-phenoxyphenyl)-1H-pyrazolo[3,4-d]pyrimidin-1-yl)methyl)-1,2-dithiolan-4-ol | C | | D | D | B |
| 55 | trans 3-((4-amino-3-(2-aminobenzo[d]oxazol-5-yl)-1H-pyrazolo[3,4-d]pyrimidin-1-yl)methyl)-1,2-dithiolan-4-yl benzoate | | D | | | |

TABLE 20

IC$_{50}$ Activity Levels Against Various PI3K and mTor Kinases in nM

| Compounds Of Example # | Compound Name | mTor/FRAP1 | PI3K α | PI3K β | PI3K γ | PI3K δ |
|---|---|---|---|---|---|---|
| 51 | trans 3-((4-amino-3-(phenylethynyl)-1H-pyrazolo[3,4-d]pyrimidin-1-yl)methyl-1,2-dithiolan-4-yl benzoate | D | | | | |
| 52 | trans 3-(4-amino-3-(phenylethynyl)-1H-pyrazolo[3,4-d]pyrimidin-1-yl)methyl-1,2-dithiolan-4-ol | D | | | | |
| 55 | trans 3-((4-amino-3-(2-aminobenzo[d]oxazol-5-yl)-1H-pyrazolo[3,4-d]pyrimidin-1-yl)methyl)-1,2-dithiolan-4-yl benzoate | B | C | D | D | C |

4. Kinase Binding Assay CaPBA:

This assay is based on a competitive binder which can interact with a latent pocket formed only in the inactive state of the kinase. A fluorescent probe is used to bind to the inactive form of the enzyme and is displaced competitively by a binder upon shining light.

TABLE 21

IC$_{50}$ Activity Levels Against FYN isoforms, YES1 and MEK5 in nM

| Compound Of Example # | Compound Name | FYN isoform (a) | FYN isoform (b) | YES1 | MEK5 |
|---|---|---|---|---|---|
| 43 A. | (3S,4R)-3-((4-amino-3-(4-phenoxyphenyl)-1H-pyrazolo[3,4-d]pyrimidin-1-yl)methyl)-1,2-dithiolan-4-ol | B | B | A | |
| 43 B. | (3R,4S)-3-((4-amino-3-(4-phenoxyphenyl)-1H-pyrazolo[3,4-d]pyrimidin-1-yl)methyl)-1,2-dithiolan-4-ol | B | B | A | D |
| 46 B. | (3R,4R)-3-((4-amino-3-(4-phenoxyphenyl)-1H-pyrazolo[3,4-d]pyrimidin-1-yl)methyl)-1,2-dithiolan-4-ol | | | A | D |

5. Radiometric $^{33}$PanQinase$^R$ Assay:

This assay referred to as FlashPlate-based Protein Kinase Assay uses recombinant protein kinase and ATP concentration corresponding to the apparent ATP-Km of the respective kinase. Testing of inhibitors is done at app. ATP Km.

TABLE 22

IC$_{50}$ Activity Levels Against FYN Kinase in nM

| Compounds Of Example # | Compound Name | FYN |
|---|---|---|
| 43 B. | (3R,4S)-3-((4-amino-3-(4-phenoxyphenyl)-1H-pyrazolo[3,4-d]pyrimidin-1-yl)methyl)-1,2-dithiolan-4-ol | B |
| 46 B. | (3R,4R)-3-((4-amino-3-(4-phenoxyphenyl)-1H-pyrazolo[3,4-d]pyrimidin-1-yl)methyl)-1,2-dithiolan-4-ol | B |

What is claimed is:

1. A compound of formula (I):

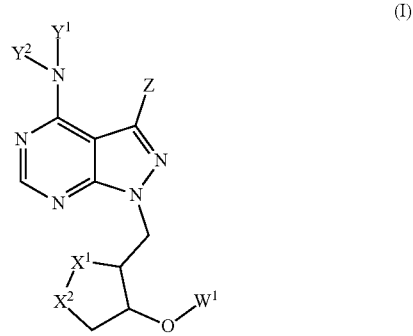

wherein:

$W^1$ is selected from a group consisting of hydrogen, $C_{1-6}$ alkyl, $C_{3-7}$ cycloalkyl, cycloalkylalkyl, aryl, arylalkyl, $C(O)R^1$, $C(O)R^2$, $C(O)OR^1$, $C(O)OR^2$, trialkylsilyl and diarylalkylsilyl;

$X^1$ and $X^2$ are each independently selected from the group consisting of S, SO and $SO_2$;

$Y^1$ and $Y^2$ are each independently selected from the group consisting of hydrogen, $C_{1-6}$ alkyl, $C(O)R^1$, $C(O)R^2$, $C(O)OR^1$, and $C(O)OR^2$;

Z is selected from the group consisting of hydrogen, arylalkynyl, halogen,

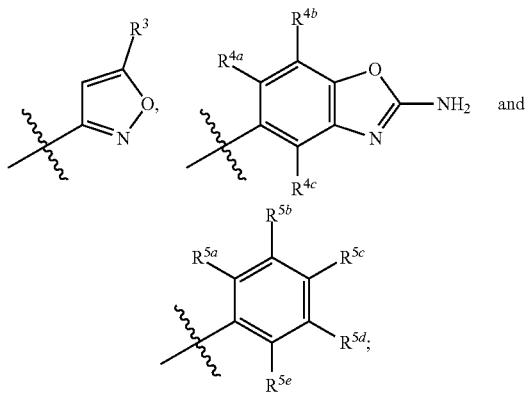

$R^1$ is selected from the group of hydrogen, $C_{1-6}$ alkyl, and $C_{3-7}$ cycloalkyl;

$R^2$ is selected from the group of hydrogen, aryl, and arylalkyl;

$R^3$ is selected from the group of hydrogen, $C_{1-6}$ alkyl, $C_{3-7}$ cycloalkyl, phenyl, benzyl, and halogen;

$R^{4a}$, $R^{4b}$, and $R^{4c}$ are each independently selected from the group of hydrogen, $C_{1-6}$ alkyl, $C_{1-6}$ haloalkyl, $C_{1-6}$ alkoxy, $C_{3-7}$ cycloalkyl, halogen, aryl, arylalkyl, and aryloxy;

$R^{5a}$, $R^{5b}$, $R^{5c}$, $R^{5d}$ and $R^{5e}$ are each independently selected from the group of hydrogen, $C_{1-6}$ alkyl, halogen, $C_{1-6}$ alkoxy, aryl, arylalkyl, aryloxy, and arylalkynyl;

or an enantiomer, diastereomer, hydrate, solvate, or a pharmaceutically acceptable salt thereof.

2. A compound according to claim 1, wherein Z is the moiety

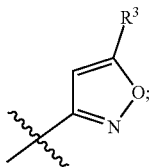

or an enantiomer, diastereomer, hydrate, solvate, or a pharmaceutically acceptable salt thereof.

3. A compound according to claim 1, wherein Z is the moiety

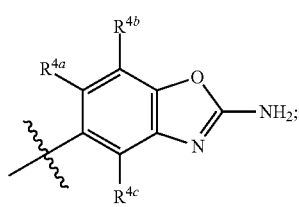

or an enantiomer, diastereomer, hydrate, solvate, a pharmaceutically acceptable salt thereof.

4. A compound according to claim 1, wherein Z is the moiety

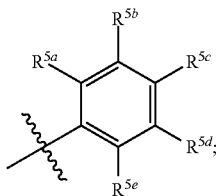

or an enantiomer, diastereomer, hydrate, solvate, or a pharmaceutically acceptable salt thereof.

5. A compound according to claim 1, wherein $Y^1$ and $Y^2$ are H, and $X^1$ and $X^2$ are S, or an enantiomer, diastereomer, hydrate, solvate, a pharmaceutically acceptable salt thereof.

6. A compound according to claim 1, wherein $Y^1$ and $Y^2$ are H, $X^1$ and $X^2$ are S, and Z is a moiety

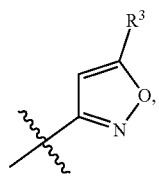

or an enantiomer, diastereomer, hydrate, solvate, a pharmaceutically acceptable salt thereof.

7. A compound according to claim 1, wherein $Y^1$ and $Y^2$ are H, $X^1$ and $X^2$ are S, and Z is a moiety

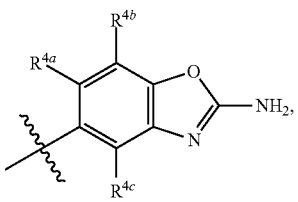

or an enantiomer, diastereomer, hydrate, solvate, a pharmaceutically acceptable salt thereof.

8. A compound according to claim 1, wherein Z is arylalkynyl, $X^1$ and $X^2$ are S, and $Y^1$ and $Y^2$ are H, or an enantiomer, diastereomer, hydrate, solvate, a pharmaceutically acceptable salt thereof.

9. A compound selected from the group consisting of:
trans 3-((4-Amino-3-phenyl-1H-pyrazolo[3,4-d]pyrimidin-1-yl)methyl)-1,2-dithiolan-4-yl benzoate),
trans 3-((4-Amino-3-phenyl-1H-pyrazolo[3,4-d]pyrimidin-1-yl)methyl)-1,2-dithiolan-4-ol,
trans 3-((4-Amino-3-(4-chlorophenyl)-1H-pyrazolo[3,4-d]pyrimidin-1-yl)methyl)-1,2-dithiolan-4-yl benzoate,
trans 3-((4-Amino-3-(4-chlorophenyl)-1H-pyrazolo[3,4-d]pyrimidin-1-yl)methyl)-1,2-dithiolan-4-ol,
trans 3-((4-Amino-3-(4-methoxyphenyl)-1H-pyrazolo[3,4-d]pyrimidin-1-yl)methyl)-1,2-dithiolan-4-yl benzoate,
trans 3-((4-Amino-3-(4-methoxyphenyl)-1H-pyrazolo[3,4-d]pyrimidin-1-yl)methyl)-1,2-dithiolan-4-ol,
(3S,4R)-3-((4-Amino-3-(4-methoxyphenyl)-1H-pyrazolo[3,4-d]pyrimidin-1-yl)methyl)-1,2-dithiolan-4-ol, (3R,4S)-3-((4-Amino-3-(4-methoxyphenyl)-1H-pyrazolo[3,4-d]pyrimidin-1-yl)methyl)-1,2-dithiolan-4-ol,
cis 3-((4-Amino-3-(4-methoxyphenyl)-1H-pyrazolo[3,4-d]pyrimidin-1-yl)methyl)-1,2-dithiolan-4-yl benzoate,
cis 3-((4-Amino-3-(4-methoxyphenyl)-1H-pyrazolo[3,4-d]pyrimidin-1-yl)methyl)-1,2-dithiolan-4-ol,
(3S,4S)-3-((4-Amino-3-(4-methoxyphenyl)-1H-pyrazolo[3,4-d]pyrimidin-1-yl)methyl)-1,2-dithiolan-4-ol,
(3R,4R)-3-((4-Amino-3-(4-methoxyphenyl)-1H-pyrazolo[3,4-d]pyrimidin-1-yl)methyl)-1,2-dithiolan-4-ol,
trans 1-((4-Methoxy-1,2-dithiolan-3-yl)methyl)-3-(4-phenoxyphenyl)-1H-pyrazolo[3,4-d]pyrimidin-4-amine,
cis 1-((4-Methoxy-1,2-dithiolan-3-yl)methyl)-3-(4-phenoxyphenyl)-1H-pyrazolo[3,4-d]pyrimidin-4-amine,
trans 1-((4-(Benzyloxy)-1,2-dithiolan-3-yl)methyl)-3-(4-phenoxyphenyl)-1H-pyrazolo[3,4-d]pyrimidin-4-amine,
cis 1-((4-(Benzyloxy)-1,2-dithiolan-3-yl)methyl)-3-(4-phenoxyphenyl)-1H-pyrazolo[3,4-d]pyrimidin-4-amine,
trans 3-((4-Amino-3-(4-phenoxyphenyl)-1H-pyrazolo[3,4-d]pyrimidin-1-yl)methyl)-1,2-dithiolan-4-yl benzoate,
(3S,4R)-3-((4-Amino-3-(4-phenoxyphenyl)-1H-pyrazolo[3,4-d]pyrimidin-1-yl)methyl)-1,2-dithiolan-4-ol,
(3R,4S)-3-((4-Amino-3-(4-phenoxyphenyl)-1H-pyrazolo[3,4-d]pyrimidin-1-yl)methyl)-1,2-dithiolan-4-ol,
cis 3-((4-Amino-3-(4-phenoxyphenyl)-1H-pyrazolo[3,4-d]pyrimidin-1-yl)methyl)-1,2-dithiolan-4-yl benzoate,
cis 3-((4-Amino-3-(4-phenoxyphenyl)-1H-pyrazolo[3,4-d]pyrimidin-1-yl)methyl)-1,2-dithiolan-4-ol,
(3S,4S)-3-((4-Amino-3-(4-phenoxyphenyl)-1H-pyrazolo[3,4-d]pyrimidin-1-yl)methyl)-1,2-dithiolan-4-ol,
(3R,4R)-3-((4-Amino-3-(4-phenoxyphenyl)-1H-pyrazolo[3,4-d]pyrimidin-1-yl)methyl)-1,2-dithiolan-4-ol,
trans-1-((4-((tert-Butyldimethylsilyl)oxy)-1,2-dithiolan-3-yl)methyl)-3-(4-phenoxyphenyl)-1-1H-pyrazolo[3,4-d]pyrimidin-4-amine,
trans 3-((4-Amino-3-(4-phenoxyphenyl)-1H-pyrazolo[3,4-d]pyrimidin-1-yl)methyl)-1,2-dithiolan-4-ol,
trans 3-((4-Amino-3-(phenylethynyl)-1H-pyrazolo[3,4-d]pyrimidin-1-yl)methyl-1,2-dithiolan-4-yl benzoate,
trans 3-((4-Amino-3-(phenylethynyl)-1H-pyrazolo[3,4-d]pyrimidin-1-yl)methyl-1,2-dithiolan-4-ol,
trans 3-((4-Amino-3-(phenylethynyl)-1H-pyrazolo[3,4-d]pyrimidin-1-yl)methyl-1-oxido-1,2-dithiolan-4-yl benzoate,
trans 3-((4-Amino-3-(2-aminobenzo[d]oxazol-5-yl)-1H-pyrazolo[3,4-d]pyrimidin-1-yl)methyl)-1,2-dithiolan-4-yl benzoate,
trans 3-((4-Amino-3-(2-aminobenzo[d]oxazol-5-yl)-1H-pyrazolo[3,4-d]pyrimidin-1-yl)methyl)-1,2-dithiolan-4-ol,
trans 3-((4-Amino-3-(2-aminobenzo[d]oxazol-5-yl)-1H-pyrazolo[3,4-d]pyrimidin-1-yl)methyl)-1-oxido-1,2-dithiolan-4-yl benzoate,
trans 3-((4-Amino-3-(2-aminobenzo[d]oxazol-5-yl)-1H-pyrazolo[3,4-d]pyrimidin-1-yl)methyl)-4-hydroxy-1,2-dithiolane 1-oxide,
trans 3-((4-Amino-3-(4-(2-fluorophenoxyphenyl)-1H-pyrazolo[3,4-d]pyrimidin-1-yl)methyl)-1,2-dithiolan-4-yl benzoate,
trans 3-((4-Amino-3-(4-(2-fluorophenoxyphenyl)-1H-pyrazolo[3,4-d]pyrimidin-1-yl)methyl)-1,2-dithiolan-4-ol,
trans 3-((4-Amino-3-(3-(3-fluoro-4-phenoxyphenyl)-1H-pyrazolo[3,4-d]pyrimidin-1-yl)methyl)-1,2-dithiolan-4-yl benzoate and,
trans 3-((4-Amino-3-(3-(3-fluoro-4-phenoxyphenyl)-1H-pyrazolo[3,4-d]pyrimidin-1-yl)methyl)-1,2-dithiolan-4-ol;

or an enantiomer, diastereomer, hydrate, solvate, a pharmaceutically acceptable salt thereof.

10. A compound according to claim 1, wherein Z is the moiety

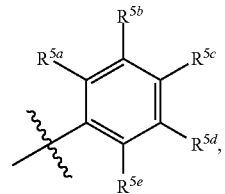

$Y^1$ is H; $R^{5a}$, $R^{5b}$, $R^{5d}$, and $R^{5e}$ are H; and $X^1$, $X^2$, $Y^2$, $R^{5c}$ and $W^1$ are selected as a single group from one of the following groups:

| Group Number | $X^1$ | $X^2$ | $Y^2$ | $R^{5c}$ | $W^1$ |
|---|---|---|---|---|---|
| 1 | S | SO | H | OPhenyl | H, |
| 2 | SO | S | H | OPhenyl | H, |
| 3 | S | SO | H | OPhenyl | $CH_3$, |
| 4 | SO | S | H | OPhenyl | $CH_3$, |
| 5 | S | SO | $CO_2$-t-Butyl | OPhenyl | H, |
| 6 | SO | S | $CO_2$-t-Butyl | OPhenyl | H, |
| 7 | S | SO | $CO_2$-t-Butyl | OPhenyl | $CH_3$, |
| 8 | SO | S | $CO_2$-t-Butyl | OPhenyl | $CH_3$, |
| 9 | S | SO | $COCH_3$ | OPhenyl | $CO_2CH_3$, |
| 10 | SO | S | $COCH_3$ | OPhenyl | $CO_2CH_3$, |
| 11 | S | SO | H | $OCH_3$ | H, |
| 12 | SO | S | H | $OCH_3$ | H, |
| 13 | S | SO | H | $OCH_3$ | $CH_3$, |
| 14 | SO | S | H | $OCH_3$ | $CH_3$, |
| 15 | SO | SO | H | OPhenyl | H and |
| 16 | SO | SO | H | $OCH_3$ | H | or an enantiomer, diastereomer, hydrate, solvate, a pharmaceutically acceptable salt thereof.

11. A compound according to claim 1, wherein Z is the moiety

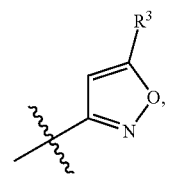

$Y^1$ is H, and $X^1$, $X^2$, $Y^2$, $R^3$ and $W^1$ are selected are selected as a single group from one of the following groups:

| Group Number | $X^1$ | $X^2$ | $Y^2$ | $R^3$ | $W^1$ |
|---|---|---|---|---|---|
| 1 | S | SO | H | Phenyl | H, |
| 2 | SO | S | H | Phenyl | H, |
| 3 | S | SO | H | $CH_2$Phenyl | $CH_3$, |

-continued

| Group Number | $X^1$ | $X^2$ | $Y^2$ | $R^3$ | $W^1$ |
|---|---|---|---|---|---|
| 4 | SO | S | H | CH$_2$Phenyl | CH$_3$, |
| 5 | S | SO | CO$_2$-t-Butyl | c-propyl | H, |
| 6 | SO | S | CO$_2$-t-Butyl | c-propyl | H, |
| 7 | S | SO | CO$_2$-t-Butyl | c-propyl | CH$_3$, |
| 8 | SO | S | CO$_2$-t-Butyl | c-propyl | CH$_3$, |
| 9 | S | SO | COCH$_3$ | c-propyl | c-pentyl, |
| 10 | SO | S | COCH$_3$ | c-propyl | c-pentyl, |
| 11 | S | SO | H | c-butyl | CH$_3$, |
| 12 | SO | S | H | c-butyl | CH$_3$, |
| 13 | S | SO | H | Br | CH$_3$, |
| 14 | SO | S | H | Br | CH$_3$, |
| 15 | S | SO | H | i-propyl | H and |
| 16 | SO | S | H | i-propyl | H | or an enantiomer, diastereomer, hydrate, solvate, a pharmaceutically acceptable salt thereof.

12. A compound according to claim 1, wherein Z is the moiety

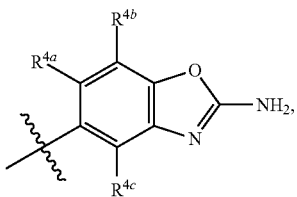

$Y^1$ is H, and $X^1$, $X^2$, $Y^2$, $R^{4b}$ and $W^1$ are selected as a single group from one of the following groups:

| Group Number | $X^1$ | $X^2$ | $Y^2$ | $R^{4b}$ | $W^1$ |
|---|---|---|---|---|---|
| 1 | S | SO | H | Cl | H, |
| 2 | SO | S | H | Cl | H, |
| 3 | S | SO | H | F | CH$_3$, |
| 4 | SO | S | H | F | CH$_3$, |
| 5 | S | SO | CO$_2$-t-Butyl | OCH$_3$ | H, |
| 6 | SO | S | CO$_2$-t-Butyl | OCH$_3$ | H, |
| 7 | S | SO | CO$_2$-t-Butyl | F | CH$_3$, |
| 8 | SO | S | CO$_2$-t-Butyl | F | CH$_3$, |
| 9 | S | SO | COCH$_3$ | c-propyl | c-pentyl, |
| 10 | SO | S | COCH$_3$ | c-propyl | c-pentyl, |
| 11 | S | SO | H | H | CH$_3$, |
| 12 | SO | S | H | H | CH$_3$, |
| 13 | S | SO | H | H | Phenyl, |
| 14 | SO | S | H | H | Phenyl, |
| 15 | S | SO | H | F | H and |
| 16 | SO | S | H | F | H | or an enantiomer, diastereomer, hydrate, solvate, a pharmaceutically acceptable salt thereof.

13. A compound according to claim 1, wherein:
Z is ethynylbenzene, $Y^1$ is H, and $X^1$, $X^2$, $Y^2$ and $W^1$ are selected as a single group from one of the following groups:

| Group Number | $X^1$ | $X^2$ | $Y^2$ | $W^1$ |
|---|---|---|---|---|
| 1 | S | SO | H | H, |
| 2 | SO | S | H | H, |
| 3 | S | SO | H | CH$_3$, |
| 4 | SO | S | H | CH$_3$, |
| 5 | S | SO | CO$_2$-t-Butyl | H, |
| 6 | SO | S | CO$_2$-t-Butyl | H, |
| 7 | S | SO | CO$_2$-t-Butyl | CH$_3$, |
| 8 | SO | S | CO$_2$-t-Butyl | CH$_3$, |
| 9 | S | SO | COCH$_3$ | CO$_2$—CH$_3$, |
| 10 | SO | S | COCH$_3$ | CO$_2$—CH$_3$, |
| 11 | S | SO | H | c-pentyl, |
| 12 | SO | S | H | c-pentyl, |
| 13 | S | SO | H | c-propyl, |
| 14 | SO | S | H | c-propyl, |
| 15 | S | SO | H | CH$_2$Phenyl and |
| 16 | SO | S | H | CH$_2$Phenyl, | or an enantiomer, diastereomer, hydrate, solvate, a pharmaceutically acceptable salt thereof.

14. A pharmaceutical composition comprising a compound according to claim 1 or an enantiomer, diastereomer, hydrate, solvate, or an enantiomer, diastereomer, hydrate, solvate, a pharmaceutically acceptable salt thereof, and a pharmaceutically acceptable carrier.

15. A compound of formula (I):

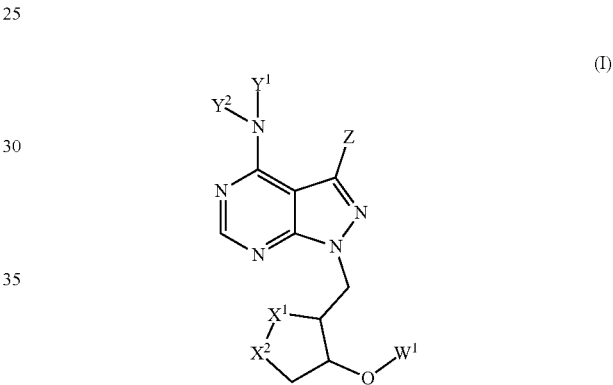

wherein
(a) Z is moiety

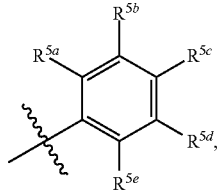

$Y^1$ is H; $R^{5a}$, $R^{5b}$, $R^{5d}$, and $R^{5e}$ are H; and $X^1$, $X^2$, $Y^2$, $R^{5c}$ and $W^1$ are selected as a single group from one of the following groups:

| Group Number | $X^1$ | $X^2$ | $Y^2$ | $R^{5c}$ | $W^1$ |
|---|---|---|---|---|---|
| 1 | S | SO | H | OPhenyl | H, |
| 2 | SO | S | H | OPhenyl | H, |
| 3 | S | SO | H | OPhenyl | CH$_3$, |
| 4 | SO | S | H | OPhenyl | CH$_3$, |
| 5 | S | SO | CO$_2$-t-Butyl | OPhenyl | H, |
| 6 | SO | S | CO$_2$-t-Butyl | OPhenyl | H, |
| 7 | S | SO | CO$_2$-t-Butyl | OPhenyl | CH$_3$, |

-continued

| Group Number | $X^1$ | $X^2$ | $Y^2$ | $R^{5c}$ | $W^1$ |
|---|---|---|---|---|---|
| 8 | SO | S | $CO_2$-t-Butyl | OPhenyl | $CH_3$, |
| 9 | S | SO | $COCH_3$ | OPhenyl | $CO_2CH_3$, |
| 10 | SO | S | $COCH_3$ | OPhenyl | $CO_2CH_3$, |
| 11 | S | SO | H | $OCH_3$ | H, |
| 12 | SO | S | H | $OCH_3$ | H, |
| 13 | S | SO | H | $OCH_3$ | $CH_3$, |
| 14 | SO | S | H | $OCH_3$ | $CH_3$, |
| 15 | SO | SO | H | OPhenyl | H and |
| 16 | SO | SO | H | $OCH_3$ | H | or an enantiomer, diastereomer, hydrate, solvate, a pharmaceutically acceptable salt thereof; or (b) Z is moiety

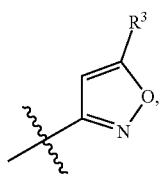

$Y^1$ is H, and $X^1$, $X^2$, $Y^2$, $R^3$ and $W^1$ are selected are selected as a single group from one of the following groups:

| Group Number | $X^1$ | $X^2$ | $Y^2$ | $R^3$ | $W^1$ |
|---|---|---|---|---|---|
| 1 | S | SO | H | Phenyl | H, |
| 2 | SO | S | H | Phenyl | H, |
| 3 | S | SO | H | $CH_2$Phenyl | $CH_3$, |
| 4 | SO | S | H | $CH_2$Phenyl | $CH_3$, |
| 5 | S | SO | $CO_2$-t-Butyl | c-propyl | H, |
| 6 | SO | S | $CO_2$-t-Butyl | c-propyl | H, |
| 7 | S | SO | $CO_2$-t-Butyl | c-propyl | $CH_3$, |
| 8 | SO | S | $CO_2$-t-Butyl | c-propyl | $CH_3$, |
| 9 | S | SO | $COCH_3$ | c-propyl | c-pentyl, |
| 10 | SO | S | $COCH_3$ | c-propyl | c-pentyl, |
| 11 | S | SO | H | c-butyl | $CH_3$, |
| 12 | SO | S | H | c-butyl | $CH_3$, |
| 13 | S | SO | H | Br | $CH_3$, |
| 14 | SO | S | H | Br | $CH_3$, |
| 15 | S | SO | H | i-propyl | H and |
| 16 | SO | S | H | i-propyl | H, | or an enantiomer, diastereomer, hydrate, solvate, a pharmaceutically acceptable salt thereof; or (c) Z is a moiety

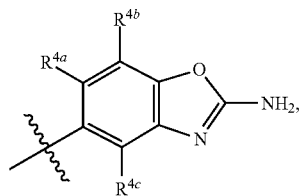

$Y^1$, $R^{4a}$ and $R^{4c}$ are each H, and $X^1$, $X^2$, $Y^2$, $R^{4b}$ and $W^1$ are selected as a single group from one of the following groups:

| Group Number | $X^1$ | $X^2$ | $Y^2$ | $R^{4b}$ | $W^1$ |
|---|---|---|---|---|---|
| 1 | S | SO | H | Cl | H, |
| 2 | SO | S | H | Cl | H, |
| 3 | S | SO | H | F | $CH_3$, |
| 4 | SO | S | H | F | $CH_3$, |
| 5 | S | SO | $CO_2$-t-Butyl | $OCH_3$ | H, |
| 6 | SO | S | $CO_2$-t-Butyl | $OCH_3$ | H, |
| 7 | S | SO | $CO_2$-t-Butyl | F | $CH_3$, |
| 8 | SO | S | $CO_2$-t-Butyl | F | $CH_3$, |
| 9 | S | SO | $COCH_3$ | c-propyl | c-pentyl, |
| 10 | SO | S | $COCH_3$ | c-propyl | c-pentyl, |
| 11 | S | SO | H | H | $CH_3$, |
| 12 | SO | S | H | H | $CH_3$, |
| 13 | S | SO | H | H | Phenyl, |
| 14 | SO | S | H | H | Phenyl, |
| 15 | S | SO | H | F | H and |
| 16 | SO | S | H | F | H | or an enantiomer, diastereomer, hydrate, solvate, a pharmaceutically acceptable salt thereof; or (d) Z is ethynylbenzene, $Y^1$ is H, and $X^1$, $X^2$, $Y^2$ and $W^1$ are selected as a single group from one of the following groups:

| Group Number | $X^1$ | $X^2$ | $Y^2$ | $W^1$ |
|---|---|---|---|---|
| 1 | S | SO | H | H, |
| 2 | SO | S | H | H, |
| 3 | S | SO | H | $CH_3$, |
| 4 | SO | S | H | $CH_3$, |
| 5 | S | SO | $CO_2$-t-Butyl | H, |
| 6 | SO | S | $CO_2$-t-Butyl | H, |
| 7 | S | SO | $CO_2$-t-Butyl | $CH_3$, |
| 8 | SO | S | $CO_2$-t-Butyl | $CH_3$, |
| 9 | S | SO | $COCH_3$ | $CO_2$—$CH_3$, |
| 10 | SO | S | $COCH_3$ | $CO_2$—$CH_3$, |
| 11 | S | SO | H | c-pentyl, |
| 12 | SO | S | H | c-pentyl, |
| 13 | S | SO | H | c-propyl, |
| 14 | SO | S | H | c-propyl, |
| 15 | S | SO | H | $CH_2$Phenyl and |
| 16 | SO | S | H | $CH_2$Phenyl, | or an enantiomer, diastereomer, hydrate, solvate, a pharmaceutically acceptable salt thereof.

* * * * *